(12) United States Patent
Cantley et al.

(10) Patent No.: US 8,877,791 B2
(45) Date of Patent: Nov. 4, 2014

(54) INHIBITORS OF PYRUVATE KINASE AND METHODS OF TREATING DISEASE

(75) Inventors: Lewis Cantley, Cambridge, MA (US); Matthew G. Vander Heiden, Somerville, MA (US); Heather R. Christofk, Carlsbad, CA (US)

(73) Assignee: Beth Israel Deaconess Medical Center, Inc., Boston, MA (US)

( * ) Notice: Subject to any disclaimer, the term of this patent is extended or adjusted under 35 U.S.C. 154(b) by 2 days.

(21) Appl. No.: 12/376,285

(22) PCT Filed: Aug. 6, 2007

(86) PCT No.: PCT/US2007/017519
§ 371 (c)(1),
(2), (4) Date: Nov. 24, 2009

(87) PCT Pub. No.: WO2008/019139
PCT Pub. Date: Feb. 14, 2008

(65) Prior Publication Data
US 2010/0099726 A1    Apr. 22, 2010

Related U.S. Application Data

(60) Provisional application No. 60/835,821, filed on Aug. 4, 2006.

(51) Int. Cl.
| | | |
|---|---|---|
| A61K 31/00 | (2006.01) | |
| A61K 31/381 | (2006.01) | |
| A61K 31/4184 | (2006.01) | |
| A61K 31/402 | (2006.01) | |
| A61K 31/426 | (2006.01) | |

(52) U.S. Cl.
CPC ............. *A61K 31/4184* (2013.01); *A61K 31/00* (2013.01); *A61K 31/381* (2013.01); *A61K 31/402* (2013.01); *A61K 31/426* (2013.01)
USPC .......................................... 514/394; 514/429

(58) Field of Classification Search
None
See application file for complete search history.

(56) References Cited

U.S. PATENT DOCUMENTS

| | | | | |
|---|---|---|---|---|
| 3,097,210 | A | | 7/1963 | Bicking |
| 4,775,762 | A | | 10/1988 | Knox et al. |
| 5,122,530 | A | | 6/1992 | Tomioka et al. |
| 5,180,732 | A | | 1/1993 | Tomioka et al. |
| 5,220,028 | A | | 6/1993 | Iwasawa et al. |
| 5,252,590 | A | | 10/1993 | Tomioka et al. |
| 5,556,866 | A | * | 9/1996 | Aga et al. ...................... 514/332 |
| 5,965,559 | A | | 10/1999 | Faull et al. |
| 6,106,849 | A | * | 8/2000 | Malkan et al. ................. 424/401 |
| 6,150,356 | A | | 11/2000 | Lloyd et al. |
| 6,172,005 | B1 | | 1/2001 | Selby |
| 6,265,588 | B1 | | 7/2001 | Müllner et al. |
| 6,313,127 | B1 | | 11/2001 | Waterson et al. |
| 6,511,977 | B1 | | 1/2003 | Lloyd et al. |
| 7,288,554 | B2 | | 10/2007 | Finkelstein et al. |
| 7,863,444 | B2 | | 1/2011 | Calderwood et al. |
| 2003/0158232 | A1 | | 8/2003 | Cheng et al. |
| 2003/0187001 | A1 | | 10/2003 | Calderwood et al. |
| 2004/0048283 | A1 | | 3/2004 | Pau et al. |
| 2004/0198979 | A1 | | 10/2004 | Dhanak et al. |
| 2004/0235755 | A1 | | 11/2004 | Eigenbrodt et al. |
| 2009/0054453 | A1 | | 2/2009 | Alcaraz et al. |
| 2010/0105657 | A1 | | 4/2010 | Nordvall et al. |
| 2011/0224252 | A1 | | 9/2011 | Dumeunier et al. |

FOREIGN PATENT DOCUMENTS

| | | | |
|---|---|---|---|
| DE | 19841985 | * | 3/2000 |
| EP | 0628551 A1 | | 12/1994 |
| GB | 1274436 | * | 6/1970 |
| WO | WO-97/28129 A1 | | 8/1997 |
| WO | WO-97/28141 A1 | | 8/1997 |
| WO | WO-99/16751 A1 | | 4/1999 |
| WO | WO 02/072077 | | 9/2002 |
| WO | WO 03/073999 | | 9/2003 |
| WO | WO-03/076422 A1 | | 9/2003 |
| WO | WO 2004/110375 | | 12/2004 |
| WO | WO 2005/072642 | * | 8/2005 |
| WO | WO 2005/117591 | | 12/2005 |
| WO | WO-2006/038594 A1 | | 4/2006 |
| WO | WO 2006/122546 | | 11/2006 |
| WO | WO-2008/050168 A1 | | 5/2008 |
| WO | WO 2009/025781 | | 2/2009 |
| WO | WO 2010/042867 | | 4/2010 |

OTHER PUBLICATIONS

Park, KS. "Prevention of type 2 diabetes mellitus from the viewpoint of genetics." Diabetes Research and Clinical Practice. 2004; 66S: S33-S35.*

Friedman et al. Leptin and the regulation of body weight in mammals. Nature. vol. 395, 1996.*

Shi et al. Silencing of pkm2 increases the efficacy of docetaxel in human lung cancer xenografts in mice. Cancer Sci. vol. 101, No. 6, Jun. 2010, 1447-1453.*

Remington's. pp. 420-425, 1980.*

DE 19841985. English translation. 2000.*

Ge et al. Anaplasma phagocytophilum inhibits human neutrophil apoptosis via upregulation of bfl-1, maintenance of mitochondrial membrane potential and prevention of caspase 3 activation. Cellular Microbiology, 2005, 7(1), 29-38.*

(Continued)

*Primary Examiner* — Anna Pagonakis

(74) *Attorney, Agent, or Firm* — Clark & Elbing LLP; Kristina Bieker-Brady

(57) ABSTRACT

The invention provides pharmaceutical compositions, kits, and methods of treating cancer, diabetes, obesity, autoimmune disease, and benign prostatic hyperplasia using compounds that selectively inhibit pyruvate kinase M2 and an assay measuring chemical modulation of pyruvate kinase activity.

1 Claim, 21 Drawing Sheets

(56) References Cited

OTHER PUBLICATIONS van der Ouderaa. Anti-plaque agents. Rationale and prospects for prevention of gingivitis and periodontal disease. (J. Clin. Periodontol. 1991; 18: 447-454).*
Nystrom et al. The long-term effect of a plaque control program on tooth mortality, caries and periodontal disease in adults. J. Clin. Periodontol. 2004; 31: 748-757.*
Eswaran et al., "Crystal Structures and Inhibitor Identification for PTPN5, PTPRR and PTPN7: A Family of Human MAPK-Specific Protein Tyrosine Phosphatases," *Biochem J*. 395: 483-491 (2006).
Kao et al., "A Small-Molecule Inhibitor of the Ribonucleolytic Activity of Human Angiogenin That Possesses Antitumor Activity," *Proc. Natl. Acad. Sci. USA*, 99(15): 10066-10071 (2002).
Lee, "Consolidation Effect of Phenylalanine-administration of Antitumor Activity of A 5 Fluorouracil," *Med. J. Kagoshima Univ*. 37(3-4): 285-308 (1985).
Vander Heiden et al., "Identification of Small Molecule Inhibitors of Pyruvate Kinase M2," *Biochemical Pharmacology*. 79(8): 1118-1124 (2010).
International Search Report and the Written Opinion of the International Search Authority (PCT/US07/17519), mailed Jul. 8, 2008.
European Patent Office Communication (European Application No. 07836571.5), dated Oct. 18, 2010.
International Preliminary Report on Patentability for International Application No. PCT/US2007/017519, issued Feb. 10, 2009.
OA from European Application No. 07836571.5, dated Sep. 18, 2012.
Behun et al., "The Chemistry of Pyrazine and Its Derivatives. IV. The Alkylation and Arylation of Methylpyrazine," *J. Org. Chem*. 26(9): 3379-3382, 1961.
Beger et. al., "Treatment of Pancreatic Cancer: Challenge of the Facts," *World J. Surg*. 27(10): 1075-1084, 2003.
Budinger et al., "Cellular energy utilization and supply during hypoxia in embryonic cardiac myocytes," *Am J Physiol*. 270(1 Pt 1): L44-53, 1996.
Cecil Textbook of Medicine, edited by Bennet, J.C., and Plum F., 1(20): 1004-1010, 1996.
Chabner et al., "Chemotherapy and the war on cancer," *Nature Rev. Cancer*, 5: 65-72, 2005.
Chan et al., "Synthesis and characterization of poly(amide sulfonamide)s (PASAs)," *J. Polymer. Sci*. 33(15): 2525-2531, 1995.
Christofk et al., "Pyruvate kinase M2 is a phosphotyrosine-binding protein," *Nature*. 452(7184): 181-186, 2008, and two pages of supplementary material.
Christofk et al., "The M2 splice isoform of pyruvate kinase is important for cancer metabolism and tumour growth," *Nature*. 452(7184): 230-233, 2008, and one page of supplementary material.
Clément et al., "Production of intracellular superoxide mediates dithiothreitol-dependent inhibition of apoptotic cell death," *Antioxid Redox Signal*. 7(3-4): 456-464, 2005.
Cohen, "The development and therapeutic potential of protein kinase inhibitors," *Curr Opin Chem Biol*. 3(4): 459-465, 1999.
Communication enclosing the Supplementary European Search Report and Written Opinion for European Patent No. 10794667.5, dated Jan. 1, 2013.
Communication enclosing the Supplementary Search Report and Written Opinion for European Patent Application No. 10794668.3, dated Oct. 10, 2012.
Cuzick et al., "Overview of the main outcomes in breast-cancer prevention trials," *Lancet*. 361(9354): 296-300, 2003.
Dermer, "Another anniversary for the war on cancer," *Bio/Technology* 12: 320, 1994.
Eigenbrodt et al., "Double role for pyruvate kinase type M2 in the expansion of phosphometabolite pools found in tumor cells," *Crit Rev Oncog*. 3(1-2): 91-115, 1992 (Abstract only).
Fabbro et al., "Protein kinases as targets for anticancer agents: from inhibitors to useful drugs," *Pharmacol Ther*. 93(2-3): 79-98, 2002.
Freshney et al.,Culture of Animal Cells, A Manual of Basic Technique, Alan R. Liss, Inc., 1983, New York, pp. 1-6 (see p. 4).

Golub et al., "Molecular classification of cancer: class discovery and class prediction by gene expression monitoring," *Science*. 286(5439): 531-537,1999.
Hulleman et al., "Pyruvate kinase M2 and prednisolone resistance in acute lymphoblastic leukemia," *Haematologica*. 94(9): 1322-1324, 2009.
International Preliminary Report on Patentability and Written Opinion for Application No. PCT/US2009/060237, issued Apr. 12, 2011.
International Search Report and Written Opinion for PCT/US2010/059778, mailed Mar. 17, 2011.
International Search Report for Application No. PCT/US2009/060237, mailed Jun. 16, 2010.
Jurica et al., "The allosteric regulation of pyruvate kinase by fructose-1, 6-bisphosphate," *Structure*. 6(2): 195-210, 1998.
Kharalkar et al., "Identification of novel allosteric regulators of human-erythrocyte pyruvate kinase," *Chem Biodivers*. 4(11): 2603-2617, 2007.
Klapars et al., "A general and efficient copper catalyst for the amidation of aryl halides and the N-arylation of nitrogen heterocycles," *J Am Chem Soc*. 123(31): 7727-7729, 2001.
Lee et al., "An efficient synthesis of 2,8-diazabicyclo[4.3.0]-nonane derivatives via intramolecular cyclization reaction," *Synth. Comm*. 25(23): 3741-3746, 1995.
Lee et al., "Pyruvate kinase isozyme type M2 (PKM2) interacts and cooperates with Oct-4 in regulating transcription," *Int J Biochem Cell Biol*. 40(5): 1043-1054, 2008.
Mass, "The HER receptor family: a rich target for therapeutic development," *Int J Radiat Oncol Biol Phys*. 58(3): 932-940, 2004.
Ôeda, "On some 2,5-Dialkyl-piperazines," *Bull. Chem. Soc*. 13(7): 465-470, 1938.
Paudler and Zeiler, "3,7-Disubstituted octahydro-1,5-diazocines. Their conversion into tetrahydro-1,5-diazocines and into ring-contracted products," *J Org Chem*. 32(8): 2425-2430, 1967.
Pollard and Gray, "Some amides of piperazines," *J Am Chem Soc*. 75(2): 491, 1953.
Pujol et al., "Is there a case for cisplatin in the treatment of small-cell lung cancer? A meta-analysis of randomized trials of a cisplatin-containing regimen versus a regimen without this alkylating agent," *Br J Cancer*. 83(1): 8-15, 2000.
Rich and Bigner, "Development of novel targeted therapies in the treatment of malignant glioma," *Nat Rev Drug Discov*. 3(5): 430-446, 2004.
Root et al., "Genome-scale loss-of-function screening with a lentiviral RNAi library," *Nat Methods* 3(9): 715-719, 2006.
Schneider et al., "Tumor M2-pyruvate kinase in the follow-up of inoperable lung cancer patients: a pilot study," *Cancer Lett*. 193(1): 91-98, 2003.
Schroth et al., "Ringschlußreaktion von Diacetylen mit Diaminen: Eine Einfache Synthese von 2,3-Dihydro-1,4-diazepinen," *Zeitschift Fur Chemie*. 6(4): 143, 1969 (English Translation of First Paragraph generated through Google Translator provided).
Seibel et al., "Synthesis and evaluation of δ-lactams (piperazones) as elastase inhibitors," *Bioorg Med Chem Lett*. 13(3): 387-389, 2003.
Stewart et al., "Piperazines. I. Derivatives of Piperazine-1-Carboxylic and -1,4-Dicarboxylic Acid," *J. Org. Chem*. 18(1): 1478-1483, 1953.
Surh, "Cancer chemoprevention with dietary phytochemicals," *Nat Rev Cancer* 3(10): 768-780, 2003.
Szoka and Papahadjopoulos, "Comparative properties and methods of preparation of lipid vesicles (liposomes)," *Annu Rev Biophys Bioeng*. 9: 467-508, 1980.
Uozumi et al., "Catalytic asymmetric construction of morpholines and piperazines by palladium-catalyzed tandem allylic substitution reactions," *J. Org. Chem*. 58(24): 6826-6832, 1993.
Yar et al., "An annulation reaction for the synthesis of morpholines, thiomorpholines, and piperazines from β-heteroatom amino compounds and vinyl sulfonium salts," *Angew Chem Int Ed* 47(20): 3784-3786, 2008.

* cited by examiner c h

Figure 3

Peptides for injection into rabbits for polyclonal Ab against PKM1 and PKM2 hM1: HLIAREAEAAM FHRKLFEELVRASSH STDLMEAMAMGSVEA SYKCLAAALIVLTESG hM2: HLIAREAEAAI YHIQLFEELRRLAPI TSDPTEATAVGAVEA SFKCCSGAIIVLTKSG

INHIBITORS OF PYRUVATE KINASE AND METHODS OF TREATING DISEASE

CROSS REFERENCE TO RELATED APPLICATIONS

This application is the U.S. National Stage of International Application No. PCT/US2007/017519, filed Aug. 6, 2007, which claims benefit of U.S. Provisional Patent Application No. 60/835,821, filed Aug. 4, 2006, which is hereby incorporated by reference.

STATEMENT AS TO FEDERALLY FUNDED RESEARCH

The United States Government has a paid-up license in this invention and the right in limited circumstances to require the patent owner to license others on reasonable terms as provided for by the terms of R01 GM56203 awarded by the National Institute of Health (NIH).

BACKGROUND OF THE INVENTION

The invention described herein features methods, compositions, and kits for the use of inhibitors of pyruvate kinase M2 (PKM2) to treat diseases related to pyruvate kinase function, including, e.g., cancer, diabetes, obesity, autoimmune disorders, and benign prostatic hyperplasia (BPH). The invention described herein also features a method for identifying inhibitors of PKM2.

Cancer cells rely primarily on glycolysis to generate cellular energy, while the majority of "normal" cells in adult tissues utilize aerobic respiration. This fundamental difference in cellular metabolism between cancer cells and normal cells, termed the Warburg Effect, has been exploited for diagnostic purposes, but has not yet been exploited for therapeutic benefit.

Pyruvate kinase (PK) is a metabolic enzyme that converts phosphoenolpyruvate to pyruvate during glycolysis. Four PK isoforms exist in mammals: the L and R isoforms are expressed in liver and red blood cells, the M1 isoform is expressed in most adult tissues, and the M2 isoform is a splice variant of M1 expressed during embryonic development. All tumor cells exclusively express the embryonic M2 isoform. A well-known difference between the M1 and M2 isoforms of PK is that M2 is a low-activity enzyme that relies on allosteric activation by the upstream glycolytic intermediate, fructose-1,6-bisphosphate (FBP), whereas M1 is a constitutively active enzyme.

All tumor cells exclusively express the embryonic M2 isoform of pyruvate kinase, suggesting PKM2 as a potential target for cancer therapy. PKM2 is also expressed in adipose tissue and activated T-cells. Thus, the inhibition of PKM2 may be effective in the treatment of, e.g., obesity, diabetes, autoimmune conditions, and proliferation-dependent diseases, e.g., benign prostatic hyperplasia (BPH). Current inhibitors of pyruvate kinase are not selective, making it difficult to treat disease related to pyruvate kinase function.

There is a need the art for novel treatments of disease, including, e.g., cancer, diabetes, obesity, autoimmune conditions, proliferation-dependent diseases (e.g., BPH), and other diseases related to the function of pyruvate kinase (e.g., PKM2).

SUMMARY OF THE INVENTION

The invention described herein features methods, compositions, and kits for the use of inhibitors of pyruvate kinase M2 in the treatment of diseases related to pyruvate kinase function. These inhibitors may be useful for the treatment of diseases related to the function of pyruvate kinase, including, e.g., cancer, diabetes, obesity, autoimmune diseases, and BPH. The invention described herein also features a method for identifying inhibitors of PKM2.

In one embodiment, the invention features a method of inhibiting pyruvate kinase M2 in a subject in need thereof by administering to the subject an effective amount of a compound of formula I:

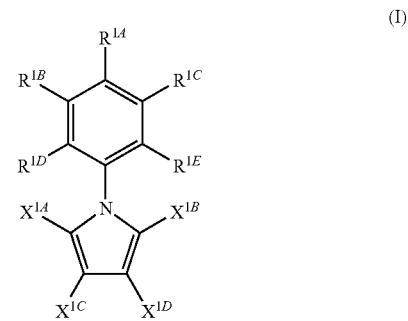

wherein each of $R^{1A}$, $R^{1B}$, $R^{1C}$, $R^{1D}$, $R^{1E}$, $X^{1A}$, $X^{1B}$, $X^{1C}$, and $X^{1D}$ is independently, selected from H, halide, nitro, $C_{1-4}$ alkyl, $C_{2-4}$ alkenyl, $C_{2-4}$ alkynyl, $OR^{1K}$, $OC(O)R^{1L}$, $NR^{1M}R^{1N}$, $NHC(O)R^{1O}$, $NHC(S)R^{1P}$, $NHC(O)OR^{1Q}$, $NHC(S)OR^{1R}$, $NHC(O)NHR^{1S}$, $NHC(S)NHR^{1T}$, $NHC(O)SR^{1U}$, $NHC(S)SR^{1V}$, $NHS(O)_2R^{1W}$, $C(O)OR^{1X}$, $C(O)NHR^{1Y}$, $(CH_2)_{1-4}OH$, $C(O)R^{1Z}$, $CH_2R^{1AA}$, $SO_3H$, $SO_2R^{1BB}$, $S(O)R^{1CC}$, $SR^{1DD}$, $SO_2NHR^{1EE}$, and $S(CH_2)_{1-4}C(O)OH$; and each of $R^{1K}$, $R^{1L}$, $R^{1M}$, $R^{1N}$, $R^{1O}$, $R^{1P}$, $R^{1Q}$, $R^{1R}$, $R^{1S}$, $R^{1T}$, $R^{1U}$, $R^{1V}$, $R^{1W}$, $R^{1X}$, $R^{1Y}$, $R^{1Z}$, $R^{1AA}$, $R^{1BB}$, $R^{1CC}$, $R^{1DD}$, and $R^{1EE}$ is, independently, selected from H, $C_{1-4}$ alkyl, $C_{2-4}$ alkenyl, $C_{2-4}$ alkynyl, $C_{2-6}$ heterocyclyl, $C_{6-12}$ aryl, $C_{7-14}$ alkaryl, $C_{3-10}$ alkheterocyclyl, and $C_{1-4}$ heteroalkyl, and salts thereof. In one particular embodiment, $X^{1A}$ and $X^{1B}$ are both methyl, $X^{1C}$ and $X^{1D}$ are both H, and each of $R^{1A}$, $R^{1B}$, $R^{1C}$, $R^{1D}$, and $R^{1E}$ is, independently, selected from H, halide, nitro, $C_{1-4}$ alkyl, $C_{2-4}$ alkenyl, $C_{2-4}$ alkynyl, $OR^{1K}$, $OC(O)R^{1L}$, $NR^{1M}R^{1N}$, $NHC(O)R^{1O}$, $NHC(S)R^{1P}$, $NHC(O)OR^{1Q}$, $NHC(S)OR^{1R}$, $NHC(O)NHR^{1S}$, $NHC(S)NHR^{1T}$, $NHC(O)SR^{1U}$, $NHC(S)SR^{1V}$, $NHS(O)_2R^{1W}$, $C(O)OR^{1X}$, $C(O)NHR^{1Y}$, $(CH_2)_{1-4}OH$, $C(O)R^{1Z}$, $CH_2R^{1AA}$, $SO_3H$, $SO_2R^{1BB}$, $S(O)R^{1CC}$, $SR^{1DD}$, $SO_2NHR^{1EE}$, and $S(CH_2)_{1-4}C(O)OH$; and each of $R^{1K}$, $R^{1L}$, $R^{1M}$, $R^{1N}$, $R^{1O}$, $R^{1P}$, $R^{1Q}$, $R^{1R}$, $R^{1S}$, $R^{1T}$, $R^{1U}$, $R^{1V}$, $R^{1W}$, $R^{1X}$, $R^{1Y}$, $R^{1Z}$, $R^{1AA}$, $R^{1BB}$, $R^{1CC}$, $R^{1DD}$, and $R^{1EE}$ is, independently, selected from H, $C_{1-4}$ alkyl, $C_{2-4}$ alkenyl, $C_{2-4}$ alkynyl, $C_{2-6}$ heterocyclyl, $C_{6-12}$ aryl, $C_{7-14}$ alkaryl, $C_{3-10}$ alkheterocyclyl, and $C_{1-4}$ heteroalkyl, and salts thereof.

This method may be used to treat, e.g., diabetes (e.g., type I or type II), obesity, autoimmune diseases, or proliferative diseases (e.g., BPH).

The invention further features a pharmaceutical composition containing a compound of formula I.

The invention also features a pharmaceutical composition that includes a compound of formula II:

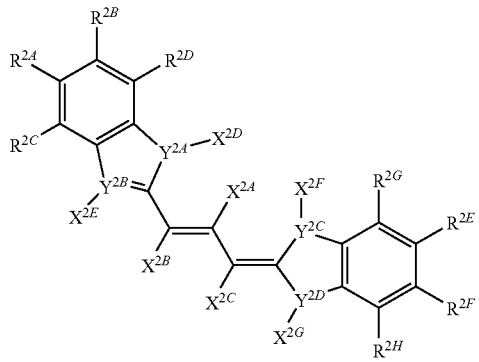

(II)

wherein each of $X^{2A}$, $X^{2B}$, $X^{2C}$, $X^{2D}$, $X^{2E}$, $X^{2F}$, and $X^{2G}$ is, independently, selected from H, $C_{1-8}$ alkyl, $C_{2-4}$ alkenyl, $C_{2-4}$ alkynyl, $C_{2-6}$ heterocyclyl, $C_{6-12}$ aryl, $C_{7-14}$ alkaryl, $C_{3-10}$ alkheterocyclyl, and $C_{1-8}$ heteroalkyl; and each of $Y^{2A}$, $Y^{2C}$, and $Y^{2D}$ is, independently, selected from N and CH; and $Y^{2B}$ is, independently, selected from N+ and C; and each of $R^{2A}$, $R^{2B}$, $R^{2C}$, $R^{2D}$, $R^{2E}$, $R^{2F}$, $R^{2G}$, and $R^{2H}$ is, independently, selected from H, halide, nitro, $C_{1-4}$ alkyl, $C_{2-4}$ alkenyl, $C_{2-4}$ alkynyl, $OR^{2K}$, $OC(O)R^{2L}$, $NR^{2M}R^{2N}$, $NHC(O)R^{2O}$, $NHC(S)R^{2P}$, $NHC(O)OR^{2Q}$, $NHC(S)OR^{2R}$, $NHC(O)NHR^{2S}$, $NHC(S)NHR^{2T}$, $NHC(O)SR^{2U}$, $NHC(S)SR^{2V}$, $NHS(O)_2R^{2W}$, $C(O)OR^{2X}$, $C(O)NHR^{2Y}$, $(CH_2)_{1-4}OH$, $C(O)R^{2Z}$, $CH_2R^{2AA}$, $SO_3H$, $SO_2R^{2BB}$, $S(O)R^{2CC}$, $SR^{2DD}$, $SO_2NHR^{2EE}$, and $S(CH_2)_{1-4}C(O)OH$; and each of $R^{2K}$, $R^{2L}$, $R^{2M}$, $R^{2N}$, $R^{2O}$, $R^{2P}$, $R^{2Q}$, $R^{2R}$, $R^{2S}$, $R^{2T}$, $R^{2U}$, $R^{2V}$, $R^{2W}$, $R^{2X}$, $R^{2Y}$, $R^{2Z}$, $R^{2AA}$, $R^{2BB}$, $R^{2CC}$, $R^{2DD}$, and $R^{2EE}$ is, independently, selected from H, $C_{1-4}$ alkyl, $C_{2-4}$ alkenyl, $C_{2-4}$ alkynyl, $C_{2-6}$ heterocyclyl, $C_{6-12}$ aryl, $C_{7-14}$ alkaryl, $C_{3-10}$ alkheterocyclyl, and $C_{1-4}$ heteroalkyl, and salts thereof. In one particular embodiment, each of $X^{2A}$, $X^{2B}$, $X^{2C}$, $R^{2C}$, $R^{2D}$, $R^{2G}$, and $R^{2H}$ is H; and each of $Y^{2A}$, $Y^{2C}$, and $Y^{2D}$ is N; and $Y^{2B}$ is N+; and each of $X^{2D}$, $X^{2E}$, $X^{2F}$, and $X^{2G}$ is, independently, selected from H, $C_{1-8}$ alkyl, $C_{2-4}$ alkenyl, $C_{2-4}$ alkynyl, and $C_{1-8}$ heteroalkyl; and each of $R^{2A}$, $R^{2B}$, $R^{2E}$, and $R^{2F}$ is, independently, selected from H, halide, nitro, $C_{1-4}$ alkyl, $C_{2-4}$ alkenyl, $C_{2-4}$ alkynyl, $OR^{2K}$, $OC(O)R^{2L}$, $NR^{2M}R^{2N}$, $NHC(O)R^{2O}$, $NHC(S)R^{2P}$, $NHC(O)OR^{2Q}$, $NHC(S)OR^{2R}$, $NHC(O)NHR^{2S}$, $NHC(S)NHR^{2T}$, $NHC(O)SR^{2U}$, $NHC(S)SR^{2V}$, $NHS(O)_2R^{2W}$, $C(O)OR^{2X}$, $C(O)NHR^{2Y}$, $(CH_2)_{1-4}OH$, $C(O)R^{2Z}$, $CH_2R^{2AA}$, $SO_3H$, $SO_2R^{2BB}$, $S(O)R^{2CC}$, $SR^{2DD}$, $SO_2NHR^{2EE}$, and $S(CH_2)_{1-4}C(O)OH$; and each of $R^{2K}$, $R^{2L}$, $R^{2M}$, $R^{2N}$, $R^{2O}$, $R^{2P}$, $R^{2Q}$, $R^{2R}$, $R^{2S}$, $R^{2T}$, $R^{2U}$, $R^{2V}$, $R^{2W}$, $R^{2X}$, $R^{2Y}$, $R^{2Z}$, $R^{2AA}$, $R^{2BB}$, $R^{2CC}$, $R^{2DD}$, and $R^{2EE}$ is, independently, selected from H and $C_{1-4}$ alkyl, and salts thereof.

In another embodiment, the invention features a kit including: (i) a pharmaceutical composition containing a compound of formula II and (ii) instructions for administering the compound for the treatment of, e.g., cancer, obesity, diabetes, autoimmune diseases, or proliferative diseases (e.g., BPH).

In an alternate embodiment, the invention features a method of inhibiting pyruvate kinase M2 in a subject in need thereof by administering to the subject an effective amount of a compound of formula II. The method may be used for the treatment of cancer (e.g., breast, prostate, lung, bronchial, colon, rectal, kidney, renal, skin, pelvic, pancreatic, oral, ovarian, head, neck, thyroid, parathyroid, stomach, gastrointestinal, intestinal (e.g., small and large), brain, esophageal, liver, gallbladder, pleura, intrahepatic bile duct, cervix, testicular, ureter, anal, larynx, pharynx, bone, joint, vulvar, eye, and urinary bladder cancers, non-Hodgkin's lymphoma, Hodgkin's lymphoma, melanomas, carcinomas, basal cell carcinomas, neuroblastomas, multiple myelomas, leukemias, acute myeloid leukemias, chronic lymphocytic leukemias, soft tissue (e.g., heart) cancers, gastro-intestinal stoma tumors, chronic myeloid leukemias, acute lymphocytic leukemias, malignant mesotheliomas, retinoblastomas, acute tumors, or soft tissue sarcomas). The method may also be used to treat, e.g., diabetes (e.g., type I or type II), obesity, autoimmune diseases, or proliferative diseases (e.g., BPH).

The invention also features a pharmaceutical composition that includes a compound of formula III:

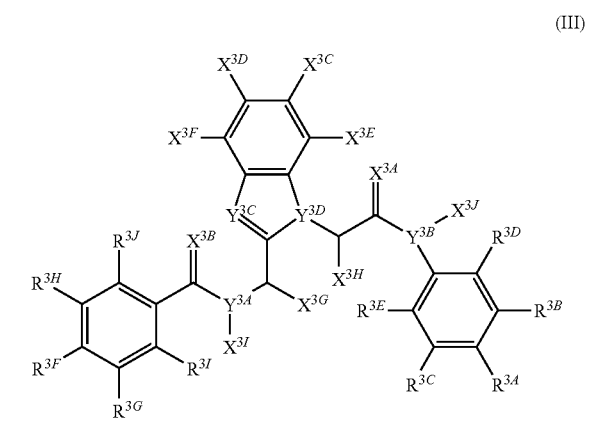

(III)

wherein each of $X^{3A}$ and $X^{3B}$ is, independently, selected from S, O, NH, and $CH_2$; and each of $X^{3G}$ and $X^{3H}$ is, independently, selected from H, $C_{1-8}$ alkyl, $C_{2-4}$ alkenyl, $C_{2-4}$ alkynyl, and $C_{1-8}$ heteroalkyl; and each of $Y^{3A}$ and $Y^{3B}$ is, independently, selected from O, CH, N, and S; and $X^{3I}$ is empty when $Y^{3A}$ is S or O, $X^{3J}$ is empty when $Y^{3B}$ is S or O, otherwise each of $X^{3I}$ and $X^{3J}$ is, independently, selected from H, $C_{1-8}$ alkyl, $C_{2-4}$ alkenyl, $C_{2-4}$ alkynyl, and $C_{1-8}$ heteroalkyl; and each of $Y^{3C}$ and $Y^{3D}$ is, independently, selected from CH and N; and each of $R^{3A}$, $R^{3B}$, $R^{3C}$, $R^{3D}$, $R^{3E}$, $R^{3F}$, $R^{3G}$, $R^{3H}$, $R^{3I}$, $R^{3J}$, $X^{3C}$, $X^{3D}$, $X^{3E}$, and $X^{3F}$ is, independently, selected from H, halide, nitro, $C_{1-4}$ alkyl, $C_{2-4}$ alkenyl, $C_{2-4}$ alkynyl, $OR^{3K}$, $OC(O)R^{3L}$, $NR^{3M}R^{3N}$, $NHC(O)R^{3O}$, $NHC(S)R^{3P}$, $NHC(O)OR^{3Q}$, $NHC(S)OR^{3R}$, $NHC(O)NHR^{3S}$, $NHC(S)NHR^{3T}$, $NHC(O)SR^{3U}$, $NHC(S)SR^{3V}$, $NHS(O)_2R^{3W}$, $C(O)OR^{3X}$, $C(O)NHR^{3Y}$, $(CH_2)_{1-4}OH$, $C(O)R^{3Z}$, $CH_2R^{3AA}$, $SO_3H$, $SO_2R^{3BB}$, $S(O)R^{3CC}$, $SR^{3DD}$, $SO_2NHR^{3EE}$, and $S(CH_2)_{1-4}C(O)OH$; and each of $R^{3K}$, $R^{3L}$, $R^{3M}$, $R^{3N}$, $R^{3O}$, $R^{3P}$, $R^{3Q}$, $R^{3R}$, $R^{3S}$, $R^{3T}$, $R^{3U}$, $R^{3V}$, $R^{3W}$, $R^{3X}$, $R^{3Y}$, $R^{3Z}$, $R^{3AA}$, $R^{3BB}$, $R^{3CC}$, $R^{3DD}$, and $R^{3EE}$ is, independently, selected from H, $C_{1-4}$ alkyl, $C_{2-4}$ alkenyl, $C_{2-4}$ alkynyl, $C_{2-6}$ heterocyclyl, $C_{6-12}$ aryl, $C_{7-14}$ alkaryl, $C_{3-10}$ alkheterocyclyl, and $C_{1-4}$ heteroalkyl, and salts thereof. In one particular embodiment, each of $X^{3A}$ and $X^{3B}$ is, independently, selected from S and O; and each of $X^{3G}$, $X^{3H}$, $X^{3I}$, and $X^{3J}$ is H; and each of $Y^{3A}$, $Y^{3B}$, $Y^{3C}$, and $Y^{3D}$ is, independently, selected from CH and N; and each of $R^{3A}$, $R^{3B}$, $R^{3C}$, $R^{3D}$, $R^{3E}$, $R^{3F}$, $R^{3G}$, $R^{3H}$, $R^{3I}$, $R^{3J}$, $X^{3C}$, $X^{3D}$, $X^{3E}$, and $X^{3F}$ is, independently, selected from H, halide, nitro, $C_{1-4}$ alkyl, $C_{2-4}$ alkenyl, $C_{2-4}$ alkynyl, $OR^{3K}$, $OC(O)R^{3L}$, $NR^{3M}R^{3N}$, $NHC(O)R^{3O}$, $NHC(S)R^{3P}$, $NHC(O)OR^{3Q}$, $NHC(S)OR^{3R}$, $NHC(O)NHR^{3S}$, $NHC(S)NHR^{3T}$, $NHC(O)SR^{3U}$, $NHC(S)SR^{3V}$, $NHS(O)_2R^{3W}$, $C(O)OR^{3X}$, $C(O)NHR^{3Y}$, $(CH_2)_{1-4}OH$, $C(O)R^{3Z}$, $CH_2R^{3AA}$, $SO_3H$, $SO_2R^{3BB}$, $S(O)R^{3CC}$, $SR^{3DD}$, $SO_2NHR^{3EE}$, and $S(CH_2)_{1-4}C(O)OH$; and each of $R^{3K}$, $R^{3L}$, $R^{3M}$, $R^{3N}$, $R^{3O}$, $R^{3P}$, $R^{3Q}$, $R^{3R}$, $R^{3S}$, $R^{3T}$, $R^{3U}$, $R^{3V}$, $R^{3W}$, $R^{3X}$, $R^{3Y}$, $R^{3Z}$, $R^{3AA}$, $R^{3BB}$, $R^{3CC}$, $R^{3DD}$, and $R^{3EE}$ is, independently, selected from H and $C_{1-4}$ alkyl, and salts thereof.

In another embodiment, the invention features a kit including: (i) a pharmaceutical composition containing a compound of formula III and (ii) instructions for administering the compound for the treatment of, e.g., cancer, obesity, diabetes, autoimmune diseases, or proliferative diseases (e.g., BPH).

In an alternate embodiment, the invention features a method of inhibiting pyruvate kinase M2 in a subject in need thereof by administering to the subject an effective amount of a compound of formula III. The method may be used for the treatment of cancer (e.g., breast, prostate, lung, bronchial, colon, rectal, kidney, renal, skin, pelvic, pancreatic, oral, ovarian, head, neck, thyroid, parathyroid, stomach, gastrointestinal, intestinal (e.g., small and large), brain, esophageal, liver, gallbladder, pleura, intrahepatic bile duct, cervix, testicular, ureter, anal, larynx, pharynx, bone, joint, vulvar, eye, and urinary bladder cancers, non-Hodgkin's lymphoma, Hodgkin's lymphoma, melanomas, carcinomas, basal cell carcinomas, neuroblastomas, multiple myelomas, leukemias, acute myeloid leukemias, chronic lymphocytic leukemias, soft tissue (e.g., heart) cancers, gastro-intestinal stromal tumors, chronic myeloid leukemias, acute lymphocytic leukemias, malignant mesotheliomas, retinoblastomas, acute tumors, or soft tissue sarcomas). The method may also be used to treat, e.g., diabetes (e.g., type I or type II), obesity, autoimmune diseases, or proliferative diseases (e.g., BPH).

The invention also features a pharmaceutical composition that includes a compound of formula IV:

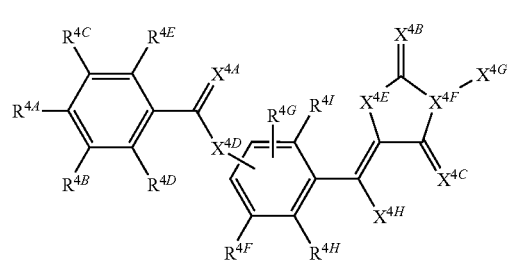

(IV)

wherein each of $X^{4A}$, $X^{4B}$, and $X^{4C}$ is, independently, selected from S, O, NH, $CH_2$, and two hydrogen atoms; and each of $X^{4G}$ and $X^{4H}$ is, independently, selected from H, $C_{1-8}$ alkyl, $C_{2-8}$ alkenyl, $C_{2-8}$ alkynyl, and $C_{1-8}$ heteroalkyl; and each of $X^{4D}$ and $X^{4E}$ is, independently, selected from O, $CH_2$, NH, and S; and $X^{4F}$ is, independently, selected from CH and N; and each of $R^{4A}$, $R^{4B}$, $R^{4C}$, $R^{4D}$, $R^{4E}$, $R^{4F}$, $R^{4G}$, $R^{4H}$, and $R^{4I}$, is, independently, selected from H, halide, nitro, $C_{1-4}$ alkyl, $C_{2-4}$ alkenyl, $C_{2-4}$ alkynyl, $OR^{4K}$, $OC(O)R^{4L}$, $NR^{4M}R^{4N}$, $NHC(O)R^{4O}$, $NHC(S)R^{4P}$, $NHC(O)OR^{4Q}$, $NHC(S)OR^{4R}$, $NHC(O)NHR^{4S}$, $NHC(S)NHR^{4T}$, $NHC(O)SR^{4U}$, $NHC(S)SR^{4V}$, $NHS(O)_2R^{4W}$, $C(O)OR^{4X}$, $C(O)NHR^{4Y}$, $(CH_2)_{1-4}OH$, $C(O)R^{4Z}$, $CH_2R^{4AA}$, $SO_3H$, $SO_2R^{4BB}$, $S(O)R^{4CC}$, $SR^{4DD}$, $SO_2NHR^{4EE}$, and $S(CH_2)_{1-4}C(O)OH$; and each of $R^{4K}$, $R^{4L}$, $R^{4M}$, $R^{4N}$, $R^{4O}$, $R^{4P}$, $R^{4Q}$, $R^{4R}$, $R^{4S}$, $R^{4T}$, $R^{4U}$, $R^{4V}$, $R^{4W}$, $R^{4X}$, $R^{4Y}$, $R^{4Z}$, $R^{4AA}$, $R^{4BB}$, $R^{4CC}$, $R^{4DD}$, and $R^{4EE}$ is, independently, selected from H, $C_{1-4}$ alkyl, $C_{2-4}$ alkenyl, $C_{2-4}$ alkynyl, $C_{2-6}$ heterocyclyl, $C_{6-12}$ aryl, $C_{7-44}$ alkaryl, $C_{3-10}$ alkheterocyclyl, and $C_{1-4}$ heteroalkyl, and salts thereof. In one particular embodiment, each of $X^{4A}$, $X^{4B}$, and $X^{4C}$ is, independently, selected from S, O, and two hydrogen atoms; and $X^{4G}$ is, independently, selected from H, $C_{1-8}$ alkyl, and $C_{1-8}$ heteroalkyl; and $X^{4H}$ is H; and each of $X^{4D}$ and $X^{4E}$ is, independently, selected from O, $CH_2$, NH, and S; and $X^{4F}$ is, independently, selected from CH and N; and each of $R^{4A}$, $R^{4B}$, $R^{4C}$, $R^{4D}$, $R^{4E}$, $R^{4F}$, $R^{4G}$, $R^{4H}$, and $R^{4I}$, is, independently, selected from H, halide, nitro, $C_{1-4}$ alkyl, $C_{2-4}$ alkenyl, $C_{2-4}$ alkynyl, $OR^{4K}$, $OC(O)R^{4L}$, $NR^{4M}R^{4N}$, $NHC(O)R^{4O}$, $NHC(S)R^{4P}$, $NHC(O)OR^{4Q}$, $NHC(S)OR^{4R}$, $NHC(O)NHR^{4S}$, $NHC(S)NHR^{4T}$, $NHC(O)SR^{4U}$, $NHC(S)SR^{4V}$, $NHS(O)_2R^{4W}$, $C(O)OR^{4X}$, $C(O)NHR^{4Y}$, $(CH_2)_{1-4}OH$, $C(O)R^{4Z}$, $CH_2R^{4AA}$, $SO_3H$, $SO_2R^{4BB}$, $S(O)R^{4CC}$, $SR^{4DD}$, $SO_2NHR^{4EE}$, and $S(CH_2)_{1-4}C(O)OH$; and each of $R^{4K}$, $R^{4L}$, $R^{4M}$, $R^{4N}$, $R^{4O}$, $R^{4P}$, $R^{4Q}$, $R^{4R}$, $R^{4S}$, $R^{4T}$, $R^{4U}$, $R^{4V}$, $R^{4W}$, $R^{4X}$, $R^{4Y}$, $R^{4Z}$, $R^{4AA}$, $R^{4BB}$, $R^{4CC}$, $R^{4DD}$, and $R^{4EE}$ is, independently, selected from H and $C_{1-4}$ alkyl, and salts thereof.

In another embodiment, the invention features a kit including: (i) a pharmaceutical composition containing a compound of formula IV and (ii) instructions for administering the compound for the treatment of e.g., cancer, obesity, diabetes, autoimmune diseases, or proliferative diseases (e.g., BPH).

In an alternate embodiment, the invention features a method of inhibiting pyruvate kinase M2 in a subject in need thereof by administering to the subject an effective amount of a compound of formula IV. The method may be used for the treatment of cancer (e.g., breast, prostate, lung, bronchial, colon, rectal, kidney, renal, skin, pelvic, pancreatic, oral, ovarian, head, neck, thyroid, parathyroid, stomach, gastrointestinal, intestinal (e.g., small and large), brain, esophageal, liver, gallbladder, pleura, intrahepatic bile duct, cervix, testicular, ureter, anal, larynx, pharynx, bone, joint, vulvar, eye, and urinary bladder cancers, non-Hodgkin's lymphoma, Hodgkin's lymphoma, melanomas, carcinomas, basal cell carcinomas, neuroblastomas, multiple myelomas, leukemias, acute myeloid leukemias, chronic lymphocytic leukemias, soft tissue (e.g., heart) cancers, gastro-intestinal stromal tumors, chronic myeloid leukemias, acute lymphocytic leukemias, malignant mesotheliomas, retinoblastomas, acute tumors, or soft tissue sarcomas). The method may also be used to treat, e.g., diabetes (e.g., type I or type II), obesity, autoimmune diseases, or proliferative diseases (e.g., BPH).

The invention further features a pharmaceutical composition that includes a compound of formula V:

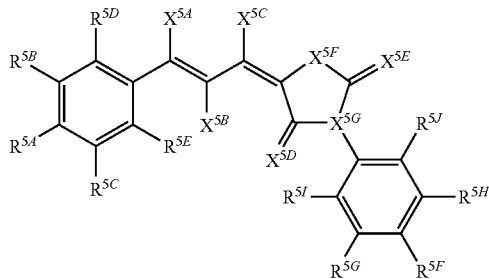

(V)

wherein each of $X^{5A}$, $X^{5B}$, and $X^{5C}$ is, independently, selected from H, $C_{1-8}$ alkyl, $C_{2-4}$ alkenyl, $C_{2-4}$ alkynyl, and $C_{1-8}$ heteroalkyl; and each of $X^{5D}$ and $X^{5E}$ is, independently, selected from S, NH, O, and $CH_2$; and $X^{5F}$ is, independently, selected from O, NH, $CH_2$, and S; and $X^{5G}$ is, independently, selected from CH and N; and each of $R^{5A}$, $R^{5B}$, $R^{5C}$, $R^{5D}$, $R^{5E}$, $R^{5F}$, $R^{5G}$, $R^{5H}$, $R^{5I}$, and $R^{5J}$, is, independently, selected from H, halide, nitro, $C_{1-4}$ alkyl, $C_{2-4}$ alkenyl, $C_{2-4}$ alkynyl, $OR^{5K}$, $OC(O)R^{5L}$, $NR^{5M}R^{5N}$, $NHC(O)R^{5O}$, $NHC(S)R^{5P}$, $NHC(O)OR^{5Q}$, $NHC(S)OR^{5R}$, $NHC(O)NHR^{5S}$, $NHC(S)NHR^{5T}$, NHC(O)SR$^{5U}$, NHC(S)SR$^{5V}$, NHS(O)$_2$R$^{5W}$, C(O)OR$^{5X}$, C(O)NHR$^{5Y}$, (CH$_2$)$_{1-4}$OH, C(O)R$^{5Z}$, CH$_2$R$^{5AA}$, SO$_3$H, SO$_2$R$^{5BB}$, S(O)R$^{5CC}$, SR$^{5DD}$, SO$_2$NHR$^{5EE}$, and S(CH$_2$)$_{1-4}$C(O)OH; and each of R$^{5K}$, R$^{5L}$, R$^{5M}$, R$^{5N}$, R$^{5O}$, R$^{5P}$, R$^{5Q}$, R$^{5R}$, R$^{5S}$, R$^{5T}$, R$^{5U}$, R$^{5V}$, R$^{5W}$, R$^{5X}$, R$^{5Y}$, R$^{5Z}$, R$^{5AA}$, R$^{5BB}$, R$^{5CC}$, R$^{5DD}$, and R$^{5EE}$ is, independently, selected from H, C$_{1-4}$ alkyl, C$_{2-4}$ alkenyl, C$_{2-4}$ alkynyl, C$_{2-6}$ heterocyclyl, C$_{6-12}$ aryl, C$_{7-14}$ alkaryl, C$_{3-10}$ alkheterocyclyl, and C$_{1-4}$ heteroalkyl, and salts thereof. In one particular embodiment, each of X$^{5A}$, X$^{5B}$, and X$^{5C}$ is H; and each of X$^{5D}$ and X$^{5E}$ is, independently, selected from S and O; and X$^{5F}$ is, independently, selected from O, NH, CH$_2$, and S; and X$^{5G}$ is, independently, selected from CH and N; and each of R$^{5A}$, R$^{5B}$, R$^{5C}$, R$^{5D}$, R$^{5E}$, R$^{5F}$, R$^{5G}$, R$^{5H}$, R$^{5I}$ and R$^{5J}$, is, independently, selected from H, halide, nitro, C$_{1-4}$ alkyl, C$_{2-4}$ alkenyl, C$_{2-4}$ alkynyl, OR$^{5K}$, OC(O)R$^{5L}$, NR$^{5M}$R$^{5N}$, NHC(O)R$^{5O}$, NHC(S)R$^{5P}$, NHC(O)OR$^{5Q}$, NHC(S)OR$^{5R}$, NHC(O)NHR$^{5S}$, NHC(S)NHR$^{5T}$, NHC(O)SR$^{5U}$, NHC(S)SR$^{5V}$, NHS(O)$_2$R$^{5W}$, C(O)OR$^{5X}$, C(O)NHR$^{5Y}$, (CH$_2$)$_{1-4}$OH, C(O)R$^{5Z}$, CH$_2$R$^{5AA}$, SO$_3$H, SO$_2$R$^{5BB}$, S(O)R$^{5CC}$, SR$^{5DD}$, SO$_2$NHR$^{5EE}$, and S(CH$_2$)$_{1-4}$C(O)OH; and each of R$^{5K}$, R$^{5L}$, R$^{5M}$, R$^{5N}$, R$^{5O}$, R$^{5P}$, R$^{5Q}$, R$^{5R}$, R$^{5S}$, R$^{5T}$, R$^{5U}$, R$^{5V}$, R$^{5W}$, R$^{5X}$, R$^{5Y}$, R$^{5Z}$, R$^{5AA}$, R$^{5BB}$, R$^{5CC}$, R$^{5DD}$, and R$^{5EE}$ is, independently, selected from H and C$_{1-4}$ alkyl, and salts thereof.

In another embodiment, the invention features a kit including: (i) a pharmaceutical composition containing a compound of formula V and (ii) instructions for administering the compound for the treatment of, e.g., cancer, obesity, diabetes, autoimmune diseases, or proliferative diseases (e.g., BPH).

In an alternate embodiment, the invention features a method of inhibiting pyruvate kinase M2 in a subject in need thereof by administering to the subject an effective amount of a compound of formula V. The method may be used for the treatment of cancer (e.g., breast, prostate, lung, bronchial, colon, rectal, kidney, renal, skin, pelvic, pancreatic, oral, ovarian, head, neck, thyroid, parathyroid, stomach, gastrointestinal, intestinal (e.g., small and large), brain, esophageal, liver, gallbladder, pleura, intrahepatic bile duct, cervix, testicular, ureter, anal, larynx, pharynx, bone, joint, vulvar, eye, and urinary bladder cancers, non-Hodgkin's lymphoma, Hodgkin's lymphoma, melanomas, carcinomas, basal cell carcinomas, neuroblastomas, multiple myelomas, leukemias, acute myeloid leukemias, chronic lymphocytic leukemias, soft tissue (e.g., heart) cancers, gastro-intestinal stromal tumors, chronic myeloid leukemias, acute lymphocytic leukemias, malignant mesotheliomas, retinoblastomas, acute tumors, or soft tissue sarcomas). The method may also be used to treat, e.g., diabetes (e.g., type I or type II), obesity, autoimmune diseases, or proliferative diseases (e.g., BPH).

The invention further features a pharmaceutical composition including a compound of formula VI:

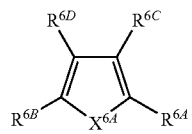

(VI)

wherein X$^{6A}$ is, independently, selected from S, NH, and O; and each of R$^{6A}$, R$^{6B}$, R$^{6C}$, and R$^{6D}$, is, independently, selected from H, halide, nitro, C$_{1-4}$ alkyl, C$_{2-4}$ alkenyl, C$_{2-4}$ alkynyl, OR$^{6K}$, OC(O)R$^{6L}$, NR$^{6M}$R$^{6N}$, NHC(O)R$^{6O}$, NHC(S)R$^{6P}$, NHC(O)OR$^{6Q}$, NHC(S)OR$^{6R}$, NHC(O)NHR$^{6S}$, NHC(S)NHR$^{6T}$, NHC(O)SR$^{6U}$, NHC(S)SR$^{6V}$, NHS(O)$_2$R$^{6W}$, C(O)OR$^{6X}$, C(O)NHR$^{6Y}$, (CH$_2$)$_{1-4}$OH, C(O)R$^{6Z}$, CH$_2$R$^{6AA}$, SO$_3$H, SO$_2$R$^{6BB}$, S(O)R$^{6CC}$, SR$^{6DD}$, SO$_2$NHR$^{6EE}$, and S(CH$_2$)$_{1-4}$C(O)OH; and each of R$^{6K}$, R$^{6L}$, R$^{6M}$, R$^{6N}$, R$^{6O}$, R$^{6P}$, R$^{6Q}$, R$^{6R}$, R$^{6S}$, R$^{6T}$, R$^{6U}$, R$^{6V}$, R$^{6W}$, R$^{6X}$, R$^{6Y}$, R$^{6Z}$, R$^{6AA}$, R$^{6BB}$, R$^{6CC}$, R$^{6DD}$, and R$^{6EE}$ is, independently, selected from H, C$_{1-4}$ alkyl, C$_{2-4}$ alkenyl, C$_{2-4}$ alkynyl, C$_{2-6}$ heterocyclyl, C$_{6-12}$ aryl, C$_{7-14}$ alkaryl, C$_{3-10}$ alkheterocyclyl, and C$_{1-4}$ heteroalkyl, and salts thereof. In one particular embodiment, X$^{6A}$ is, independently, selected from S and O; and each of R$^{6C}$ and R$^{6D}$ is H; and each of R$^{6A}$ and R$^{6B}$, is, independently, selected from H, halide, nitro, C$_{1-4}$ alkyl, C$_{2-4}$ alkenyl, C$_{2-4}$ alkynyl, OR$^{6K}$, OC(O)R$^{6L}$, NR$^{6M}$R$^{6N}$, NHC(O)R$^{6O}$, NHC(S)R$^{6P}$, NHC(O)OR$^{6Q}$, NHC(S)OR$^{6R}$, NHC(O)NHR$^{6S}$, NHC(S)NHR$^{6T}$, NHC(O)SR$^{6U}$, NHC(S)SR$^{6V}$, NHS(O)$_2$R$^{6W}$, C(O)OR$^{6X}$, C(O)NHR$^{6Y}$, (CH$_2$)$_{1-4}$OH, C(O)R$^{6Z}$, CH$_2$R$^{6AA}$, SO$_3$H, SO$_2$R$^{6BB}$, S(O)R$^{6CC}$, SR$^{6DD}$, SO$_2$NHR$^{6EE}$, and S(C$_2$)$_{1-4}$C(O)OH; and each of R$^{6K}$, R$^{6L}$, R$^{6M}$, R$^{6N}$, R$^{6O}$, R$^{6P}$, R$^{6Q}$, R$^{6R}$, R$^{6S}$, R$^{6T}$, R$^{6U}$, R$^{6V}$, R$^{6W}$, R$^{6X}$, R$^{6Y}$, R$^{6Z}$, R$^{6AA}$, R$^{6BB}$, R$^{6CC}$, R$^{6DD}$, and R$^{6EE}$ is, independently, selected from H and C$_{1-4}$ alkyl, and salts thereof.

In another embodiment, the invention features a kit including: (i) a pharmaceutical composition containing a compound of formula VI and (ii) instructions for administering the compound for the treatment of, e.g., cancer, obesity, diabetes, autoimmune diseases, or proliferative diseases (e.g., BPH).

In an alternate embodiment, the invention features a method of inhibiting pyruvate kinase M2 in a subject in need thereof by administering to the subject an effective amount of a compound of formula VI. The method may be used for the treatment of cancer (e.g., breast, prostate, lung, bronchial, colon, rectal, kidney, renal, skin, pelvic, pancreatic, oral, ovarian, head, neck, thyroid, parathyroid, stomach, gastrointestinal, intestinal (e.g., small and large), brain, esophageal, liver, gallbladder, pleura, intrahepatic bile duct, cervix, testicular, ureter, anal, larynx, pharynx, bone, joint, vulvar, eye, and urinary bladder cancers, non-Hodgkin's lymphoma, Hodgkin's lymphoma, melanomas, carcinomas, basal cell carcinomas, neuroblastomas, multiple myelomas, leukemias, acute myeloid leukemias, chronic lymphocytic leukemias, soft tissue (e.g., heart) cancers, gastro-intestinal stromal tumors, chronic myeloid leukemias, acute lymphocytic leukemias, malignant mesotheliomas, retinoblastomas, acute tumors, or soft tissue sarcomas). The method may also be used to treat, e.g., diabetes (e.g., type I or type II), obesity, autoimmune diseases, or proliferative diseases (e.g., BPH).

The invention also features a pharmaceutical composition that includes a compound of formula VII:

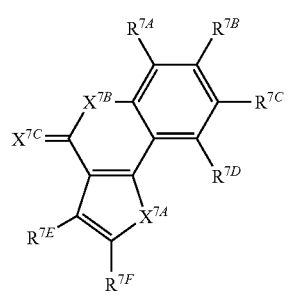

(VII)

wherein each of X$^{7A}$ and X$^{7B}$ is, independently, selected from S, NH, and O; and X$^{7C}$ is, independently, selected from S, NH, CH$_2$, and O; and each of R$^{7A}$, R$^{7B}$, R$^{7C}$, R$^{7D}$, R$^{7E}$, and R$^{7F}$ is, independently, selected from H, halide, nitro, C$_{1-4}$ alkyl, C$_{2-4}$ alkenyl, C$_{2-4}$ alkynyl, OR$^{7K}$, OC(O)R$^{7L}$, $NR^{7M}R^{7N}$, $NHC(O)R^{7O}$, $NHC(S)R^{7P}$, $NHC(O)OR^{7Q}$, $NHC(S)OR^{7R}$, $NHC(O)NHR^{7S}$, $NHC(S)NHR^{7T}$, $NHC(O)SR^{7U}$, $NHC(S)SR^{7V}$, $NHS(O)_2R^{7W}$, $C(O)OR^{7X}$, $C(O)NHR^{7Y}$, $(CH_2)_{1-4}OH$, $C(O)R^{7Z}$, $CH_2R^{7AA}$, $SO_3H$, $SO_2R^{7BB}$, $S(O)R^{7CC}$, $SR^{7DD}$, $SO_2NHR^{7EE}$, and $S(CH_2)_{1-4}C(O)OH$; and each of $R^{7K}$, $R^{7L}$, $R^{7M}$, $R^{7N}$, $R^{7O}$, $R^{7P}$, $R^{7Q}$, $R^{7R}$, $R^{7S}$, $R^{7T}$, $R^{7U}$, $R^{7V}$, $R^{7W}$, $R^{7X}$, $R^{7Y}$, $R^{7Z}$, $R^{7AA}$, $R^{7BB}$, $R^{7CC}$, $R^{7DD}$, and $R^{7EE}$ is, independently, selected from H, $C_{1-4}$ alkyl, $C_{2-4}$ alkenyl, $C_{2-4}$ alkynyl, $C_{2-6}$ heterocyclyl, $C_{6-12}$ aryl, $C_{7-14}$ alkaryl, $C_{3-10}$ alkheterocyclyl, and $C_{1-4}$ heteroalkyl, and salts thereof. In one particular embodiment, each of $X^{7A}$ and $X^{7B}$ is, independently, selected from S, NH, and O; and $X^{7C}$ is, independently, selected from S, NH, $CH_2$, and O; and each of $R^{7A}$, $R^{7B}$, $R^{7C}$, $R^{7D}$, and $R^{7E}$ is, independently, selected from H, halide, nitro, $C_{1-4}$ alkyl, $C_{2-4}$ alkenyl, $C_{2-4}$ alkynyl, $OR^{7K}$, $OC(O)R^{7L}$, $NR^{7M}R^{7N}$, $NHC(O)R^{7O}$, $NHC(S)R^{7P}$, $NHC(O)OR^{7Q}$, $NHC(S)OR^{7R}$, $NHC(O)NHR^{7S}$, $NHC(S)NHR^{7T}$, $NHC(O)SR^{7U}$, $NHC(S)SR^{7V}$, $NHS(O)_2R^{7W}$, $C(O)OR^{7X}$, $C(O)NHR^{7Y}$, $(CH_2)_{1-4}OH$, $C(O)R^{7Z}$, $CH_2R^{7AA}$, $SO_3H$, $SO_2R^{7BB}$, $S(O)R^{7CC}$, $SR^{7DD}$, $SO_2NHR^{7EE}$, and $S(CH_2)_{1-4}C(O)OH$; and each of $R^{7K}$, $R^{7L}$, $R^{7M}$, $R^{7N}$, $R^{7O}$, $R^{7P}$, $R^{7Q}$, $R^{7R}$, $R^{7S}$, $R^{7T}$, $R^{7U}$, $R^{7V}$, $R^{7W}$, $R^{7X}$, $R^{7Y}$, $R^{7Z}$, $R^{7AA}$, $R^{7BB}$, $R^{7CC}$, $R^{7DD}$, and $R^{7EE}$ is, independently, selected from H and $C_{1-4}$ alkyl; and $R^{7F}$ is, independently, selected from $OC(O)R^{7FF}$, $NHC(O)R^{7FF}$, $NHC(S)R^{7FF}$, $NHC(O)OR^{7FF}$, $NHC(S)OR^{7FF}$, $NHC(O)NHR^{7FF}$, $NHC(S)NHR^{7FF}$, $NHC(O)SR^{7FF}$, $NHC(S)SR^{7FF}$, $NHS(O)_2R^{7FF}$, $C(O)OR^{7FF}$, $C(O)NHR^{7FF}$, $C(O)R^{7FF}$, $SO_2R^{7FF}$, $S(O)R^{7FF}$, and $SO_2NHR^{7FF}$, where $R^{7FF}$ is selected from H and $C_{1-4}$ alkyl, and salts thereof.

In another embodiment, the invention features a kit including: (i) a pharmaceutical composition containing a compound of formula VII and (ii) instructions for administering the compound for the treatment of, e.g., cancer, obesity, diabetes, autoimmune diseases, or proliferative diseases (e.g., BPH).

In an alternate embodiment, the invention features a method of inhibiting pyruvate kinase M2 in a subject in need thereof by administering to the subject an effective amount of a compound of formula VII. The method may be used for the treatment of cancer (e.g., breast, prostate, lung, bronchial, colon, rectal, kidney, renal, skin, pelvic, pancreatic, oral, ovarian, head, neck, thyroid, parathyroid, stomach, gastrointestinal, intestinal (e.g., small and large), brain, esophageal, liver, gallbladder, pleura, intrahepatic bile duct, cervix, testicular, ureter, anal, larynx, pharynx, bone, joint, vulvar, eye, and urinary bladder cancers, non-Hodgkin's lymphoma, Hodgkin's lymphoma, melanomas, carcinomas, basal cell carcinomas, neuroblastomas, multiple myelomas, leukemias, acute myeloid leukemias, chronic lymphocytic leukemias, soft tissue (e.g., heart) cancers, gastro-intestinal stromal tumors, chronic myeloid leukemias, acute lymphocytic leukemias, malignant mesotheliomas, retinoblastomas, acute tumors, or soft tissue sarcomas). The method may also be used to treat, e.g., diabetes (e.g., type I or type II), obesity, autoimmune diseases, or proliferative diseases (e.g., BPH).

The invention also features a pharmaceutical composition that includes a compound of formula VIII:

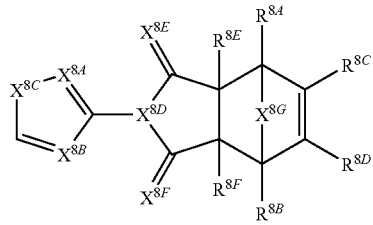

(VIII)

wherein $X^{8C}$ is, independently, selected from NH, CH=CH, or N=CH, and each of $X^{8A}$, $X^{8B}$, and $X^{8D}$ is, independently, selected from CH and N; and each of $X^{8E}$, $X^{8F}$ and $X^{8G}$ is, independently, selected from S, NH, $CH_2$, and O; and each of $R^{8A}$, $R^{8B}$, $R^{8C}$, $R^{8D}$, $R^{8E}$, and $R^{8F}$ is, independently, selected from H, $C_{1-4}$ alkyl, $C_{2-4}$ alkenyl, $C_{2-4}$ alkynyl, $C_{2-6}$ heterocyclyl, $C_{6-12}$ aryl, $C_{7-14}$ alkaryl, $C_{3-10}$ alkheterocyclyl, and $C_{1-4}$ heteroalkyl, and salts thereof. In one particular embodiment, $X^{8C}$ is, independently, selected from NH, CH=CH, or N=CH; and each of $X^{8A}$, $X^{8B}$, and $X^{8D}$ is, independently, selected from CH and N; and each of $X^{8E}$ and $X^{8F}$ is, independently, selected from S and O; $X^{8G}$ is $CH_2$; and each of $R^{8A}$, $R^{8B}$, $R^{8C}$, $R^{8D}$, $R^{8E}$, and $R^{8F}$ is, independently, selected from H and $C_{1-4}$ alkyl, and salts thereof.

In another embodiment, the invention features a kit including: (i) a pharmaceutical composition containing a compound of formula VIII and (ii) instructions for administering the compound for the treatment of, e.g., cancer, obesity, diabetes, autoimmune diseases, or proliferative diseases (e.g., BPH).

In an alternate embodiment, the invention features a method of inhibiting pyruvate kinase M2 in a subject in need thereof by administering to the subject an effective amount of a compound of formula VIII. The method may be used for the treatment of cancer (e.g., breast, prostate, lung, bronchial, colon, rectal, kidney, renal, skin, pelvic, pancreatic, oral, ovarian, head, neck, thyroid, parathyroid, stomach, gastrointestinal, intestinal (e.g., small and large), brain, esophageal, liver, gallbladder, pleura, intrahepatic bile duct, cervix, testicular, ureter, anal, larynx, pharynx, bone, joint, vulvar, eye, and urinary bladder cancers, non-Hodgkin's lymphoma, Hodgkin's lymphoma, melanomas, carcinomas, basal cell carcinomas, neuroblastomas, multiple myelomas, leukemias, acute myeloid leukemias, chronic lymphocytic leukemias, soft tissue (e.g., heart) cancers, gastro-intestinal stromal tumors, chronic myeloid leukemias, acute lymphocytic leukemias, malignant mesotheliomas, retinoblastomas, acute tumors, or soft tissue sarcomas). The method may also be used to treat, e.g., diabetes (e.g., type I or type II), obesity, autoimmune diseases, or proliferative diseases (e.g., BPH).

The invention also features a method for identifying inhibitors of pyruvate kinase activity. This method includes combining pyruvate kinase and phosphoenolpyruvate in a solution, activating said pyruvate kinase by adding fructose-1,6-bisphosphate (FBP) to the solution, contacting the solution with a molecule of interest, quantifying the amount of a substrate present in the solution, and determining whether the molecule inhibits the activity of pyruvate kinase. The pyruvate kinase may be, e.g., the M1 or M2 isoform. The solution may further be contacted with lactate dehydrogenase. The substrate quantified in the solution may be, e.g., ATP or NADH. The quantification of the substrate may be completed using, e.g., absorbance, fluorescence, Raman scattering, phosphorescence, luminescence, luciferase activity, or radioactivity. The method may further include the additional step of comparing the inhibition of the activity of the M1 and M2 isoforms of pyruvate kinase.

The invention also features a method for treating cancer in a subject in need thereof by administering an effective amount of an inhibitor that is selective for the M2 isoform of pyruvate kinase. The method may be used for the treatment of cancer (e.g., breast, prostate, lung, bronchial, colon, rectal, kidney, renal, skin, pelvic, pancreatic, oral, ovarian, head, neck, thyroid, parathyroid, stomach, gastrointestinal, intestinal (e.g., small and large), brain, esophageal, liver, gallbladder, pleura, intrahepatic bile duct, cervix, testicular, ureter, anal, larynx, pharynx, bone, joint, vulvar, eye, and urinary bladder cancers, non-Hodgkin's lymphoma, Hodgkin's lymphoma, melanomas, carcinomas, basal cell carcinomas, neuroblastomas, multiple myelomas, leukemias, acute myeloid leukemias, chronic lymphocytic leukemias, soft tissue (e.g., heart) cancers, gastro-intestinal stromal tumors, chronic myeloid leukemias, acute lymphocytic leukemias, malignant mesotheliomas, retinoblastomas, acute tumors, or soft tissue sarcomas). The invention also features methods for treating, e.g., diabetes (e.g., type I or type II), obesity, autoimmune diseases, or proliferative diseases (e.g., BPH) in a subject in need thereof by administering an effective amount of an inhibitor that is selective for the M2 isoform of pyruvate kinase.

By "effective amount" is meant the amount of a pharmaceutical composition of the invention required to treat or prevent a disease, such as, e.g., cancer, diabetes, obesity, autoimmune diseases, and proliferation-dependent diseases, such as BPH. The effective amount of a pharmaceutical composition of the invention used for therapeutic or prophylactic treatment varies depending upon the manner of administration, the age, body weight, and general health of the subject. Ultimately, the attending prescriber will decide the appropriate amount and dosage regimen. Such an amount is referred to as the "effective amount."

By "selective" is meant at least 2-fold, 3-fold, 4-fold, 5-fold, 6-fold, or 10-fold greater inhibition of M2 than M1 under the conditions set forth in Example 4.

By "pharmaceutical composition" is meant a composition containing a compound of the invention (i.e., a compound of any of formulas (I)-(VIII)), formulated with a pharmaceutically acceptable excipient, and manufactured or sold in conformity with the rules of a governmental regulatory agency as part of a therapeutic regimen for the treatment or prevention of disease in a mammal. Pharmaceutical compositions can be formulated, for example, for oral administration in unit dosage form (e.g., a tablet, capsule, caplet, gelcap, or syrup), for topical administration (e.g., as a cream, gel, lotion, or ointment), for intravenous administration (e.g., as a sterile solution free of particulate emboli and in a solvent system suitable for intravenous use), or for any other formulation described herein.

Compounds useful in the pharmaceutical compositions of the invention may include those described herein in any of their pharmaceutically acceptable forms, including isomers such as diastereomers and enantiomers, salts, solvates, prodrugs, and polymorphs, thereof, as well as racemic mixtures of the compounds described herein.

By "prodrug" is meant a molecule that, upon metabolism in the body of a subject, is chemically converted to another molecule serving a therapeutic or other pharmaceutical purpose (e.g., a drug molecule containing a carboxylic acid contains an amide or an ester bond in its prodrug form, which is cleaved upon metabolism).

By "treating" is meant administering a pharmaceutical composition for prophylactic and/or therapeutic purposes. To "prevent disease" refers to prophylactic treatment of a subject who is not yet ill, but who is susceptible to, or otherwise at risk of, a particular disease. To "treat disease" or use for "therapeutic" treatment refers to administering treatment to a subject already suffering from a disease to improve or stabilize the subject's condition.

By "Tanimoto coefficient" is meant a measure of chemical similarity between two compounds indicating the fraction of common substructures held between them. The invention features eleven lead compounds and their structural homologues for use in treating various diseases related to pyruvate kinase function, such as, e.g., cancer. A compound is identified as a structural homologue of a lead compound if it has a significant number of substructures in common with that lead compound, such that the Tanimoto coefficient measuring structural similarity between those two compounds has a value of 0.85 or greater (on a scale of 0 to 1). The Tanimoto coefficient between two compounds is determined by calculating the ratio of the number of substructures held in common by the two compounds to the number of total substructures present in at least one of the two compounds. Tanimoto coefficients can also be calculated using hashed binary fingerprints wherein each fingerprint encodes the substructure composition of one compound and the Tanimoto coefficient is the ratio of the number of bits set to "1" in both compounds' fingerprints divided by the number of bits set to "1" in either compound's fingerprint using methods known in the art (see, e.g., Patterson et al., *J. Med. Chem.* 39:3049-59, 1996; Matter et al., *J. Med. Chem.* 40:1219-29, 1997; Potter et al., *J. Med. Chem.* 41:478-88, 1998; Taylor et al., *J. Chem. Inf. Comp. Sci.* 35:59-67, 1995; and Delaney et al., *Mol. Diversity* 1:217-22, 1996). In the present invention, one such method using Daylight fingerprints is used to calculate Tanimoto coefficients and thus identify compounds present in publicly available chemical databases (e.g., PubChem and Chembank) that are structural homologues of a lead compound (see, e.g., Martin et al., *J. Med. Chem.* 45:4350-8, 2002; Daylight Chemical Information Systems Inc., Irvine, Calif.). A lead compound and structurally homologous compound having a Tanimoto coefficient of 0.85 or greater as calculated using Daylight fingerprints are known to have a probability of 30% or greater (e.g., 50% or 75%) of having the same biological activity, depending in part on the potency of the lead compound, e.g., having an IC50 less than 10 micromolar or having an IC50 between 10 micromolar and 100 micromolar, and in part on the biological activity under consideration, as known in the art (see, e.g., Martin et al., *J. Med. Chem.* 45:4350-8, 2002; and Klekota et al., *J. Chem. Info. Model.* 45:1824-36, 2005).

In the generic descriptions of compounds of this invention, the number of atoms of a particular type in a substituent group is generally given as a range, e.g., an alkyl group containing from 1 to 4 carbon atoms or $C_{1-4}$ alkyl. Reference to such a range is intended to include specific references to groups having each of the integer number of atoms within the specified range. For example, an alkyl group from 1 to 4 carbon atoms includes each of $C_1$, $C_2$, $C_3$, and $C_4$. A $C_{1-4}$ heteroalkyl, for example, includes from 1 to 3 carbon atoms in addition to one or more heteroatoms. Other numbers of atoms and other types of atoms may be indicated in a similar manner.

As used herein, the terms "alkyl" and the prefix "alk-" are inclusive of both straight chain and branched chain groups and of cyclic groups, i.e., cycloalkyl. Exemplary cyclic groups include cyclopropyl, cyclobutyl, cyclopentyl, and cyclohexyl groups. A "$C_{1-4}$ alkyl" group has from 1 to 4 carbon atoms. A "$C_{1-8}$ alkyl" group has from 1 to 8 carbon atoms. Alkyl groups, e.g., a $C_{1-4}$ alkyl group or a $C_{1-8}$ alkyl group, may be substituted or unsubstituted. Exemplary substituents include alkoxy, aryloxy, sulfhydryl, alkylthio, arylthio, halide, hydroxyl, fluoroalkyl, perfluoralkyl, amino, aminoalkyl, disubstituted amino, quaternary amino, hydroxyalkyl, carboxyalkyl, and carboxyl groups. $C_{1-4}$ alkyls and $C_{1-8}$ alkyls include, without limitation, methyl; ethyl; n-propyl; isopropyl; cyclopropyl; cyclopropylmethyl; cyclopropylethyl; n-butyl; iso-butyl; sec-butyl; tert-butyl; and cyclobutyl.

By "alkenyl" is meant a branched or unbranched hydrocarbon group containing one or more double bonds. A "$C_{2-4}$ alkenyl" group has from 2 to 4 carbon atoms. Alkenyl, e.g., a $C_{2-4}$ alkenyl group, may be substituted or unsubstituted. Exemplary substituents include alkoxy, aryloxy, sulfhydryl, alkylthio, arylthio, halide, hydroxyl, fluoroalkyl, perfluoralkyl, amino, aminoalkyl, disubstituted amino, quaternary amino, hydroxyalkyl, carboxyalkyl, and carboxyl groups. $C_{2-4}$ alkenyls include, without limitation, vinyl; allyl; 2-cyclopropyl-1-ethenyl; 1-propenyl; 1-butenyl; 2-butenyl; 3-butenyl; 2-methyl-1-propenyl; and 2-methyl-2-propenyl.

By "alkynyl" is meant a branched or unbranched hydrocarbon group containing one or more triple bonds. A "$C_{2-4}$ alkynyl" group has from 2 to 4 carbon atoms. Alkynl, e.g., a $C_{2-4}$ alkynyl group, may be substituted or unsubstituted. Exemplary substituents include alkoxy, aryloxy, sulfhydryl, alkylthio, arylthio, halide, hydroxy, fluoroalkyl, perfluoralkyl, amino, aminoalkyl, disubstituted amino, quaternary amino, hydroxyalkyl, carboxyalkyl, and carboxyl groups. $C_{2-4}$ alkynyls include, without limitation, ethynyl, 1-propynyl, 2-propynyl, 1-butynyl, 2-butynyl, and 3-butynyl.

By "$C_{2-6}$ heterocyclyl" is meant a stable 5- to 7-membered monocyclic or 7- to 14-membered bicyclic heterocyclic ring which is saturated, partially unsaturated, or unsaturated (aromatic), and which consists of 2 to 6 carbon atoms and 1, 2, 3 or 4 heteroatoms independently selected from the group consisting of N, O, and S and including any bicyclic group in which any of the above-defined heterocyclic rings is fused to a benzene ring. The heterocyclyl group may be substituted or unsubstituted. Exemplary substituents include alkoxy, aryloxy, sulfhydryl, alkylthio, arylthio, halide, hydroxy, fluoroalkyl, perfluoralkyl, amino, aminoalkyl, disubstituted amino, quaternary amino, hydroxyalkyl, carboxyalkyl, and carboxyl groups. The nitrogen and sulfur heteroatoms may optionally be oxidized. The heterocyclic ring may be covalently attached via any heteroatom or carbon atom that results in a stable structure, e.g., an imidazolinyl ring may be linked at either of the ring-carbon atom positions or at the nitrogen atom. A nitrogen atom in the heterocycle may optionally be quaternized. Preferably when the total number of S and O atoms in the heterocycle exceeds 1, then these heteroatoms are not adjacent to one another. Heterocycles include, without limitation, 1H-indazole, 2-pyrrolidonyl, 2H,6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4aH-carbazolyl, b-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, xanthenyl. Preferred 5 to 10 membered heterocycles include, but are not limited to, pyridinyl, pyrimidinyl, triazinyl, furanyl, thienyl, thiazolyl, pyrrolyl, pyrazolyl, imidazolyl, oxazolyl, isoxazolyl, tetrazolyl, benzofuranyl, benzothiofuranyl, indolyl, benzimidazolyl, 1H-indazolyl, oxazolidinyl, isoxazolidinyl, benzotriazolyl, benzisoxazolyl, oxindolyl, benzoxazolinyl, quinolinyl, and isoquinolinyl. Preferred 5 to 6 membered heterocycles include, without limitation, pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, and tetrazolyl.

By "aryl" is meant an aromatic group having a ring system comprised of carbon atoms with conjugated π electrons (e.g., phenyl). The "$C_{6-12}$ aryl" group has from 6 to 12 carbon atoms. Aryl groups, e.g., $C_{6-12}$ aryl groups, may optionally include monocyclic, bicyclic, or tricyclic rings, in which each ring desirably has five or six members. The aryl group, e.g., $C_{6-12}$ aryl groups, may be substituted or unsubstituted. Exemplary substituents include alkyl, hydroxy, alkoxy, aryloxy, sulfhydryl, alkylthio, arylthio, halide, fluoroalkyl, carboxyl, hydroxyalkyl, carboxyalkyl, amino, aminoalkyl, monosubstituted amino, disubstituted amino, and quaternary amino groups.

By "$C_{7-14}$ alkaryl" is meant an alkyl substituted by an aryl group (e.g., benzyl, phenethyl, or 3,4-dichlorophenethyl) having from 7 to 14 carbon atoms.

By "$C_{3-10}$ alkheterocyclyl" is meant an alkyl substituted heterocyclic group having from 7 to 14 carbon atoms in addition to one or more heteroatoms, independently selected from the group consisting of N, O, S, and P, (e.g., 3-furanylmethyl, 2-furanylmethyl, 3-tetrahydrofuranylmethyl, or 2-tetrahydrofuranylmethyl).

By "$C_{1-4}$ heteroalkyl" is meant a branched or unbranched alkyl, alkenyl, or alkynyl group having from 1 to 4 carbon atoms in addition to 1, 2, or 3 heteroatoms independently selected from the group consisting of N, O, S, and P. By "$C_{1-8}$ heteroalkyl" is meant a branched or unbranched alkyl, alkenyl, or alkynyl group having from 1 to 8 carbon atoms in addition to 1, 2, or 3 heteroatoms independently selected from the group consisting of N, O, S, and P. Heteroalkyls include, without limitation, tertiary amines, secondary amines, ethers, thioethers, amides, thioamides, carbamates, thiocarbamates, hydrazones, imines, phosphodiesters, phosphoramidates, sulfonamides, and disulfides. A heteroalkyl may optionally include monocyclic, bicyclic, or tricyclic rings, in which each ring desirably has three to six members. The heteroalkyl group may be substituted or unsubstituted. Exemplary substituents include alkoxy, aryloxy, sulfhydryl, sulfate, alkylthio, arylthio, halide, hydroxyl, fluoroalkyl, perfluoralkyl, amino, aminoalkyl, disubstituted amino, quaternary amino, hydroxyalkyl, hydroxyalkyl, carboxyalkyl, and carboxyl groups.

By "acyl" is meant a chemical moiety with the formula R—C(O)—, wherein R is selected from $C_{1-4}$ alkyl, $C_{2-4}$ alkenyl, $C_{2-4}$ alkynyl, $C_{2-6}$ heterocyclyl, $C_{6-12}$ aryl, $C_{7-14}$ alkaryl, $C_{3-10}$ alkheterocyclyl, or $C_{1-4}$ heteroalkyl.

By "halide" is meant bromine, chlorine, iodine, or fluorine.

By "fluoroalkyl" is meant an alkyl group that is substituted with a fluorine.

By "perfluoroalkyl" is meant an alkyl group consisting of only carbon and fluorine atoms.

By "carboxyalkyl" is meant a chemical moiety with the formula —(R)—COOH, wherein R is selected from $C_{1-4}$ alkyl, $C_{2-4}$ alkenyl, $C_{2-4}$ alkynyl, $C_{2-6}$ heterocyclyl, $C_{6-12}$ aryl, $C_{7-14}$ alkaryl, $C_{3-10}$ alkheterocyclyl, or $C_{1-4}$ heteroalkyl.

By "hydroxyalkyl" is meant a chemical moiety with the formula —(R)—OH, wherein R is selected from $C_{1-4}$ alkyl, $C_{2-4}$ alkenyl, $C_{2-4}$ alkynyl, $C_{2-6}$ heterocyclyl, $C_{6-12}$ aryl, $C_{7-14}$ alkaryl, $C_{3-10}$ alkheterocyclyl, or $C_{1-4}$ heteroalkyl.

By "alkoxy" is meant a chemical substituent of the formula —OR, wherein R is selected from $C_{1-4}$ alkyl, $C_{2-4}$ alkenyl, $C_{2-4}$ alkynyl, $C_{2-6}$ heterocyclyl, $C_{6-12}$ aryl, $C_{7-14}$ alkaryl, $C_{3-10}$ alkheterocyclyl, or $C_{1-4}$ heteroalkyl.

By "aryloxy" is meant a chemical substituent of the formula —OR, wherein R is a $C_{6-12}$ aryl group.

By "alkylthio" is meant a chemical substituent of the formula —SR, wherein R is selected from $C_{1-4}$ alkyl, $C_{2-4}$ alkenyl, $C_{2-4}$ alkynyl, $C_{2-6}$ heterocyclyl, $C_{6-12}$ aryl, $C_{7-14}$ alkaryl, $C_{3-10}$ alkheterocyclyl, or $C_{1-4}$ heteroalkyl.

By "arylthio" is meant a chemical substituent of the formula —SR, wherein R is a $C_{6-12}$ aryl group.

By "quaternary amino" is meant a chemical substituent of the formula —(R)—N(R')(R'')(R''')$^+$, wherein R, R', R'', and R''' are each independently an alkyl, alkenyl, alkynyl, or aryl group. R may be an alkyl group linking the quaternary amino nitrogen atom, as a substituent, to another moiety. The nitrogen atom, N, is covalently attached to four carbon atoms of alkyl and/or aryl groups, resulting in a positive charge at the nitrogen atom.

Other features and advantages of the invention will be apparent from the following Detailed Description, the drawings, and the claims.

BRIEF DESCRIPTION OF THE DRAWINGS

FIG. 3 shows the peptide sequences used to raise antibodies specific for PKM1 and PKM2.

FIG. 4a is an immunoblot of mammary gland protein lysates from MMTV-neu mice before (N) and after (T) tumor development. T1-T4 represent lysates from tumors that developed in four different mice. Proteins from total cell extracts were immunoblotted for PKM1, PKM2, and actin. FIG. 4b shows an immunoblot of protein lysates from cell lines. A549 and H1299 are lung carcinoma cell lines; 293T is a transformed embryonic kidney cell line; HeLa is a cervical carcinoma cell line; and MCF-10a is an immortalized breast epithelial cell line. Mouse muscle lysate was included as a control for M1 antibody staining. Total cell extracts were probed with antibodies towards PKM1, PKM2, and GAPDH (control).

FIG. 6a shows tumor formation over time in nude mice injected with M1 and M2 rescue H1299 cells. After 43 days, 3/7 mice injected with M1 cells and 7/8 mice injected with M2 cells formed tumors. FIG. 6b shows mice injected with M1 cells on the left flank and M2 cells on the right flank. Mouse (i) only formed a tumor from the M2 cells. Mouse (ii) formed a larger tumor from the M2 cells than from the M1 cells. FIG. 6c shows dissected tumors from nude mice. The only three tumors derived from M1 cells are shown (top row), and these tumors were smaller than four of the tumors from the M2 cells (bottom row). FIG. 6d shows the mass of the dissected tumors. Each dot represents the tumor mass from one mouse. The blue line indicates the mean tumor mass originating from M1 cells and M2 cells. FIG. 6e is an immunoblot of tumor lysates originating from M1 cells, M2 cells, or a 50/50 mixture of M1 and M2 cells (M1/M2). The left panel shows lysates from the injected cells. The right panel shows lysates from the dissected tumors. Lysates were immunoblotted with antibodies towards M1, M2, pyruvate kinase (recognizes both M1 and M2), flag, and GAPDH.

FIG. 7a shows the enzyme activity of recombinant PKM2 measured in the presence or absence of fructose-1,6-bisphosphate (FBP). FIG. 7b shows the enzyme activity of recombinant PKM1 measured in the presence or absence FBP. FIG. 7c shows that the amount of PKM2 added to the reaction was decreased to increase reaction time and facilitate screening. The enzyme activity of recombinant PKM2 was measured in the presence or absence of increasing concentrations of compound B1. FIG. 7d shows the enzyme activity of recombinant PKM1 measured in the presence or absence of increasing concentrations of compound B1.

DETAILED DESCRIPTION

Figure 1:
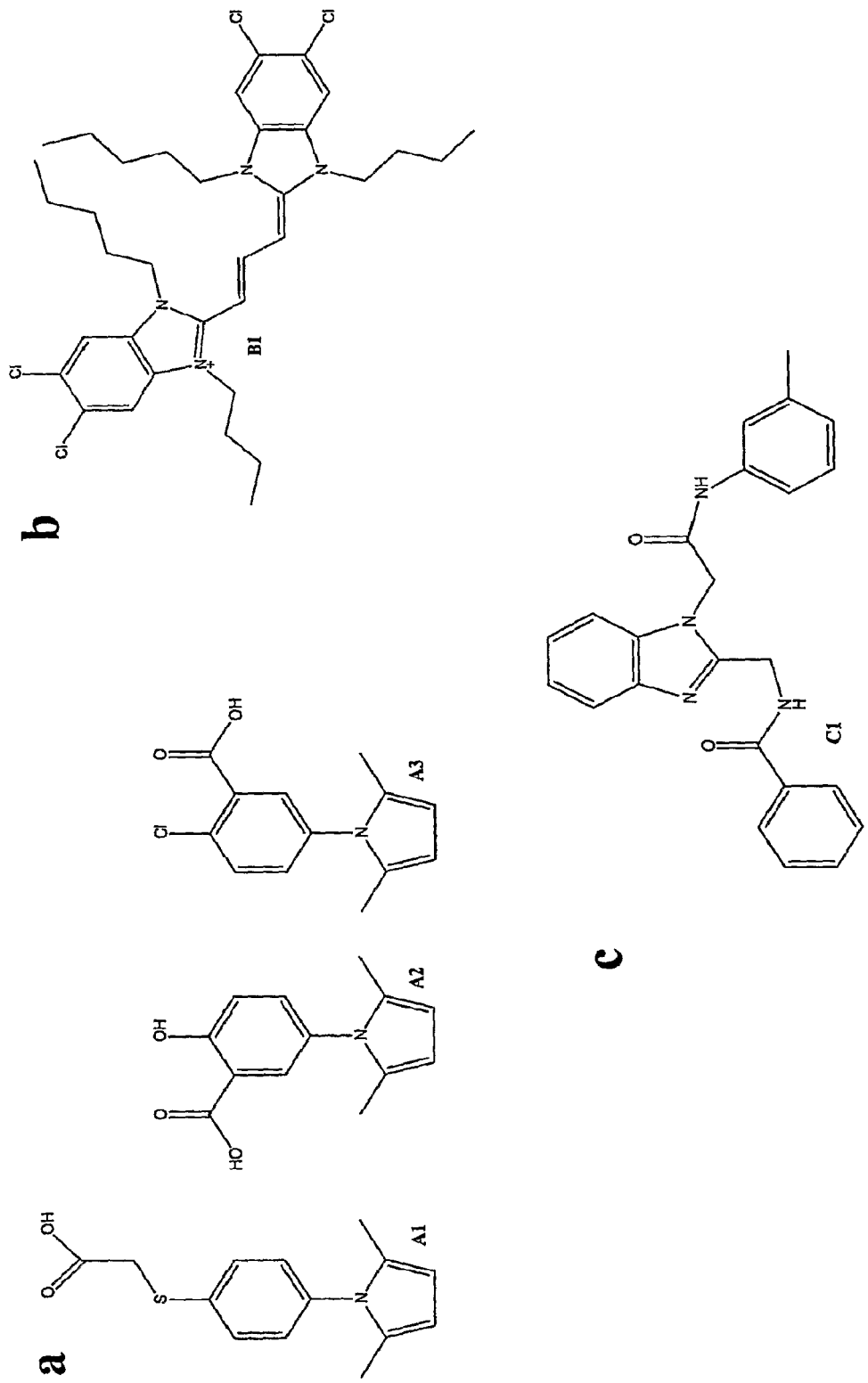
FIG. 1 shows eleven example compounds belonging to the eight different chemical families, identified in the screen described herein, that inhibit PKM2 activity, inhibit glycolysis, and inhibit cancer cell growth.
Figure 1:
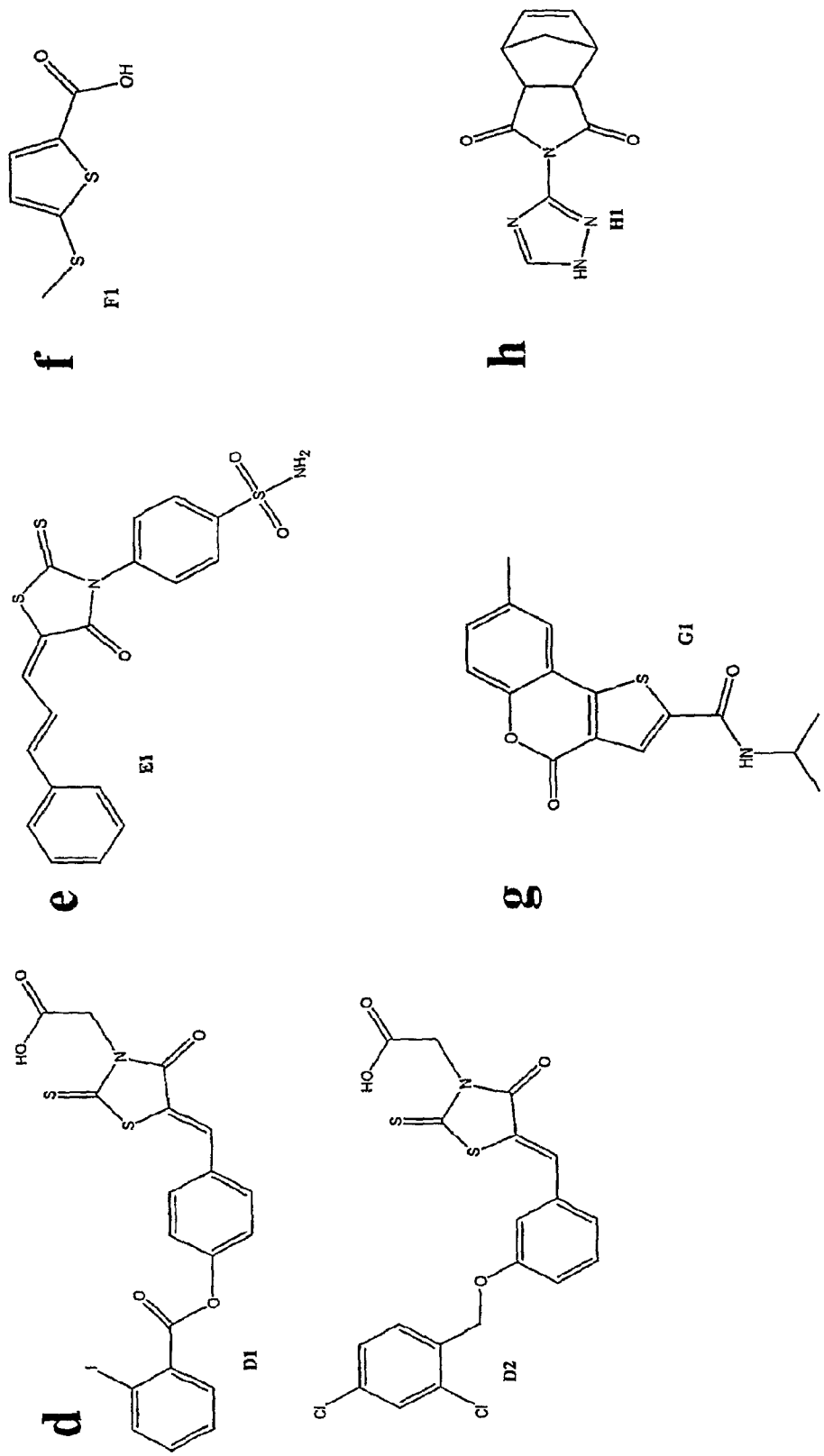
Figure 2:
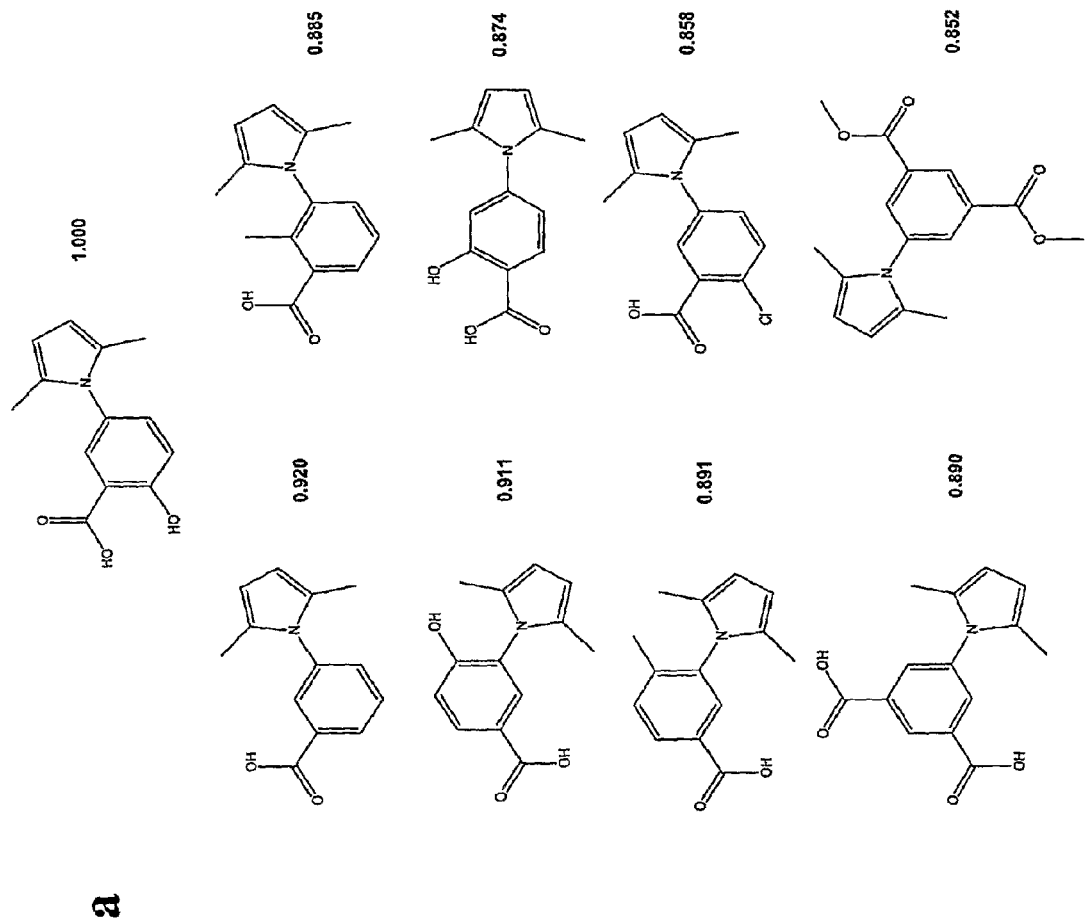
FIG. 2 shows the structural homologues and Tanimoto coefficients of (a) compound A2, (b) compound A3, (c) compound B1, (d) compound C1, (e) compound D1, (f) compound D2, (g) compound E1, (h) compound F1, (i) compound G1, and (j) compound H1.
Figure 2:
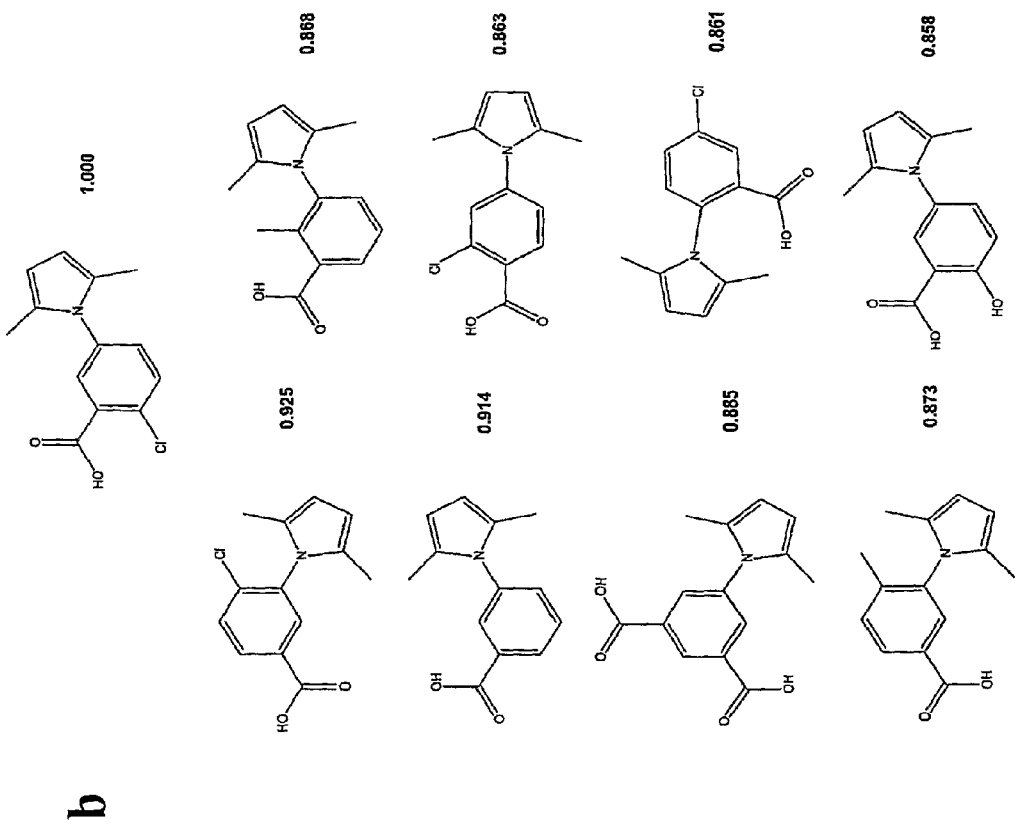
Figure 2:
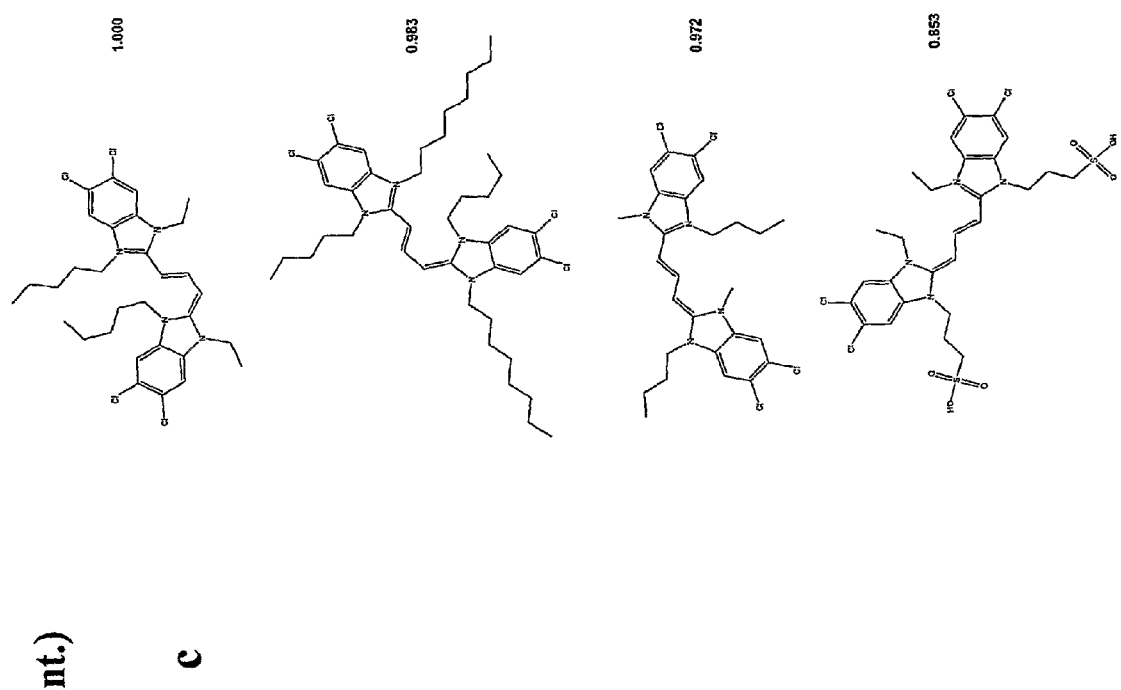
Figure 2:
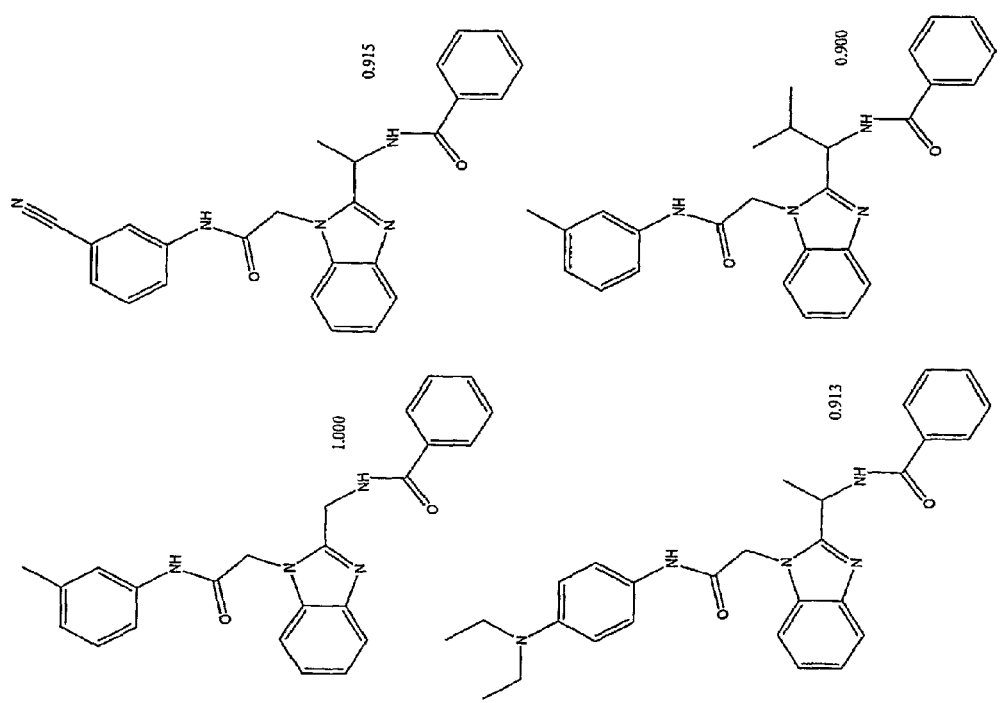
Figure 2:
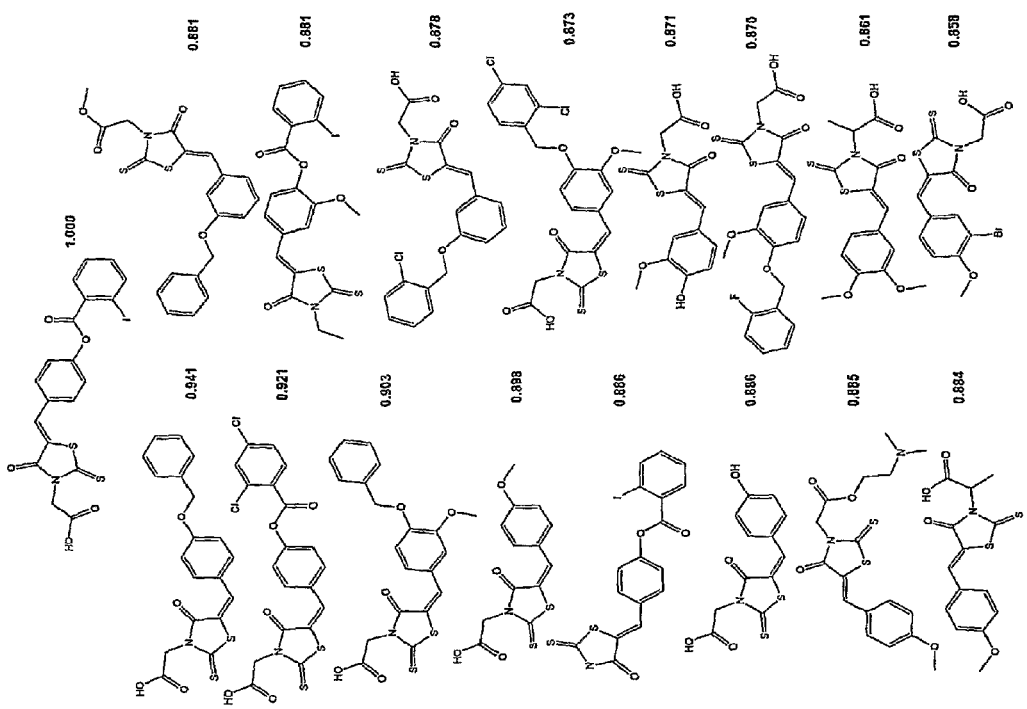
Figure 2:
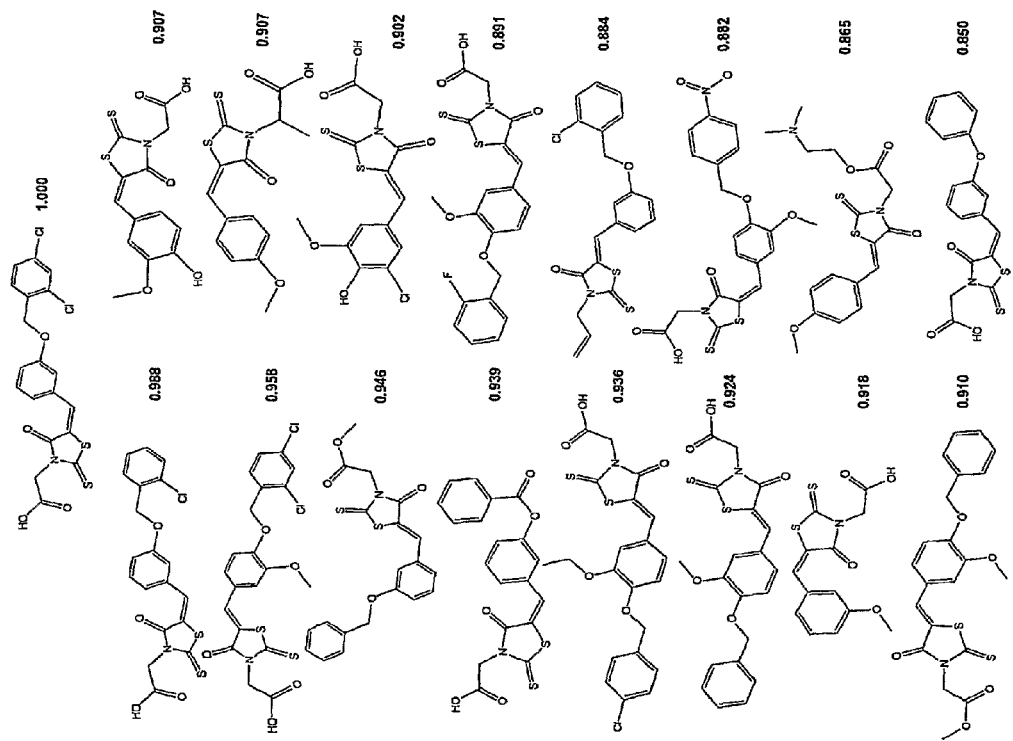
Figure 2:
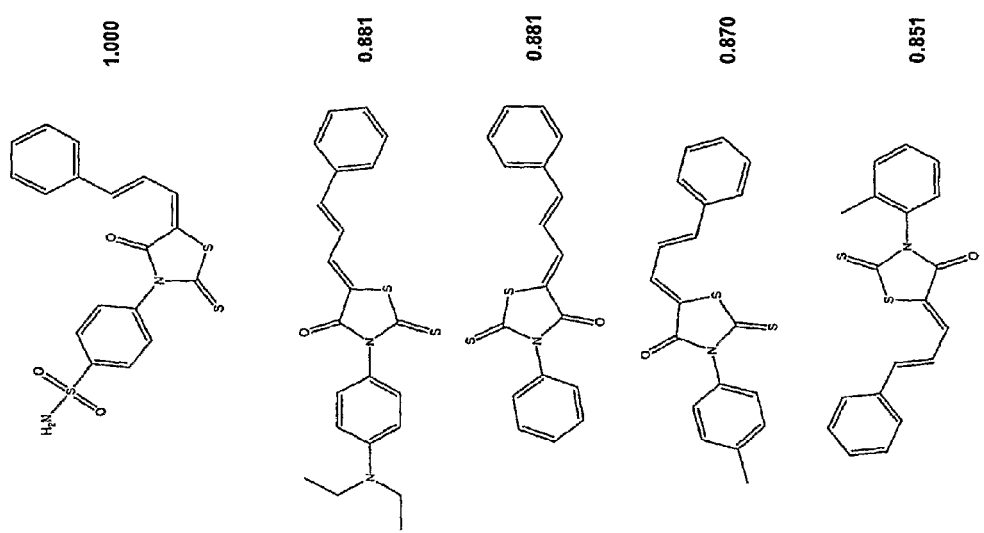
Figure 2:
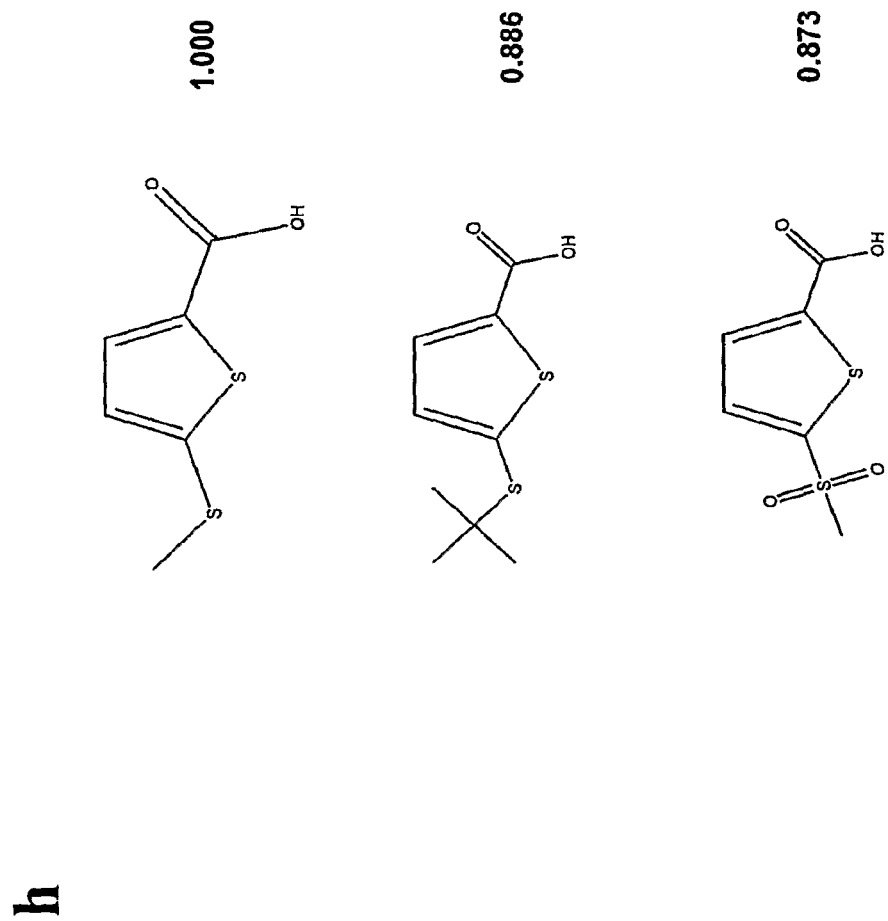
Figure 2:
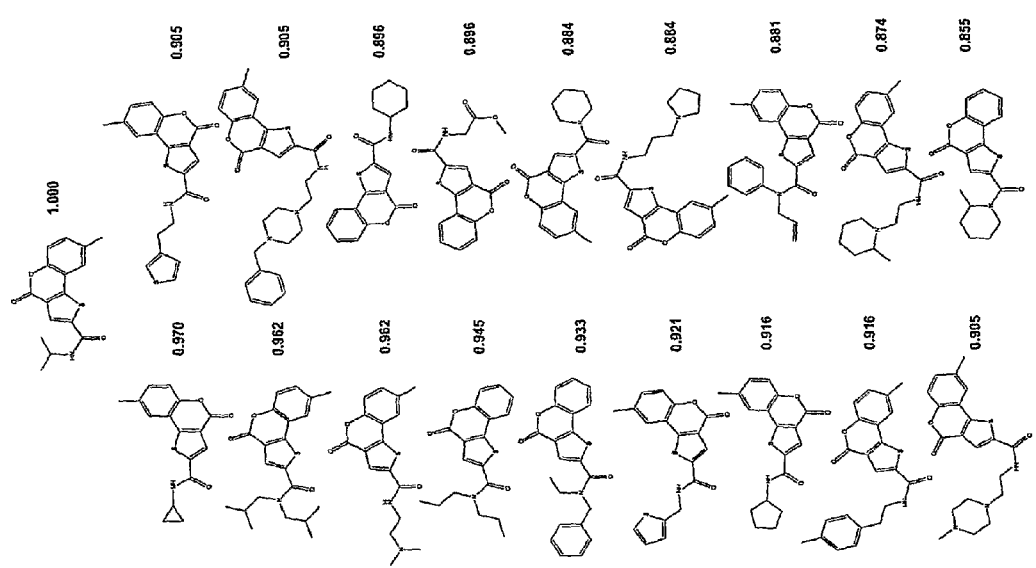
Figure 2:
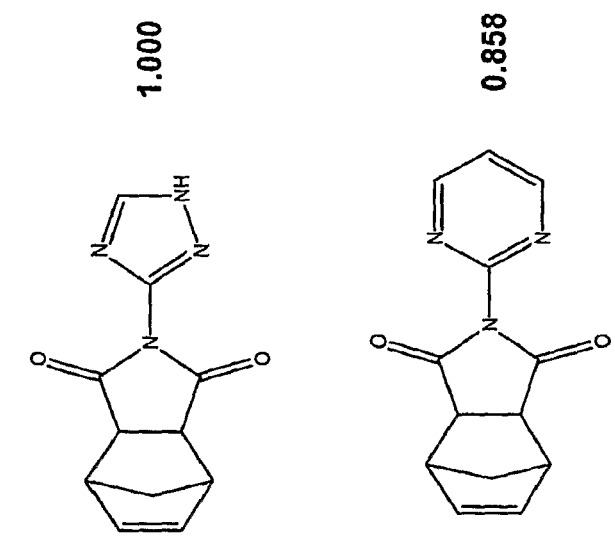

The invention described herein features a screening method for the identification of inhibitors of PKM2. Eight chemical families were identified in the screen (formulas (I)-(VIII); FIG. 1). Eleven compounds (FIG. 2) were found that inhibit glycolysis, affect proliferation, and initiate cell death. These compounds and their structural homologues (FIG. 2) may be useful for the treatment of, e.g., cancer, diabetes, obesity, autoimmune diseases, proliferation-dependent diseases (e.g., BPH), and other diseases related to PKM2 function Synthesis of Compounds The synthesis of the compounds of the invention may involve selective protection and deprotection of alcohols, amines, sulfhydryls, and carboxylic acid functional groups in one or more reactants. For example, commonly used protecting groups for amines include carbamates, such as tert-butyl, benzyl, 2,2,2-trichloroethyl, 2-trimethylsilylethyl, 9-fluorenylmethyl, allyl, and m-nitrophenyl. Other commonly used protecting groups for amines include amides, such as formamides, acetamides, trifluoroacetamides, sulfonamides, trifluoromethanesulfonyl amides, trimethylsilylethanesulfonamides, and tert-butylsulfonyl amides. Examples of commonly used protecting groups for carboxylic acids include esters, such as methyl, ethyl, tert-butyl, 9-fluorenylmethyl, 2-(trimethylsilyl)ethoxy methyl, benzyl, diphenylmethyl, O-nitrobenzyl, ortho-esters, and halo-esters. Examples of commonly used protecting groups for alcohols include ethers, such as methyl, methoxymethyl, methoxyethoxymethyl, methylthiomethyl, benzyloxymethyl, tetrahydropyranyl, ethoxyethyl, benzyl, 2-napthylmethyl, O-nitrobenzyl, P-nitrobenzyl, P-methoxybenzyl, 9-phenylxanthyl, trityl (including methoxy-trityls), and silyl ethers. Examples of commonly used protecting groups for sulfhydryls include many of the same protecting groups used for hydroxyls. In addition, sulfhydryls can be protected in a reduced form (e.g., as disulfides) or an oxidized form (e.g., as sulfonic acids, sulfonic esters, or sulfonic amides). Protecting groups can be chosen such that selective conditions (e.g., acidic conditions, basic conditions, catalysis by a nucleophile, catalysis by a Lewis acid, or hydrogenation) are required to remove each, exclusive of other protecting groups in a molecule. The conditions required for the addition of protecting groups to amine, alcohol, sulfhydryl, and carboxylic acid functionalities and the conditions required for their removal are provided in detail in "T. W. Green and P. G. M. Wuts: Protective Groups in Organic Synthesis" ($2^{nd}$ ed., 1991, John Wiley & Sons) and "P. J. Kocienski: Protecting Groups" (1994, Georg Thieme Verlag), each of which is hereby incorporated by reference.

In the synthetic schemes provided herein, the use of protecting groups is evident from context to those skilled in the art where for any amine, aldehyde, carboxylic acid, sulfhydryl, or alcohol, any of the protecting groups listed above may be used.

Compounds of Formula I

Compounds of the invention include compounds of formula (I).

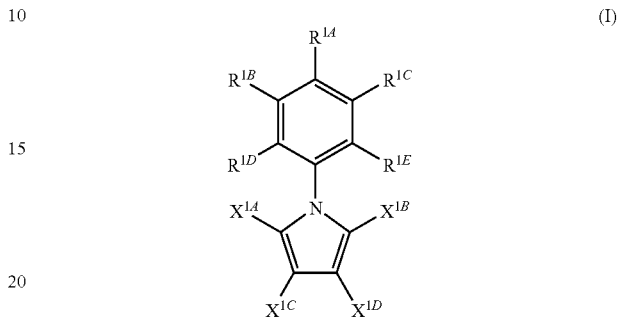

(I)

In formula (I), each of $R^{1A}$, $R^{1B}$, $R^{1C}$, $R^{1D}$, $R^{1E}$, $X^{1A}$, $X^{1B}$, $X^{1C}$, and $X^{1D}$ is, independently, selected from H, halide, nitro, $C_{1-4}$ alkyl, $C_{2-4}$ alkenyl, $C_{2-4}$ alkynyl, $OR^{1K}$, $OC(O)R^{1L}$, $NR^{1M}R^{1N}$, $NHC(O)R^{1O}$, $NHC(S)R^{1P}$, $NHC(O)OR^{1Q}$, $NHC(S)OR^{1R}$, $NHC(O)NHR^{1S}$, $NHC(S)NHR^{1T}$, $NHC(O)SR^{1U}$, $NHC(S)SR^{1V}$, $NHS(O)_2R^{1W}$, $C(O)OR^{1X}$, $C(O)NHR^{1Y}$, $(CH_2)_{1-4}OH$, $C(O)R^{1Z}$, $CH_2R^{1AA}$, $SO_3H$, $SO_2R^{1BB}$, $S(O)R^{1CC}$, $SR^{1DD}$, $SO_2NHR^{1EE}$, and $S(CH_2)_{1-4}C(O)OH$; and each of $R^{1K}$, $R^{1L}$, $R^{1M}$, $R^{1N}$, $R^{1O}$, $R^{1P}$, $R^{1Q}$, $R^{1R}$, $R^{1S}$, $R^{1T}$, $R^{1U}$, $R^{1V}$, $R^{1W}$, $R^{1X}$, $R^{1Y}$, $R^{1Z}$, $R^{1AA}$, $R^{1BB}$, $R^{1CC}$, $R^{1DD}$, and $R^{1EE}$ is, independently, selected from H, $C_{1-4}$ alkyl, $C_{2-4}$ alkenyl, $C_{2-4}$ alkynyl, $C_{2-6}$ heterocyclyl, $C_{6-12}$ aryl, $C_{7-14}$ alkaryl, $C_{3-10}$ alkheterocyclyl, and $C_{1-4}$ heteroalkyl. Compounds of formula (I) include, for example, compounds A1, A2, and A3. In a preferred embodiment, $R^{1A}$ is a hydroxyl and $R^{1B}$ or $R^{1C}$ is a carboxylic acid.

Compounds of formula (I) can be synthesized from aniline to afford, after pyrrole formation followed by one or more electrophilic aromatic substitution (EAS) reactions, the desired phenyl pyrrole compounds (see Scheme 1).

Scheme 1

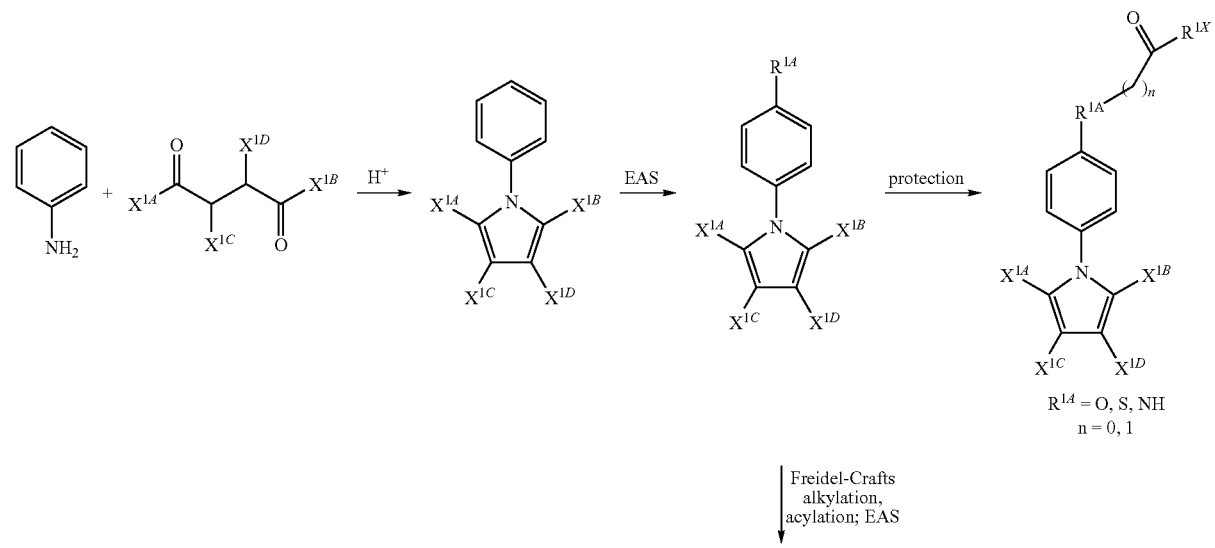

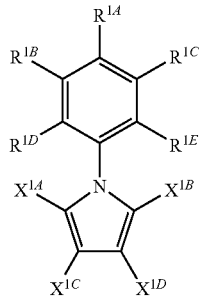

Compounds of Formula II

Compounds of the invention include compounds of formula (II).

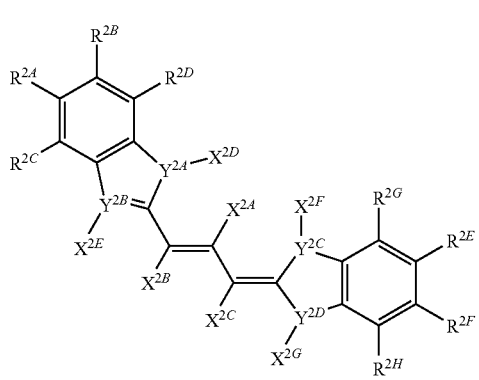

(II)

In formula (II), each of $X^{2A}$, $X^{2B}$, $X^{2C}$, $X^{2C}$, $X^{2D}$, $X^{2E}$, $X^{2F}$, and $X^{2G}$ is, independently, selected from H, $C_{1-8}$ alkyl, $C_{2-4}$ alkenyl, $C_{2-4}$ alkynyl, $C_{2-6}$ heterocyclyl, $C_{6-12}$ aryl, $C_{7-14}$ alkaryl, $C_{3-10}$ alkheterocyclyl, and $C_{1-8}$ heteroalkyl; and each of $Y^{2A}$, $Y^{2C}$, and $Y^{2D}$ is, independently, selected from N and CH; and $Y^{2B}$ is, independently, selected from N+ and C; and each of $R^{2A}$, $R^{2B}$, $R^{2C}$, $R^{2D}$, $R^{2E}$, $R^{2F}$, $R^{2G}$, and $R^{2H}$ is independently, selected from H, halide, nitro, $C_{1-4}$ alkyl, $C_{2-4}$ alkenyl, $C_{2-4}$ alkynyl, $OR^{2K}$, $OC(O)R^{2L}$, $NR^{2M}R^{2N}$, $NHC(O)R^{2O}$, $NHC(S)R^{2P}$, $NHC(O)OR^{2Q}$, $NHC(S)OR^{2R}$, $NHC(O)NHR^{2S}$, $NHC(S)NHR^{2T}$, $NHC(O)SR^{2U}$, $NHC(S)SR^{2V}$, $NHS(O)_2R^{2W}$, $C(O)OR^{2X}$, $C(O)NHR^{2Y}$, $(CH_2)_{1-4}OH$, $C(O)R^{2Z}$, $CH_2R^{2AA}$, $SO_3H$, $SO_2R^{2BB}$, $S(O)R^{2CC}$, $SR^{2DD}$, $SO_2NHR^{2EE}$, and $S(CH_2)_{1-4}C(O)OH$; and each of $R^{2K}$, $R^{2L}$, $R^{2M}$, $R^{2N}$, $R^{2O}$, $R^{2P}$, $R^{2Q}$, $R^{2R}$, $R^{2S}$, $R^{2T}$, $R^{2U}$, $R^{2V}$, $R^{2W}$, $R^{1X}$, $R^{2Y}$, $R^{2Z}$, $R^{2AA}$, $R^{2BB}$, $R^{2CC}$, $R^{2DD}$, and $R^{2EE}$ is, independently, selected from H, $C_{1-4}$ alkyl, $C_{2-4}$ alkenyl, $C_{2-4}$ alkynyl, $C_{2-6}$ heterocyclyl, $C_{6-12}$ aryl, $C_{7-14}$ alkaryl, $C_{3-10}$ alkheterocyclyl, and $C_{1-4}$ heteroalkyl Compounds of formula (II) include, for example, compound B1.

Compounds of formula (II) can be synthesized, e.g., as described in Pawlik et al., *Eur. J. Org. Chem.* 2003:3065-80, 2003 (see Scheme 2).

According to the literature, 5,5',6,6'-tetrachloro-1,1'-dinalkyl-3,3'-bis(ω-carboxyalkyl)benzimidacarbocyanine dyes (1) may be synthesized in a four-step procedure (c.f. Scheme 2, route I) starting from 2,4,5-trichloronitrobenzene (7), which is converted by treatment with n-alkylamines into 4,5-dichloro-ortho-nitroanilines (8). Reduction and simultaneous cyclization with acetic acid then gives 4,5-dichloro-2-methylbenzimidazoles (5). These are quaternized, either with the respective sultones in the case of the 3,3'-di-(ω-sulfoalkyl) substituted dyes, or with ω-bromoalkylnitriles or alkanoic acid ethyl esters in the case of the 3,3'-bis(ω-carboxyalkyl) substituted dyes, and subsequently saponified. Two equivalents of the 1-alkyl-3-(ω-carboxyalkyl)-5,6-dichloro-2-methylbenzimidazolium bromides (6) thus obtained are transformed into the respective benzimidacarbocyanine dyes 1 by treatment with iodoform in the presence of sodium methoxide (De Rossi et al., *J. Prakt. Chem. Chem.-Ztg.* 337:203-8, 1995).

Alternate synthetic routes are also shown in Scheme 2. 4,5-Dichloro-ortho-phenylenediamine (2) was condensed with acetic acid according to Dandegaonker and Kanabur (Dandegaonker, *Monatsh. Chem.* 99:1467-72, 1968), yielding the 5,6-dichlorobenzimidazole (3), which serves as the starting compound for variation both of the substituents on the 1,1'- and the 3,3'-nitrogen atoms.

In reaction route II, the 3-(3-cyanopropyl) group is first introduced through nucleophilic reaction between (3) and ω-bromoalkylnitriles to give compounds (4), which are concomitantly quaternized with n-alkyl bromides and hydrolysed to give 1-alkyl-3-(3-carboxypropyl)-5,6-dichlorobenzimidazoles (6). Finally, as in De Rossi et al., condensation of two equivalents of (6) with iodoform in alkaline medium gives dyes (1). If 1,8-diazabicyclo[5.4.0]undec-7-ene (DBU) is used instead of the common sodium methoxide, the reaction can be performed at room temperature.

In reaction route III, the 1-alkyl substituents are first introduced in (3) by nucleophilic reaction with the corresponding alkyl bromides, giving compounds (5). These are transformed into precursors (6) through quaternization either with ω-bromoalkanoic acid ethyl esters or with ω-bromoalkylnitriles, with subsequent hydrolysis. In the case of the 3,3'-bis(ω-sulfoalkyl)-substituted dyes, quaternization is achieved through the usual reaction with the corresponding sultones (Poppe et al., *Photogr. Photophys. Photochem.* 63:149-58, 1969). The compounds are purified in the usual way by precipitation from methanol or dimethyl sulfoxide solutions by addition of small amounts of water.

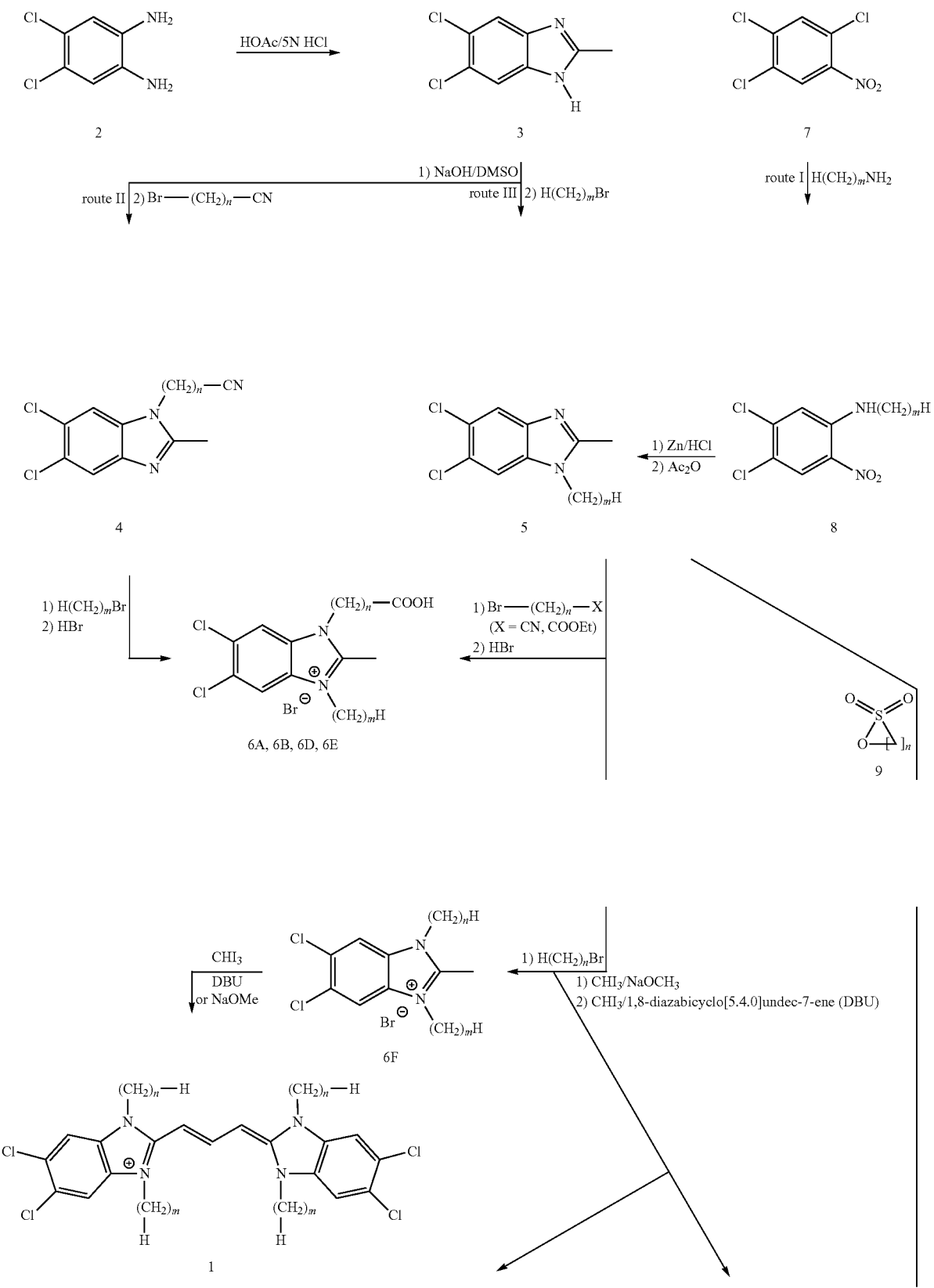
Scheme 2

-continued

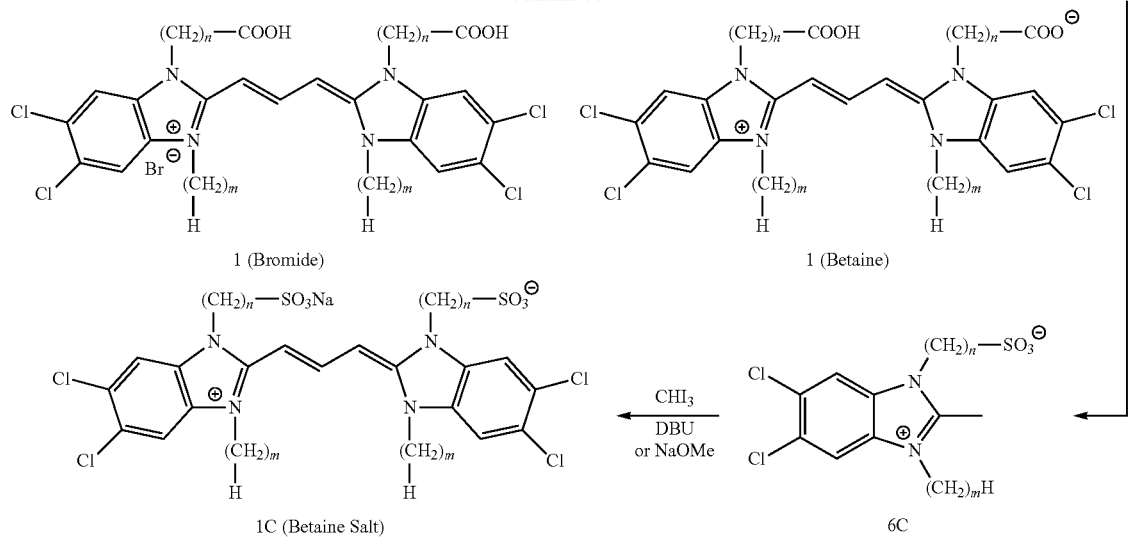

1 (Bromide)

1 (Betaine)

1C (Betaine Salt)

6C

Compounds of Formula III

Compounds of the invention include compounds of formula (III).

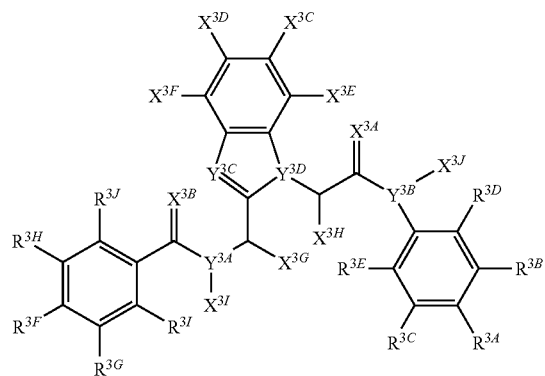
(III)

In formula (III), each of $X^{3A}$ and $X^{3B}$ is, independently, selected from S, O, NH, and $CH_2$; and each of $X^{3G}$ and $X^{3H}$ is, independently, selected from H, $C_{1-8}$ alkyl, $C_{2-4}$ alkenyl, $C_{2-4}$ alkynyl, and $C_{1-8}$ heteroalkyl; and each of $Y^{3A}$ and $Y^{3B}$ is, independently, selected from O, CH, N, and S; and $X^{3I}$ is empty when $Y^{3A}$ is S or O, $X^{3J}$ is empty when $Y^{3B}$ is S or O, otherwise each of $X^{3I}$ and $X^{3J}$ is, independently, selected from H, $C_{1-8}$ alkyl, $C_{2-4}$ alkenyl, $C_{2-4}$ alkynyl, and $C_{1-8}$ heteroalkyl; and each of $Y^{3C}$ and $Y^{3D}$ is, independently, selected from CH and N; and each of $R^{3A}$, $R^{3B}$, $R^{3C}$, $R^{3D}$, $R^{3E}$, $R^{3F}$, $R^{3G}$, $R^{3H}$, $R^{3I}$, $R^{3J}$, $X^{3C}$, $X^{3D}$, $X^{3E}$, and $X^{3F}$ is, independently, selected from H, halide, nitro, $C_{1-4}$ alkyl, $C_{2-4}$ alkenyl, $C_{2-4}$ alkynyl, $OR^{3K}$, $OC(O)R^{3L}$, $NR^{3M}R^{3N}$, $NHC(O)R^{3O}$, $NHC(S)R^{3P}$, $NHC(O)OR^{3Q}$, $NHC(S)OR^{3R}$, $NHC(O)NHR^{3S}$, $NHC(S)NHR^{3T}$, $NHC(O)SR^{3U}$, $NHC(S)SR^{3V}$, $NHS(O)_2R^{3BB}$, $C(O)OR^{3X}$, $C(O)NHR^{3Y}$, $(CH_2)_{1-4}OH$, $C(O)R^{3Z}$, $CH_2R^{3AA}$, $SO_3H$, $SO_2R^{3BB}$, $S(O)R^{3CC}$, $SR^{3DD}$, $SO_2NHR^{3EE}$, and $S(CH_2)_{1-4}C(O)OH$; and each of $R^{3K}$, $R^{3L}$, $R^{3M}$, $R^{3N}$, $R^{3O}$, $R^{3P}$, $R^{3Q}$, $R^{3R}$, $R^{3S}$, $R^{3T}$, $R^{3U}$, $R^{3V}$, $R^{3W}$, $R^{3X}$, $R^{3Y}$, $R^{3Z}$, $R^{3AA}$, $R^{3BB}$, $R^{3CC}$, $R^{3DD}$, and $R^{3EE}$ is, independently, selected from H, $C_{1-4}$ alkyl, $C_{2-4}$ alkenyl, $C_{2-4}$ alkynyl, $C_{2-6}$ heterocyclyl, $C_{6-12}$ aryl, $C_{7-14}$ alkaryl, $C_{3-10}$ alkheterocyclyl, and $C_{1-4}$ heteroalkyl. Compounds of formula (III) include, for example, compound C1.

Compounds of formula (III) can be synthesized from bezimidazole derivatives to afford, after reductive amination followed by C-alkylation, the desired compounds (see Scheme 3).

Scheme 3

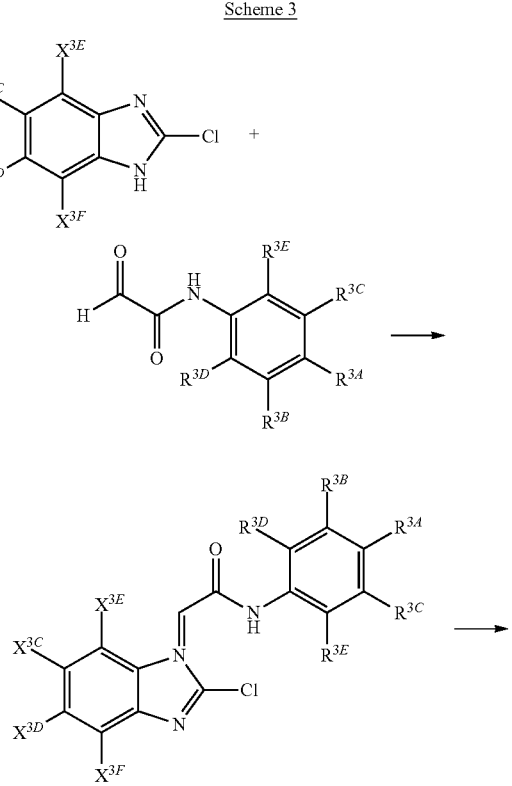

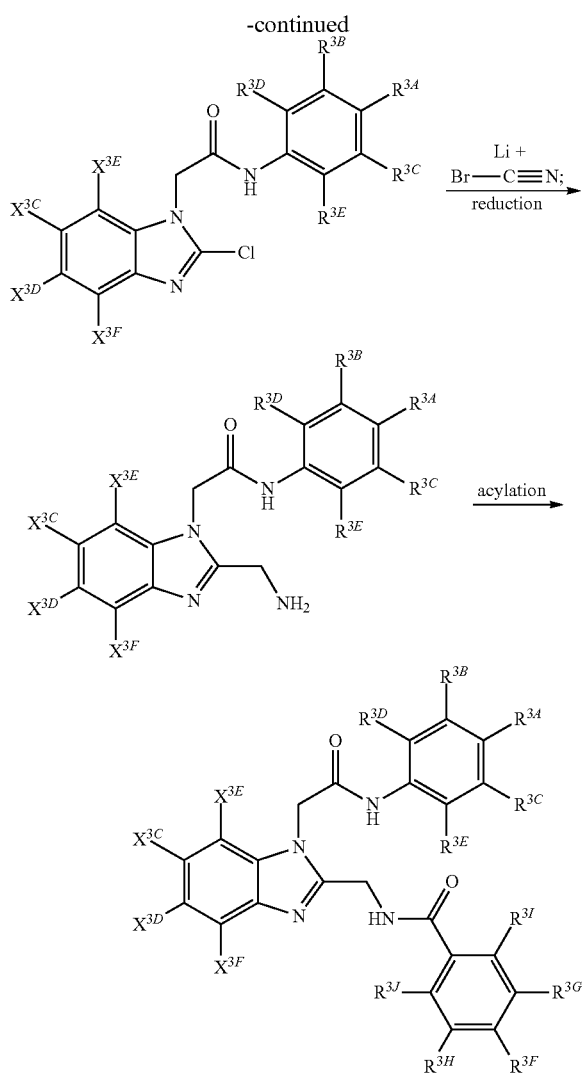

Compounds of Formula IV

Compounds of the invention include compounds of formula (IV).

(IV)

In formula (IV), each of $X^{4A}$, $X^{4B}$, and $X^{4C}$ is, independently, selected from S, O, NH, CH$_2$, and two hydrogen atoms; and each of $X^{4G}$ and $X^{4H}$ is, independently, selected from H, C$_{1-8}$ alkyl, C$_{2-4}$ alkenyl, C$_{2-4}$ alkynyl, and C$_{1-8}$ heteroalkyl; and each of $X^{4D}$ and $X^{4E}$ is, independently, selected from O, CH$_2$, NH, and S; and $X^{4F}$ is, independently, selected from CH and N; and each of $R^{4A}$, $R^{4B}$, $R^{4C}$, $R^{4D}$, $R^{4E}$, $R^{4F}$, $R^{4G}$, $R^{4H}$, and $R^{4I}$, is, independently, selected from H, halide, nitro, C$_{1-4}$ alkyl, C$_{2-4}$ alkenyl, C$_{2-4}$ alkynyl, OR$^{4K}$, OC(O)R$^{4L}$, NR$^{4M}$R$^{4N}$, NHC(O)R$^{4O}$, NHC(S)R$^{4P}$, NHC(O)OR$^{4Q}$, NHC(S)OR$^{4R}$, NHC(O)NHR$^{4S}$, NHC(S)NHR$^{4T}$, NHC(O)SR$^{4U}$, NHC(S)SR$^{4V}$, NHS(O)$_2$R$^{4W}$, C(O)OR$^{4X}$, C(O)NHR$^{4Y}$, (CH$_2$)$_{1-4}$OH, C(O)R$^{4Z}$, CH$_2$R$^{4AA}$, SO$_3$H, SO$_2$R$^{4BB}$, S(O)R$^{4CC}$, SR$^{4DD}$, SO$_2$NHR$^{4EE}$, and S(CH$_2$)$_{1-4}$C(O)OH; and each of R$^{4K}$, R$^{4L}$, R$^{4M}$, R$^{4N}$, R$^{4O}$, R$^{4P}$, R$^{4Q}$, R$^{4R}$, R$^{4S}$, R$^{4T}$, R$^{4U}$, R$^{4V}$, R$^{4W}$, R$^{4X}$, R$^{4Y}$, R$^{4Z}$, R$^{4AA}$, R$^{4BB}$, R$^{4CC}$, R$^{4DD}$, and R$^{4EE}$ is, independently, selected from H, C$_{1-4}$ alkyl, C$_{2-4}$ alkenyl, C$_{2-4}$ alkynyl, C$_{2-6}$ heterocyclyl, C$_{6-12}$ aryl, C$_{7-14}$ alkaryl, C$_{3-10}$ alkheterocyclyl, and C$_{1-4}$ heteroalkyl. Compounds of formula (IV) include, for example, compounds D1 and D2. In a preferred embodiment, $X^{4A}$ is O or S and $X^{4D}$ is para-substituted relative to the group containing $X^{4H}$.

Compounds of formula (IV) can be synthesized as described in Schemes 4, 5, 6, 7, and 8:

Firstly, a bicyclic ring system is prepared, e.g., by amide, ester, ether, or enol ether formation, by ester formation as described in, e.g., Gaylord et al., *Organic Syntheses* 32:25, 1952) (Scheme 4), Scheme 4

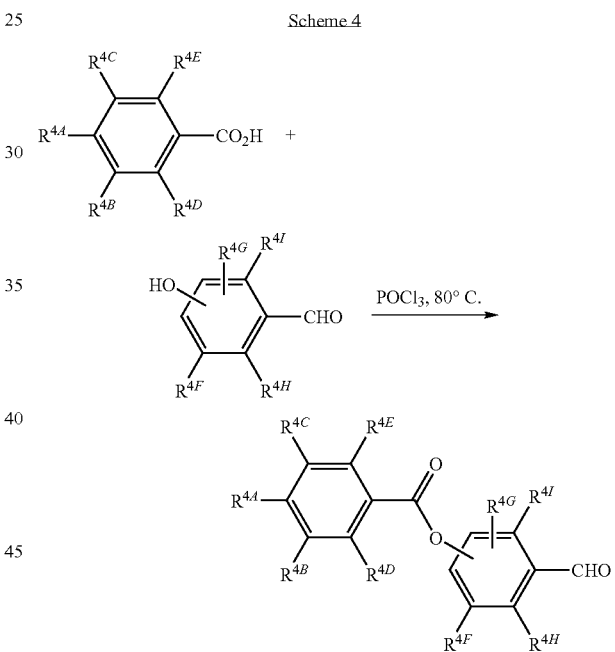

and optionally followed by methylenation of the ester as described in, e.g., Pine et al., *Organic Syntheses* 69:72, 1990) (Scheme 5), Scheme 5

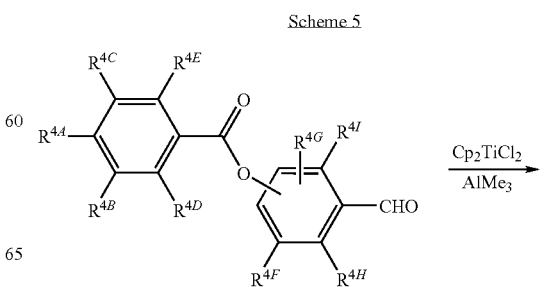

-continued

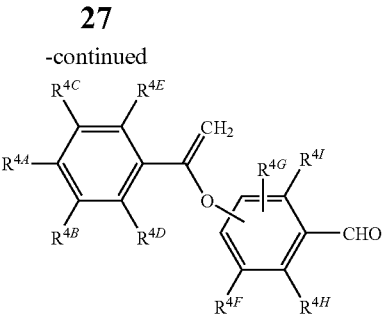

or by amide formation as described in, e.g., Allen et al., *Organic Syntheses* 26:92, 1946) (Scheme 6), -continued

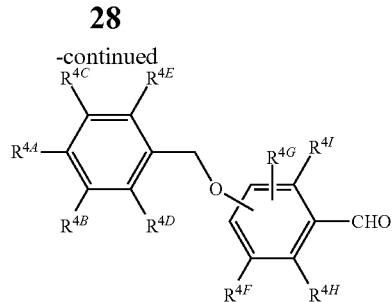

and then condensation, e.g., of various substituted 2,4-thiazolidinediones with various substituted benzaldehydes using piperidine as base, in refluxing ethanol, as described in Momose et al., *Chem. Pharm. Bull.* 39:1440, 1991, and Bruno et al., *Bioorg. & Med. Chem.* 10:1077-84, 2002) (Scheme 8).

Scheme 6

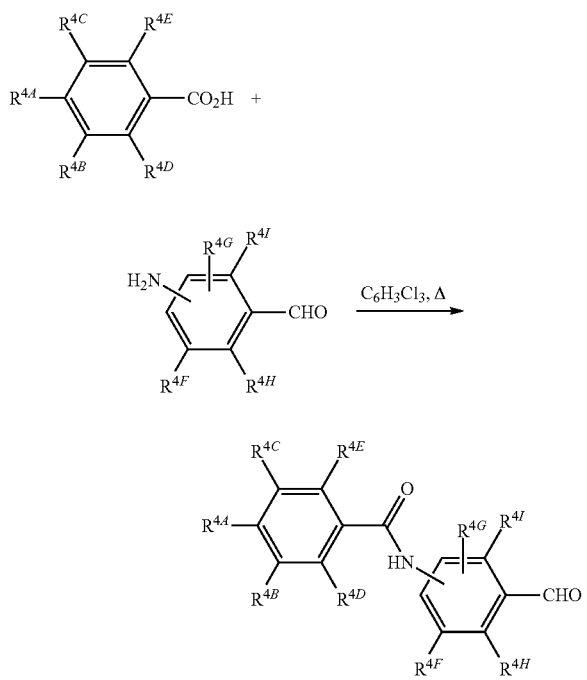

or by ether formation using the Williamson Synthesis (Scheme 7),

Scheme 7

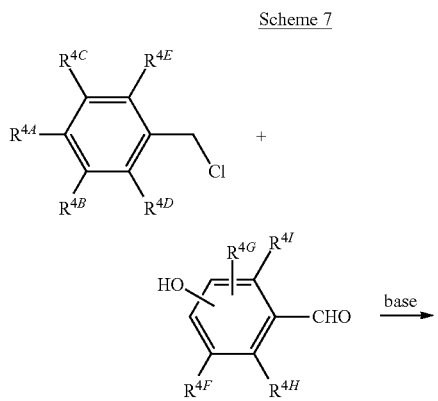

Scheme 8

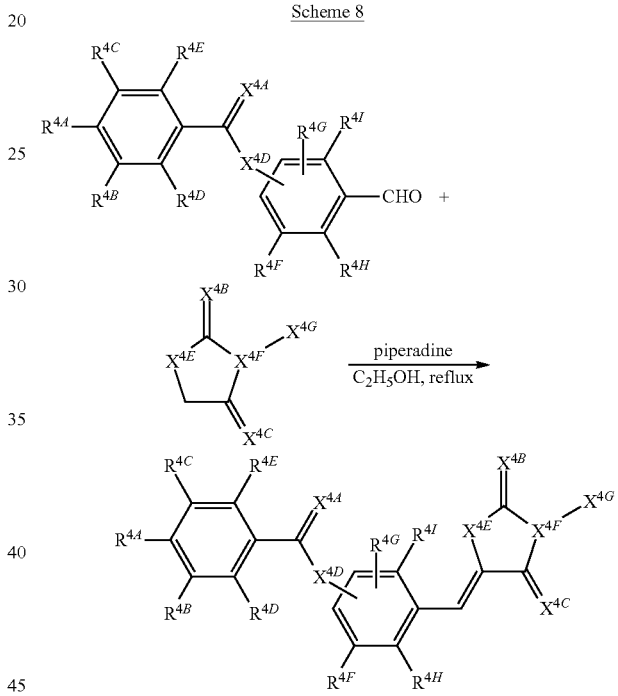

Compounds of Formula V

Compounds of the invention include compounds of formula (V).

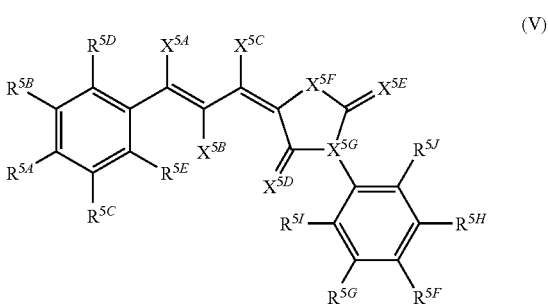

(V)

In formula (V), each of $X^{5A}$, $X^{5B}$, and $X^{5C}$ is, independently, selected from H, $C_{1-8}$ alkyl, $C_{2-4}$ alkenyl, $C_{2-4}$ alkynyl, and $C_{1-8}$ heteroalkyl; and each of $X^{5D}$ and $X^{5E}$ is, independently, selected from S, NH, O, and CH$_2$; and X$^{5F}$ is, independently, selected from O, NH, CH$_2$, and S; and X$^{5G}$ is, independently, selected from CH and N; and each of R$^{5A}$, R$^{5B}$, R$^{5C}$, R$^{5D}$, R$^{5E}$, R$^{5F}$, R$^{5G}$, R$^{5H}$, R$^{5I}$, and R$^{5J}$, is, independently, selected from H, halide, nitro, C$_{1-4}$ alkyl, C$_{2-4}$ alkenyl, C$_{2-4}$ alkynyl, OR$^{5K}$, OC(O)R$^{5L}$, NR$^{5M}$R$^{5N}$, NHC(O)R$^{5O}$, NHC(S)R$^{5P}$, NHC(O)OR$^{5Q}$, NHC(S)OR$^{5R}$, NHC(O)NHR$^{5S}$, NHC(S)NHR$^{5T}$, NHC(O)SR$^{5U}$, NHC(S)SR$^{5V}$, NHS(O)$_2$R$^{5W}$, C(O)OR$^{5X}$, C(O)NHR$^{5Y}$, (CH$_2$)$_{1-4}$OH, C(O)R$^{5Z}$, CH$_2$R$^{5AA}$, SO$_3$H, SO$_2$R$^{5BB}$, S(O)R$^{5CC}$, SR$^{5DD}$, SO$_2$NHR$^{5EE}$, and S(CH$_2$)$_{1-4}$C(O)OH; and each of R$^{5K}$, R$^{5L}$, R$^{5M}$, R$^{5N}$, R$^{5O}$, R$^{5P}$, R$^{5Q}$, R$^{5R}$, R$^{5S}$, R$^{5T}$, R$^{5U}$, R$^{5V}$, R$^{5W}$, R$^{5X}$, R$^{5Y}$, R$^{5Z}$, R$^{5AA}$, R$^{5BB}$, R$^{5CC}$, R$^{5DD}$, and R$^{5EE}$ is, independently, selected from H, C$_{1-4}$ alkyl, C$_{2-4}$ alkenyl, C$_{2-4}$ alkynyl, C$_{2-6}$ heterocyclyl, C$_{6-12}$ aryl, C$_{7-14}$ alkaryl, C$_{3-10}$ alkheterocyclyl, and C$_{1-4}$ heteroalkyl. Compounds of formula (V) include, for example, compound E1.

Compounds of formula (V) can be synthesized by condensation of cinnamic aldehyde derivatives with various carbanionic nucleophiles, as is depicted in Scheme 9.

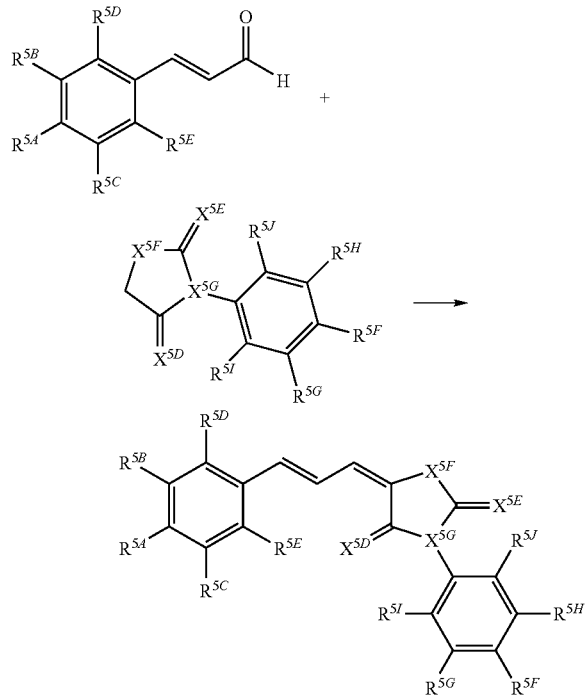

Compounds of Formula VI

Compounds of the invention include compounds of formula (VI).

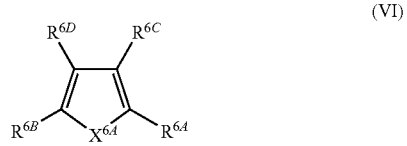

In formula (VI), X$^{6A}$ is, independently, selected from S, NH, and O; and each of R$^{6A}$, R$^{6B}$, R$^{6C}$, and R$^{6D}$, is, independently, selected from H, halide, nitro, C$_{1-4}$ alkyl, C$_{2-4}$ alkenyl, C$_{2-4}$ alkynyl, OR$^{6K}$, OC(O)R$^{6L}$, NR$^{6M}$R$^{6N}$, NHC(O)R$^{6O}$, NHC(S)R$^{6P}$, NHC(O)OR$^{6Q}$, NHC(S)OR$^{6R}$, NHC(O)NHR$^{6S}$, NHC(S)NHR$^{6T}$, NHC(O)SR$^{6U}$, NHC(S)SR$^{6V}$, NHS(O)$_2$R$^{6W}$, C(O)OR$^{6X}$, C(O)NHR$^{6Y}$, (CH$_2$)$_{1-4}$OH, C(O)R$^{6Z}$, CH$_2$R$^{6AA}$, SO$_3$H, SO$_2$R$^{6BB}$, S(O)R$^{6CC}$, SR$^{6DD}$, SO$_2$NHR$^{6EE}$, and S(CH$_2$)$_{1-4}$C(O)OH; and
each of R$^{6K}$, R$^{6L}$, R$^{6M}$, R$^{6N}$, R$^{6O}$, R$^{6P}$, R$^{6Q}$, R$^{6R}$, R$^{6S}$, R$^{6T}$, R$^{6U}$, R$^{6V}$, R$^{6W}$, R$^{6X}$, R$^{6Y}$, R$^{6Z}$, R$^{6AA}$, R$^{6BB}$, R$^{6CC}$, R$^{6DD}$, and R$^{6EE}$ is, independently, selected from H, C$_{1-4}$ alkyl, C$_{2-4}$ alkenyl, C$_{2-4}$ alkynyl, C$_{2-6}$ heterocyclyl, C$_{6-12}$ aryl, C$_{7-14}$ alkaryl, C$_{3-10}$ alkheterocyclyl, and C$_{1-4}$ heteroalkyl. Compounds of formula (VI) include, for example, compound F1.

Compounds of formula (VI) can be synthesized from furan, thiophene and pyrrole derivatives by sequential electrophilic aromatic substitution (EAS) reactions, as is depicted in Scheme 10.

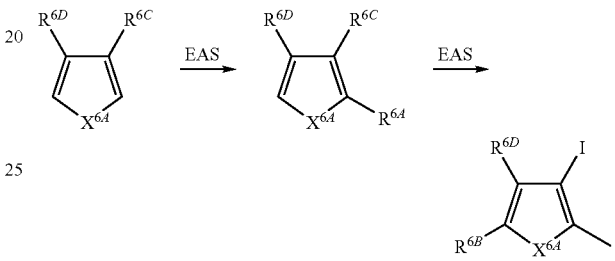

Compounds of Formula VII

Compounds of the invention include compounds of formula (VII).

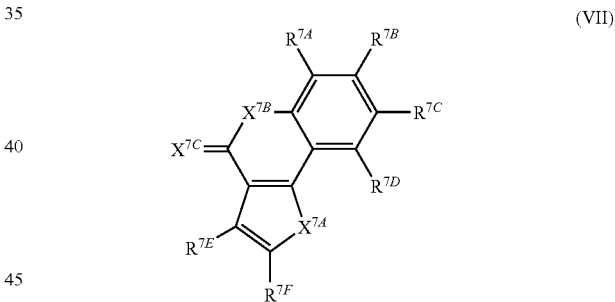

In formula (VII), each of X$^{7A}$ and X$^{7B}$ is, independently, selected from S, NH, and O; and X$^{7C}$ is, independently, selected from S, NH, CH$_2$, and O; and each of R$^{7A}$, R$^{7B}$, R$^{7C}$, R$^{7D}$, R$^{7E}$, and R$^{7F}$ is, independently, selected from H, halide, nitro, C$_{1-4}$ alkyl, C$_{2-4}$ alkenyl, C$_{2-4}$ alkynyl, OR$^{7K}$, OC(O)R$^{7L}$, NR$^{7M}$R$^{7N}$, NHC(O)R$^{7O}$, NHC(S)R$^{7P}$, NHC(O)OR$^{7Q}$, NHC(S)OR$^{7R}$, NHC(O)NHR$^{7S}$, NHC(S)NHR$^{7T}$, NHC(O)SR$^{7U}$, NHC(S)SR$^{7V}$, NHS(O)$_2$R$^{7W}$, C(O)OR$^{7X}$, C(O)NHR$^{7Y}$, (CH$_2$)$_{1-4}$OH, C(O)R$^{7Z}$, CH$_2$R$^{7AA}$, SO$_3$H, SO$_2$R$^{7BB}$, S(O)R$^{7CC}$, SR$^{7DD}$, SO$_2$NHR$^{7EE}$, and S(CH$_2$)$_{1-4}$C(O)OH; and each of R$^{7K}$, R$^{7L}$, R$^{7M}$, R$^{7N}$, R$^{7O}$, R$^{7P}$, R$^{7Q}$, R$^{7R}$, R$^{7S}$, R$^{7T}$, R$^{7U}$, R$^{7V}$, R$^{7W}$, R$^{7X}$, R$^{7Y}$, R$^{7Z}$, R$^{7AA}$, R$^{7BB}$, R$^{7CC}$, R$^{7DD}$, and R$^{7EE}$, is, independently, selected from H, C$_{1-4}$ alkyl, C$_{2-4}$ alkenyl, C$_{2-4}$ alkynyl, C$_{2-6}$ heterocyclyl, C$_{6-12}$ aryl, C$_{7-44}$ alkaryl, C$_{3-10}$ alkheterocyclyl, and C$_{1-4}$ heteroalkyl. Compounds of formula (VII) include, for example, compound G1.

Compounds of formula (VII) can be synthesized from furan, thiophene or pyrrole derivatives by an aromatic radical substitution reaction, followed by an intramolecular cyclization reaction, as is depicted in Scheme 11.

Scheme 11

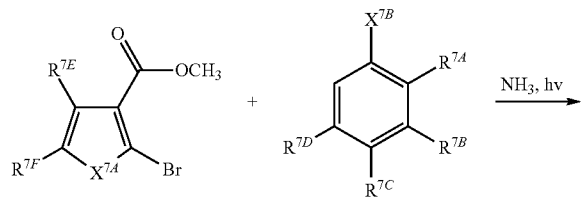

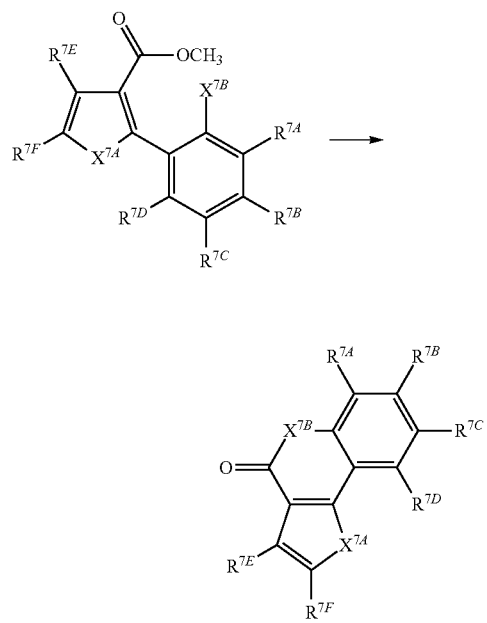

Compounds of Formula VIII

Compounds of the invention include compounds of formula (VIII).

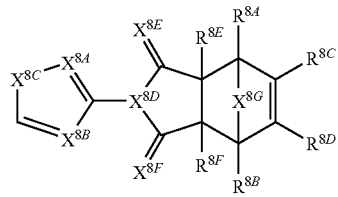
(VIII)

In formula VIII, $X^{8C}$ is, independently, selected from NH, CH=CH, or N=CH; and each of $X^{8A}$, $X^{8B}$, and $X^{8D}$ is, independently, selected from CH and N; and each of $X^{8E}$, $X^{8F}$ and $X^{8G}$ is, independently, selected from S, NH, CH$_2$, and O; and each of $R^{8A}$, $R^{8B}$, $R^{8C}$, $R^{8D}$, $R^{8E}$, and $R^{8F}$ is, independently, selected from H, $C_{1-4}$ alkyl, $C_{2-4}$ alkenyl, $C_{2-4}$ alkynyl, $C_{2-6}$ heterocyclyl, $C_{6-42}$ aryl, $C_{7-14}$ alkaryl, $C_{3-40}$ alkheterocyclyl, and $C_{1-4}$ heteroalkyl. Compounds of formula (VIII) include, for example, compound H1.

Compound of formula (VIII) can be synthesized from reaction of a diene, such as cyclopentadiene, furan, thiophene, or a pyrrole derivative, with an appropriately substituted dienophile via the Diels Alder reaction, as is depicted in Scheme 12.

Scheme 12

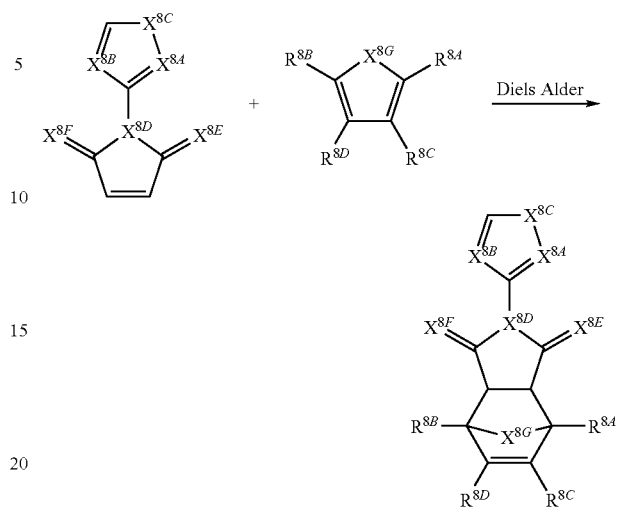

Chemical Inhibition of PKM2

Currently, no compounds used to inhibit glycolysis are approved for use in a subject. One limitation to current glycolytic inhibitors is that they are non-specific, which is problematic given the importance of glucose utilization in normal tissues. Since PKM2 is specific to cancer cells, adipose tissue, and activated immunogenic cells, it is an ideal target for the inhibition of glycolysis in cancer cells and the inhibition of diseases associated with the expression of PKM2. Thus, a screen was devised to identify inhibitors of PKM2.

PKM1 and PKM2 for use in the screening method may be produced by any method known in the art for expression of recombinant proteins. For example, nucleic acids that encode the desired polypeptide may be introduced into various cell types or cell-free systems for expression. Eukaryotic (e.g., COS, HEK293T, CHO, and NIH cell lines) and prokaryotic (e.g., *E. coli*) expression systems may be generated in which a PKM sequence is introduced into a plasmid or other vector, which is then used to transform living cells. Constructs in which the PKM cDNA contains the entire open reading frame, or biologically active fragment thereof, are inserted in the correct orientation into an expression plasmid and may be used for protein expression. Prokaryotic and eukaryotic expression systems allow for the expression and recovery of fusion proteins in which the PKM protein is covalently linked to a tag molecule on either the amino terminal or carboxy terminal side, which facilitates identification and/or purification. Examples of tags that can be used include hexahistidine, HA, FLAG, and c-myc epitope tags. An enzymatic or chemical cleavage site can be engineered between the PKM protein and the tag molecule so that the tag can be removed following purification.

The activity of the PKM enzyme measured in the screening assay may be measured by, e.g., monitoring the concentration of a substrate (e.g., ATP or NADH) present in the reaction mixture. Pyruvate, produced by the enzymatic activity of pyruvate kinase, is converted into lactate by lactate dehydrogenase, which requires the consumption of NADH (NADH→NAD$^+$). Thus, the activity of PKM2 can be indirectly measured by monitoring the consumption of NADH through, e.g., fluorescence assays. Additionally, the activity of the PKM2 enzyme can be directly monitored by measuring the production of ATP, as ATP is produced when phosphoenolpyruvate is converted to pyruvate. Methods for monitoring the amount of substrate in a reaction mixture include, e.g., absorbance, fluorescence, Raman scattering, phosphorescence, luminescence, luciferase assays, and radioactivity.

The screening procedure requires the presence of specific components in the reaction mixture. Components utilized in the assay include, e.g., a nucleoside diphosphate (e.g., ADP), phosphoenolpyruvate, NADH, lactate dehydrogenase, FBP, a reducing agent (e.g., dithiothreitol), a detergent (e.g., Brij 35), glycerol, and a solvent (e.g., DMSO). Exemplary reaction conditions are found in Table 1.

TABLE 1

| Component of Reaction Condition | Amount |
| --- | --- |
| ADP | 0.1-5.0 mM |
| Phosphoenolpyruvate | 0.1-5.0 mM |
| NADH | 10-1000 μM |
| Lactate dehydrogenase | 0.1-10 units |
| Fructose-1,6-bisphosphate | 1-500 μM |
| DTT | 0.1-50 mM |
| Brij 35 | 0.01-1% |
| Glycerol | 0.1-10% |
| Pyruvate Kinase M2 (used for screen) | 1-100 pg |
| DMSO | 1-10% |

Candidate compounds may be chosen if they demonstrate inhibition of the PKM enzyme greater than 10, 15, 20, 25, 30, 35, 40, 45, 50, 55, 60, 65, 70, 75, 80, 85, 90, 95, 99, or 99.9%.

Therapy

The compounds of the invention described herein are useful in the treatment of, e.g., cancer, obesity, diabetes, autoimmune conditions, and proliferation-dependent diseases. Therapy may be performed alone or in combination with another therapy (e.g., surgery, radiation therapy, chemotherapy, immunotherapy, anti-angiogenesis therapy, or gene therapy). The duration of the combination therapy depends on the type of disease or disorder being treated, the age and condition of the patient, the stage and type of the patient's disease, and how the patient responds to the treatment. Therapy may be given in on-and-off cycles that include rest periods.

Cancer

Inhibitors of PKM2, described herein, may be used in the treatment of, e.g., cancer. Cancers include, without limitation, leukemias (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (Hodgkin's disease, non-Hodgkin's disease), Waldenstrom's macroglobulinemia, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodenroglioma, schwannoma, meningioma, melanoma, neuroblastoma, and retinoblastoma).

Autoimmune Diseases and Proliferative Disorders

Inhibitors of PKM2, described herein, may be used to treat, e.g., autoimmune diseases or proliferative disorders. Autoimmune disorders include, e.g., type I diabetes, Crohn's disease, multiple sclerosis, arthritis, rheumatoid arthritis, systemic lupus erythematosus, autoimmune (Hasimoto's) thyroiditis, autoimmune liver diseases (e.g., hepatitis and primary biliary cirrhosis), hyperthyroidism (e.g., Graves' disease and thyrotoxicosis), insulin-resistant diabetes, autoimmune adrenal insufficiency (e.g., Addison's disease), autoimmune oophoritis, autoimmune orchitis, autoimmune hemolytic anemia, paroxysmal cold hemoglobinuria, Behcet's disease, autoimmune thrombocytopenia, autoimmune neutropenia, pernicious anemia, pure red cell anemia, autoimmune coagulopathies, myasthenia gravis, experimental allergic encephalomyelitis, autoimmune polyneuritis, pemphigus and other bullous diseases, rheumatic carditis, Goodpasture's syndrome, postcardiotomy syndrome, Sjogren's syndrome, polymyositis, dermatomyositis, and scleroderma. Autoimmune disorders are described in U.S. Pat. Nos. 5,891,435 and 6,773,705, hereby incorporated by reference.

Proliferative disorders include, e.g., cancer (e.g., benign and malignant), benign prostatic hyperplasia, psoriasis, abnormal keratinization, lymphoproliferative disorders (e.g., a disorder in which there is abnormal proliferation of cells of the lymphatic system), chronic rheumatoid arthritis, arteriosclerosis, restenosis, diabetic retinopathy, and neurodegenerative disorders. Proliferative disorders are described in U.S. Pat. Nos. 5,639,600 and 7,087,648, hereby incorporated by reference.

Diabetes and Obesity

Adipose tissue expresses PKM2. Thus, compounds of the invention described herein may be useful in the treatment of obesity. Additionally, inhibitors of PKM2 described herein may be useful in the treatment of type II diabetes, as the inhibition of PKM2 may allow for decreased lipid production in adipose tissue.

Additional Therapeutic Regimens

If desired, additional therapeutic regimens may be provided along with the compounds described herein. For example, therapeutic agents may be administered with the inhibitors of PKM2 described herein at concentrations known to be effective for such therapeutic agents. Particularly useful agents include, e.g., antimicrobial agents, anti-inflammatory agents, antiviral agents, antifungal agents, analgesics, anesthetics, sedatives, lubricants, immunomodulatory agents, and 5-aminosalicylate derivatives.

If more than one agent is employed, therapeutic agents may be delivered separately or may be admixed into a single formulation. When agents are present in different pharmaceutical compositions, different routes of administration may be employed. Routes of administration include, e.g., ocular, inhalation, parenteral, dermal, transdermal, buccal, rectal, sublingual, perilingual, nasal, topical administration, or oral administration. Parenteral administration includes intravenous, intraperitoneal, subcutaneous, and intramuscular administration.

The therapeutic agents described herein may be admixed with additional active or inert ingredients, e.g., in conventional pharmaceutically acceptable carriers. A pharmaceutical carrier can be any compatible, non-toxic substance suitable for the administration of the compositions of the present invention to a patient. Pharmaceutically acceptable carriers include, for example, water, saline, buffers and other compounds, described, for example, in the Merck Index, Merck & Co., Rahway, N.J. Slow release formulations or a slow release apparatus may be also be used for continuous administration.

In addition to the administration of therapeutic agents, the additional therapeutic regimen may involve other therapies, including modification to the lifestyle of the subject being treated.

Formulation of Pharmaceutical Compositions

The administration of the compounds described herein may be by any suitable means that results in a concentration of the compound that is effective in treating the disease associated with PKM2 function. The compound may be contained in any appropriate amount in any suitable carrier substance. The composition may be provided in a dosage form that is suitable for the oral, parenteral (e.g., intravenous or intramuscular), rectal, cutaneous, nasal, vaginal, inhalant, skin (e.g., a patch), ocular, or intracranial administration route. Thus, the composition may be in the form of, e.g., tablets, capsules, pills, powders, granulates, suspensions, emulsions, solutions, gels including hydrogels, pastes, ointments, creams, plasters, drenches, osmotic delivery devices, suppositories, enemas, injectables, implants, sprays, or aerosols. The pharmaceutical compositions may be formulated according to conventional pharmaceutical practice (see, e.g., Remington; *The Science and Practice of Pharmacy,* 20th edition, 2000, ed. A. R. Gennaro, Lippincott Williams & Wilkins, Philadelphia, and *Encyclopedia of Pharmaceutical Technology*, eds. J. Swarbrick and J. C. Boylan, 1988-1999, Marcel Dekker, New York).

Pharmaceutical compositions according to the invention may be formulated to release the active compound immediately upon administration or at any predetermined time or time period after administration. The latter types of compositions are generally known as controlled release formulations, which include (i) formulations that create substantially constant concentrations of the agent(s) of the invention within the body over an extended period of time; (ii) formulations that after a predetermined lag time create substantially constant concentrations of the agents of the invention within the body over an extended period of time; (iii) formulations that sustain the agent(s) action during a predetermined time period by maintaining a relatively constant, effective level of the agent(s) in the body with concomitant minimization of undesirable side effects associated with fluctuations in the plasma level of the agent(s) (sawtooth kinetic pattern); (iv) formulations that localize action of agent(s), e.g., spatial placement of a controlled release composition adjacent to or in the diseased tissue or organ; (v) formulations that achieve convenience of dosing, e.g., administering the composition once per week or once every two weeks; and (vi) formulations that target the action of the agent(s) by using carriers or chemical derivatives to deliver the combination to a particular target cell type. Administration of the combination in the form of a controlled release formulation is especially preferred for compounds having a narrow absorption window in the gastro-intestinal tract or a relatively short biological half-life.

Any of a number of strategies can be pursued in order to obtain controlled release in which the rate of release outweighs the rate of metabolism of the compound in question. In one example, controlled release is obtained by appropriate selection of various formulation parameters and ingredients, including, e.g., various types of controlled release compositions and coatings. Thus, the combination is formulated with appropriate excipients into a pharmaceutical composition that, upon administration, releases the combination in a controlled manner. Examples include single or multiple unit tablet or capsule compositions, oil solutions, suspensions, emulsions, microcapsules, molecular complexes, microspheres, nanoparticles, patches, and liposomes.

Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Nanoparticulate formulations (e.g., biodegradable nanoparticles, solid lipid nanoparticles, and liposomes) may be used to control the biodistribution of the compounds. Other potentially useful parenteral delivery systems include ethylene-vinyl acetate copolymer particles, osmotic pumps, implantable infusion systems, and liposomes.

Formulations for inhalation may contain excipients or may be aqueous solutions containing, for example, polyoxyethylene-9-lauryl ether, glycholate and deoxycholate, or may be oily solutions for administration in the form of nasal drops, or as a gel. The concentration of the compound in the formulation will vary depending upon a number of factors, including the dosage of the drug to be administered, and the route of administration.

Formulations for oral use include tablets containing the active ingredient(s) in a mixture with non-toxic pharmaceutically acceptable excipients. These excipients may be, for example, inert diluents or fillers (e.g., sucrose and sorbitol), lubricating agents, glidants, and antiadhesives (e.g., magnesium stearate, zinc stearate, stearic acid, silicas, hydrogenated vegetable oils, or talc). Formulations for oral use may also be provided in unit dosage form as chewable tablets, tablets, caplets, or capsules (e.g., as hard gelatin capsules wherein the active ingredient is mixed with an inert solid diluent or as soft gelatin capsules wherein the active ingredient is mixed with water or an oil medium).

The compound may be optionally administered as a pharmaceutically acceptable salt, such as, e.g., a non-toxic acid addition salt or metal complex that is commonly used in the pharmaceutical industry. Examples of acid addition salts include, e.g., organic acids (e.g., acetic, lactic, pamoic, maleic, citric, malic, ascorbic, succinic, benzoic, palmitic, suberic, salicylic, tartaric, methanesulfonic, toluenesulfonic, or trifluoroacetic acids), polymeric acids (e.g., tannic acid or carboxymethyl cellulose), and inorganic acids (e.g., hydrochloric acid, hydrobromic acid, sulfuric acid, or phosphoric acid). Metal complexes include, e.g., zinc and iron complexes.

The formulations can be administered to human subjects in therapeutically effective amounts. Typical dose ranges are from about 0.01 μg/kg to about 2 mg/kg of body weight per day. The preferred dosage of drug to be administered is likely to depend on such variables as the type and extent of the disorder, the overall health status of the particular subject, the specific compound being administered, the excipients used to formulate the compound, and its route of administration. Standard clinical trials maybe used to optimize the dose and dosing frequency for any particular compound.

EXAMPLES

The following examples are put forth so as to provide those of ordinary skill in the art with a complete disclosure and description of how the methods and compounds claimed herein are performed, made, and evaluated, and are intended to be purely exemplary of the invention and are not intended to limit the scope of what the inventors regard as their invention.

Example 1

PKM2 Expression in Tumor Tissue

Figure 4:
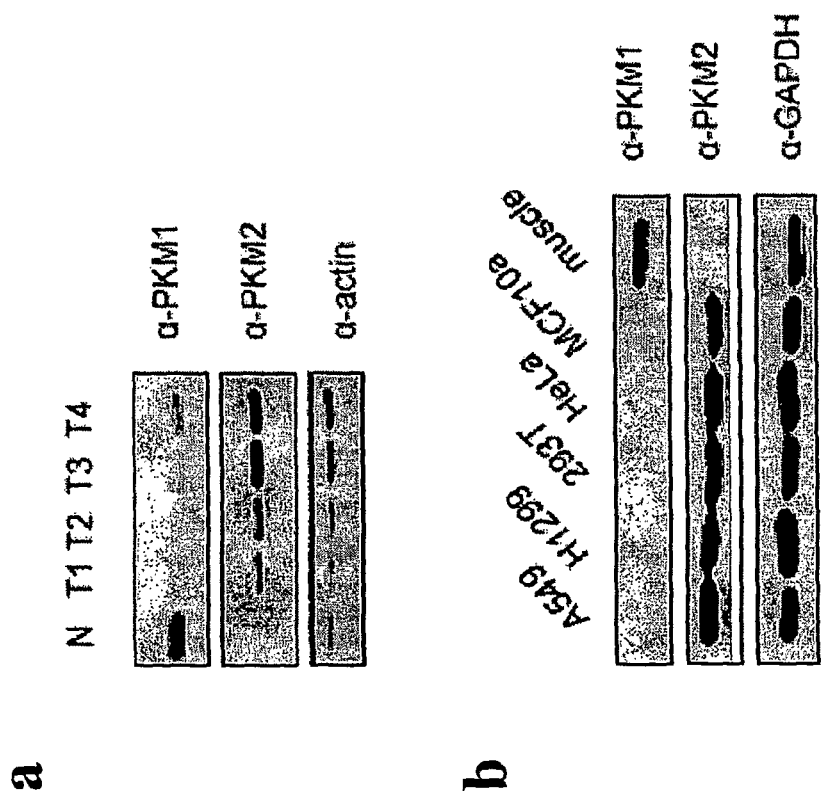
FIG. 4 shows that tumor tissues and cell lines express the M2 isoform of pyruvate kinase.

To confirm that tumor tissues switch PK expression from an adult isoform to the embryonic M2 isoform, antibodies that distinguish PKM1 from PKM2 were generated (FIG. 3). Mammary gland tissues from MMTV-neuNT mice, a breast cancer tumor model, were analyzed before and after tumor development for PK isoform expression. The cells were lysed in Nonidet P-40 lysis buffer and Western blot analysis was carried out according to standard protocols. As shown in FIG. 4a, the primary PK isoform prior to tumor development is PKM1; however, the primary isoform from four independent tumors is PKM2. All cell lines examined, including multiple cancer lines derived from different tissues, also exclusively express the M2 isoform of PK (FIG. 4b).

Example 2

PKM Inhibition Decreases Glycolysis in Tumor Tissue

Figure 5:
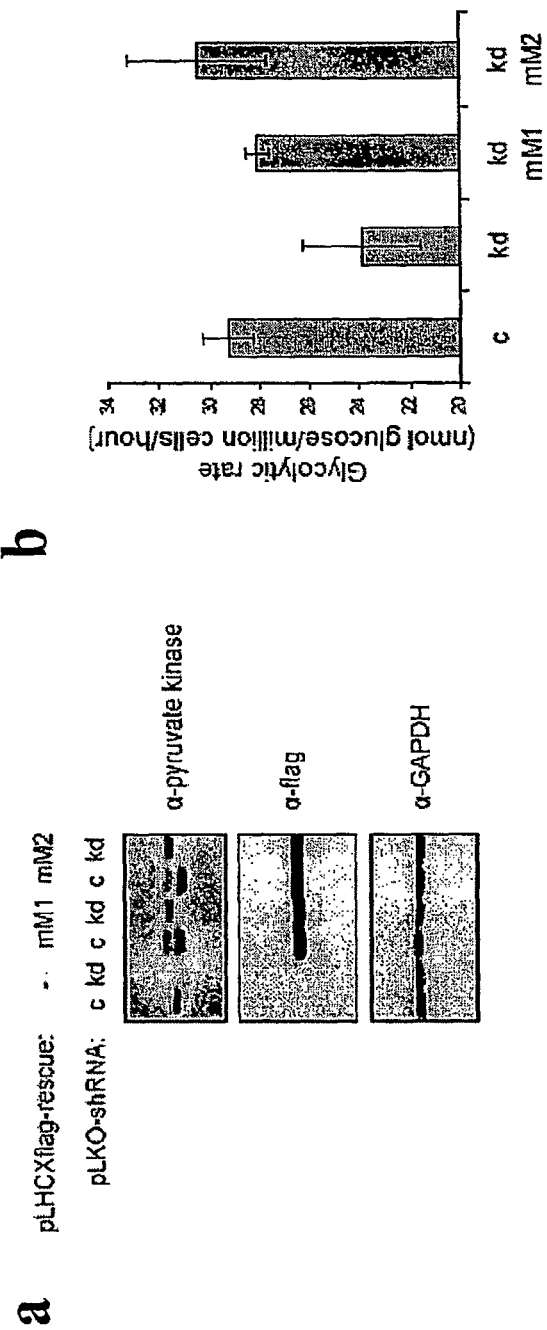
FIG. 5a shows an immunoblot of H1299 cells stably expressing shRNA constructs and rescue constructs. Cells were infected with retrovirus containing the empty vector, pLHCX, or pLHCX with flag-tagged mouse M1 (mM1) or mouse M2 (mM2). After two weeks selection in hygromycin, the cells were infected with lentivirus containing the pLKO vector with control shRNA (c) or shRNA that knocks down PKM2 expression (kd). The cells were then selected in puromycin for one week. Total cell extracts were immunoblotted with antibodies for PKM, flag, and GAPDH.
FIG. 5b shows the glycolytic rates of the knockdown and rescue cells. Bars denote s.e.m. (n=3) in FIG. 5b.

The role of PKM2 in glycolysis was assessed by short hairpin RNA (shRNA) knockdown (FIG. 5a). Cellular glycolysis rates were measured by following the conversion of 5-$^3$H-glucose to $^3$H$_2$O. The assay was performed with cells attached to tissue plates. The cells were washed once in PBS, prior to incubation in Krebs buffer containing 10 mM glucose spiked with 10 µCi of 5-$^3$H-glucose. After one hour, triplicate samples of media were transferred to PCR tubes containing 0.2 N HCl and the amount of $^3$H$_2$O generated was determined by diffusion, as has been previously described in the art.

The data show that stable knockdown of PKM2 in the human lung cancer cell line H1299 results in decreased glycolytic rates (FIG. 5b).

Example 3

M1 Expression Reduces the Tumorigenicity of Lung Cancer Cells

Figure 6:
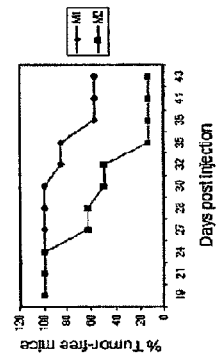
FIG. 6 shows that M1 expression reduces the tumorigenicity of lung cancer cells.
Figure 6:
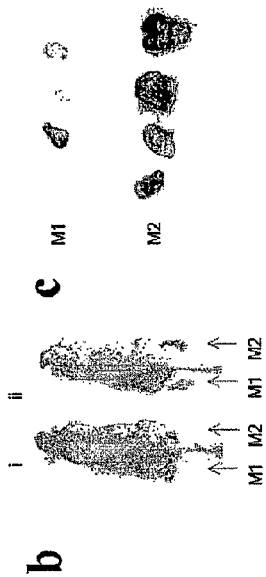
Figure 6:
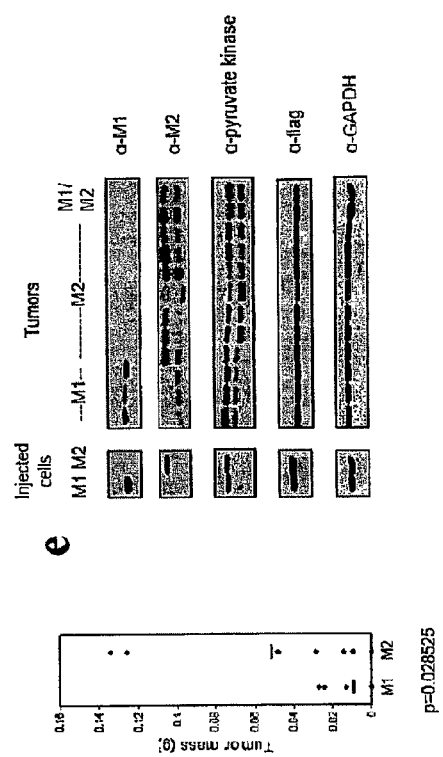

To determine whether M2 isoform expression is important for tumor cell growth in vivo, xenograft studies were performed using the M1 and M2 rescue cells. Nude mice were injected with 5 million M1 or M2 rescue H1299 cells, and tumor growth was monitored over a seven-week period. As shown in FIG. 6a, mice injected with the M1 cells showed a delay in tumor development as compared with those injected with the M2 cells. Fewer tumors developed from the M1 cells, and those that did were smaller in size (FIGS. 6b and 6c). As judged by total tumor mass, the M2 cells gave rise to significantly larger tumors than the MI cells (FIG. 6d). Western blot analysis of the developed tumors shows the flag-tagged rescue mM1 and mM2 proteins are retained in the tumors. However, endogenous expression of PKM2 returned in both cases (FIG. 6e). No tumors were recovered that solely expressed mM1. To determine whether this was the result of loss of shRNA-mediated knockdown of endogenous PKM2 or whether it represented a selective growth advantage for cells expressing M2, a 50/50 mixture of the M1 and M2 cells were injected into nude mice. Tumors that arose from the mixture of M1 and M2 cells only retained expression of the flag-mM2 rescue protein, demonstrating that the majority of the tumor, if not the entire tumor, was derived from the M2-expressing cells (FIG. 6e). These data show that PKM2 expression provides a selective growth advantage for tumor cells in vivo.

The switch to the M2 isoform of PK in tumor cells is sufficient to cause the metabolic phenotype known as the Warburg effect. However, it remains unclear how the pyruvate made from PKM2 is converted to lactate while the pyruvate made from PKM1 is metabolized in the mitochondria. One explanation is that M2 expression results in higher expression of lactate dehydrogenase. Alternatively, M2 expression could lead to reduced mitochondrial density and decreased expression of proteins involved in oxidative phosphorylation. To test these hypotheses, we analyzed the expression of the lactate dehydrogenase and F1F0-ATPase proteins in the M1 and M2 cells. No differences in the protein levels were detected (data not shown); however, differential activities of lactate dehydrogenase or proteins involved in oxidative phosphorylation in the M1 and M2 cells could account for the observed shift to aerobic glycolysis in the M2-expressing cells.

Example 4

Method for Identifying Inhibitors of Pyruvate Kinase

An in vitro screen was devised to identify inhibitors of PKM2. By utilizing the ability of PKM2, but not PKM1, to be allosterically activated by fructose-1,6-bisphosphate (FBP), a screen was performed to identify molecules which specifically inhibit the activation of PKM2 by FBP.

Recombinant PKM1 and PKM2 were expressed in E. coli and purified using an Ni-NTA column according to standard protocols. PKM2 (2 pg) was mixed with the following components: 0.6 mM ADP, 0.5 mM phosphoenolpyruvate, 200 µM NADH, 1-4 units of lactate dehydrogenase, 50 µM FBP, 1 mM DTT, 0.02% Brij 35, 5% glycerol, and the test molecule with a final DMSO concentration of 5%. A control reaction lacked the test molecule. The test molecules used in this example were selected from a library containing over 100,000 compounds.

Primary screening was performed using PKM2 in the presence of FBP. Compounds were chosen as potential "hits" if the compound demonstrated inhibition of PKM2 activity greater than 50%. Activity was measured by monitoring the concentration of NADH. Pyruvate, produced by the enzymatic activity of pyruvate kinase, is converted into lactate by lactate dehydrogenase, which requires the consumption of NADH (NADH→NAD$^+$). Thus, the activity of PKM2 was indirectly measured by monitoring the consumption of NADH through fluorescence assays. Additionally, the activity of the PKM2 enzyme was directly monitored by measuring the production of ATP, as ATP is produced when phosphoenolpyruvate is converted to pyruvate by PKM2.

Figure 7:
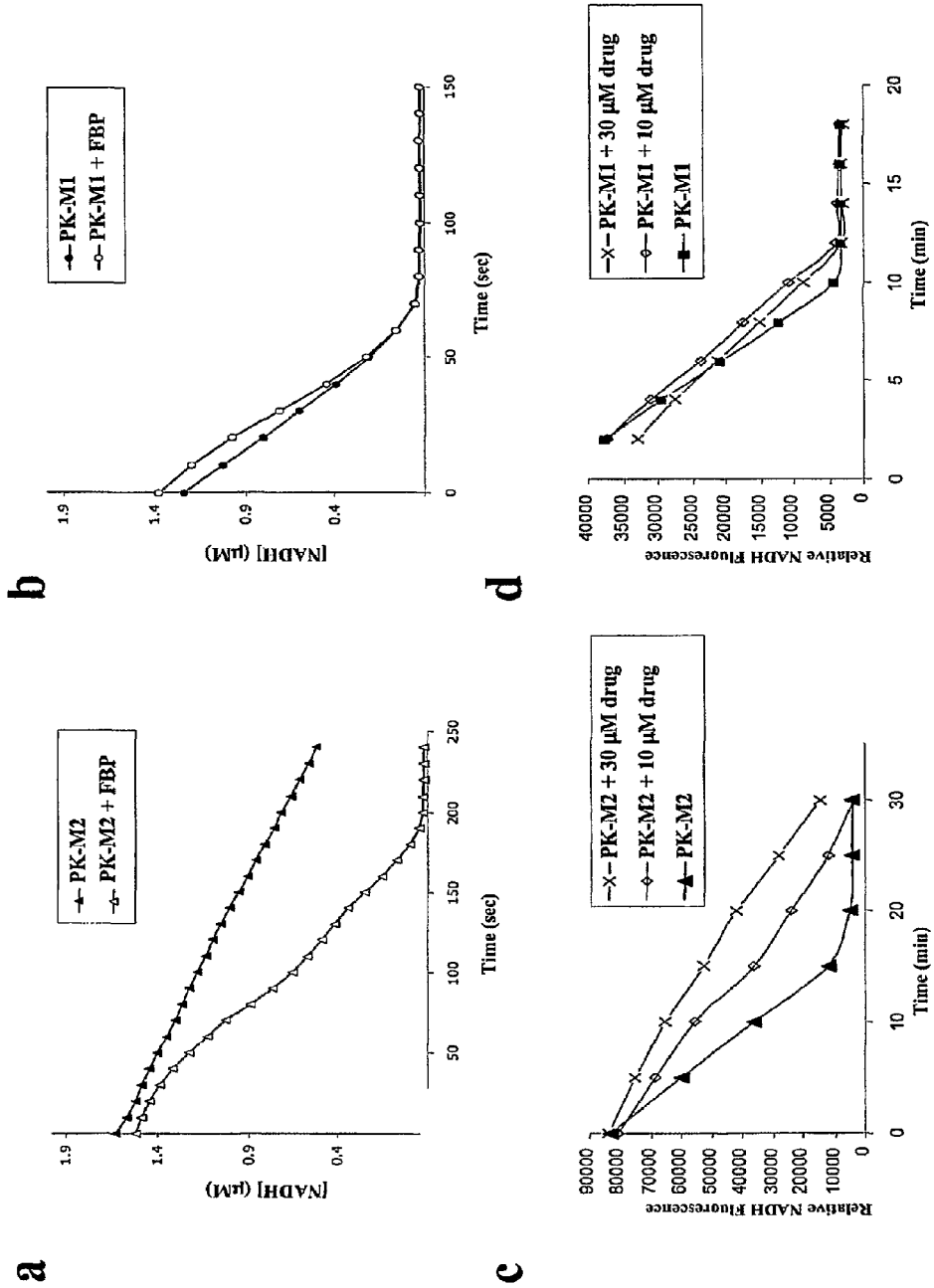
FIGS. 7a-d show PKM2 specific activation and inhibition of pyruvate kinase enzyme activity.

This same screening method was then used to retest candidate molecules for the inhibition of PKM1 to determine which candidate compounds are active against PKM2, but not PKM1. Examples of PKM2-specific activation by lead compounds are shown in FIG. 7.

FIG. 1 shows eleven candidate compounds belonging to eight different chemical genera that inhibit PKM2, inhibit glycolysis, and inhibit cancer cell growth.

Example 5

IC50 of PKM2 Inhibition and Cancer Growth Inhibition of the Eleven Lead Compounds and Percent Inhibition of PKM2 and PKM1 at Screening Concentration For in vitro studies, recombinant pyruvate kinase was incubated with the compound indicated (Table 2) and the activity of the enzyme assessed, as described in Example 4. To determine the IC50, enzyme activity was determined at various concentrations of inhibitor. The percentages shown in Table 2 reflect the inhibition of enzyme activity relative to the absence of compound when the enzyme is incubated with 50 μM of the compound indicated. For in vivo studies, human lung cancer cell lines were incubated with increasing concentrations of the compound indicated and the concentration required to kill >90% of the cells is reported.

TABLE 2

| Compound (Family) | IC50 in vitro (PKM2) | IC50 in vivo[1] | PKM2[2] | PKM1[2] |
|---|---|---|---|---|
| A1 (I) | ~90 μM | >100 μM | 50% | 15% |
| A2 (I) | 7 μM | ~250 μM | 50% | 15% |
| A3 (I) | >100 μM | >100 μM | 50% | 0% |
| B1 (II) | ~10 μM | — | 85% | 0% |
| C1 (III) | — | — | 75% | 20% |
| D1 (IV) | 20 μM | ~250 μM | 70% | 15% |
| D2 (IV) | — | — | 25% | 0% |
| E1 (V) | — | — | 25% | 15% |
| F1 (VI) | 10 μM | ~90 μM | — | — |
| G1 (VII) | ~70 μM | >500 μM | — | — |
| H1 (VIII) | 90 μM | >500 μM | — | — |

[1]In vivo data obtained using H1299 and A549 human lung cancer cells
[2]The screening concentration was estimated at 50 μM.

Example 5

Cancer Cell Growth Inhibition by Candidate Compounds

Figure 8:
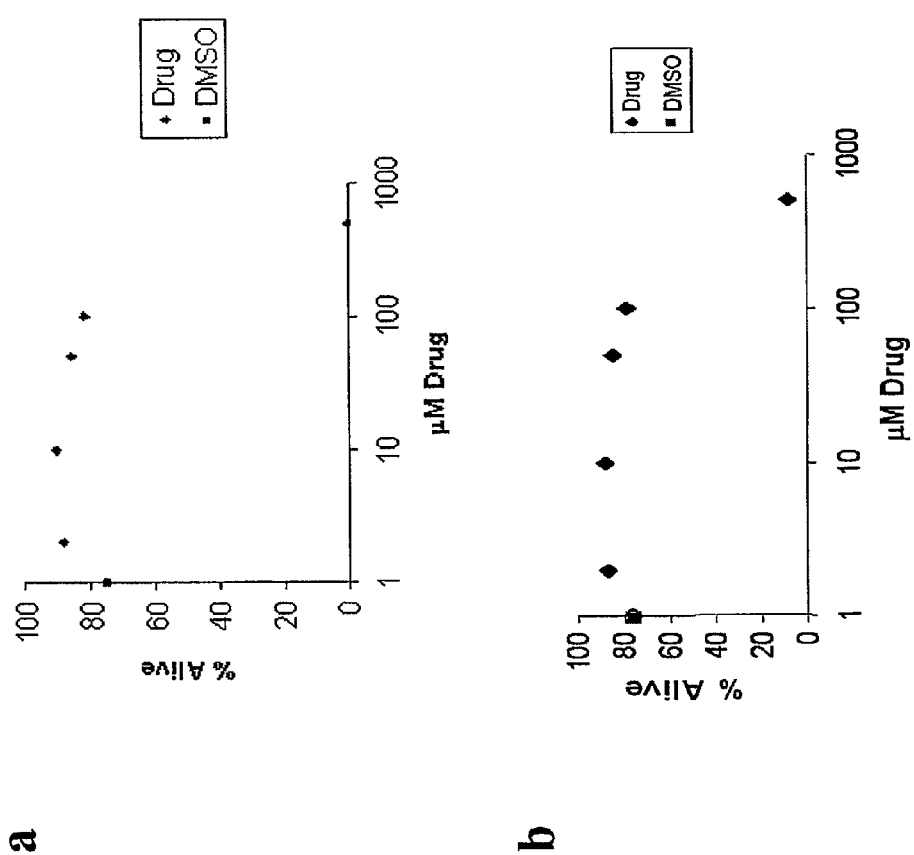
FIG. 8 depicts the toxicity of compound A2 (FIG. 8a) and D1 (FIG. 8b) in human lung cancer cells after two days of treatment compared to mock-treatment with DMSO.
Figure 10:
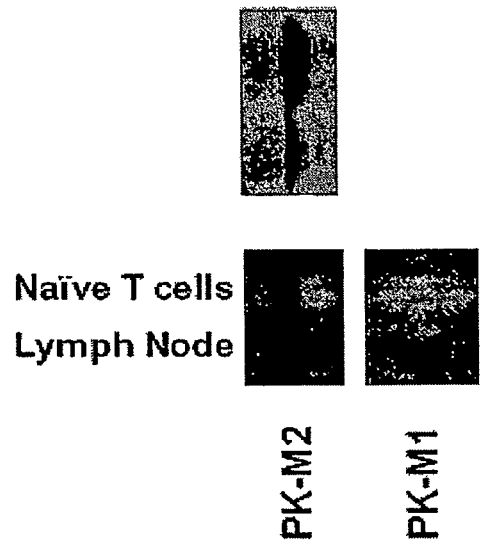
FIG. 10 shows the differentiation and proliferation of T cells. A Western blot shows the expression of PKM2, but not PKM1, in T cells. Increased PKM2 expression is shown at time points following T cell activation with anti-CD3 and anti-CD28 antibodies.

Human lung cancer cells were exposed to increasing concentrations of candidate compounds A2 and D1. The toxicity of the compounds was measured by determining the percentage of surviving cells. Cells were mock-treated with DMSO as a control. FIG. 10 depicts the toxicity of compounds A2 (FIG. 8a) and D1 (FIG. 8b) in H1299 cells compared to mock treatment with DMSO.

Example 7

Immune Suppression by Candidate Compounds

Figure 9:
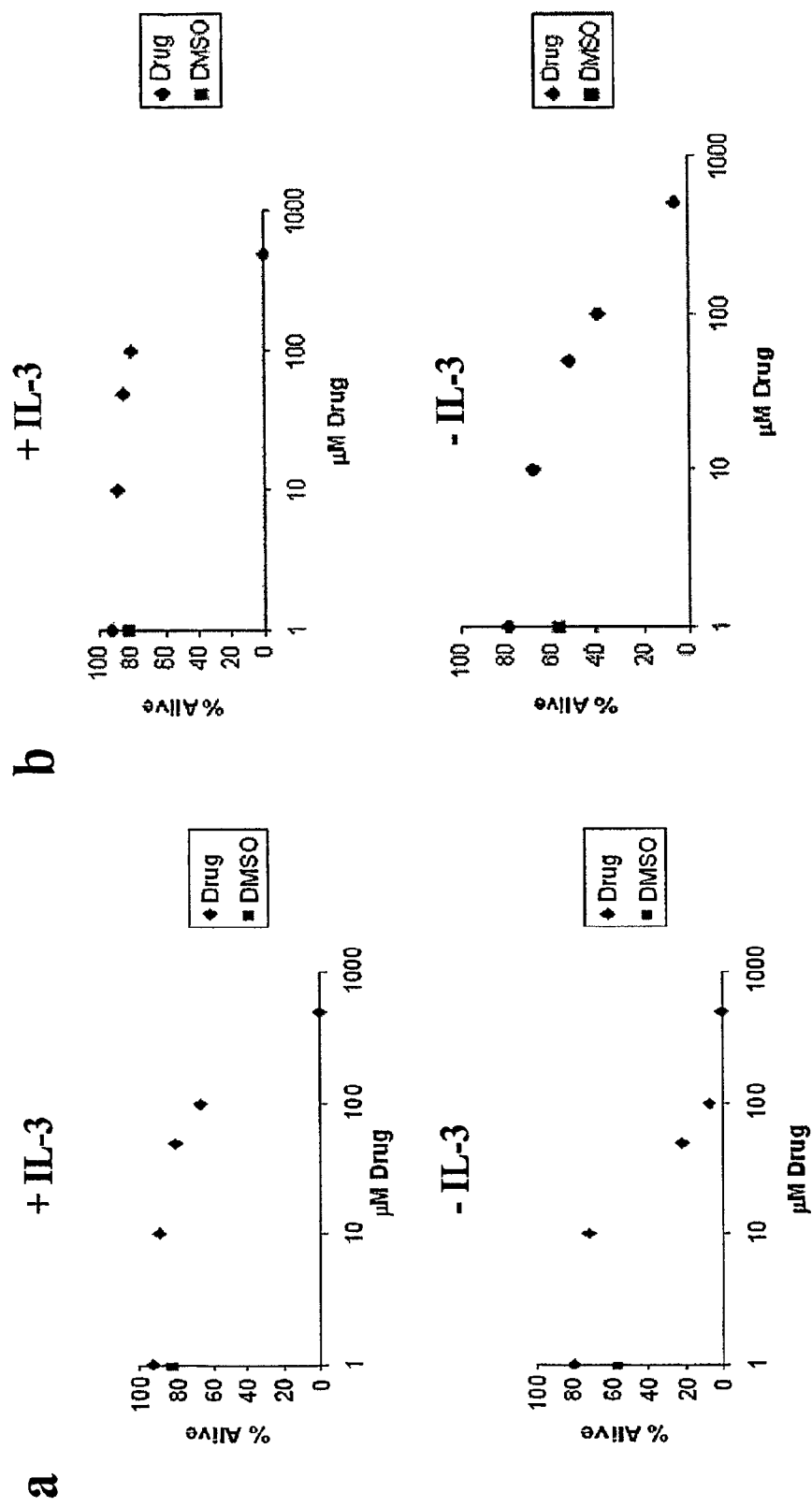
FIG. 9 depicts the toxicity of compound A2 (FIG. 9a) and D1 (FIG. 9b) in FL5.12 cells, a mouse pre-lymphocyte cell line, after twenty hours of treatment, in the presence (+) or absence of growth factor (IL-3).

Mouse pre-lymphocyte cells (FL5.12 cells) were treated with candidate compounds A2 (FIG. 9a) and D1 (FIG. 9b) for twenty hours in the presence and absence of growth factor (IL-3). Growth factor withdrawal increases the toxicity of the candidate compound, suggesting that autoimmune diseases may be treated by inhibiting PKM2.

Example 8

Expression of PKM2 in Immunogenic Cells

The expression of PKM1 and PKM2 was monitored in naïve T cells using the specific PKM1 and PKM2 antibodies generated (see FIG. 3). As shown in the Western blot in FIG. 10, T cells express pyruvate kinase M2, but not the M1 isoform. The expression of pyruvate kinase M2 increased following T-cell activation with anti-CD3 and anti-CD28 antibodies at 24-hour and 48-hour time points.

Example 9

Expression of PKM2 in Adipose Tissue and Proliferating Cells

Figure 11:
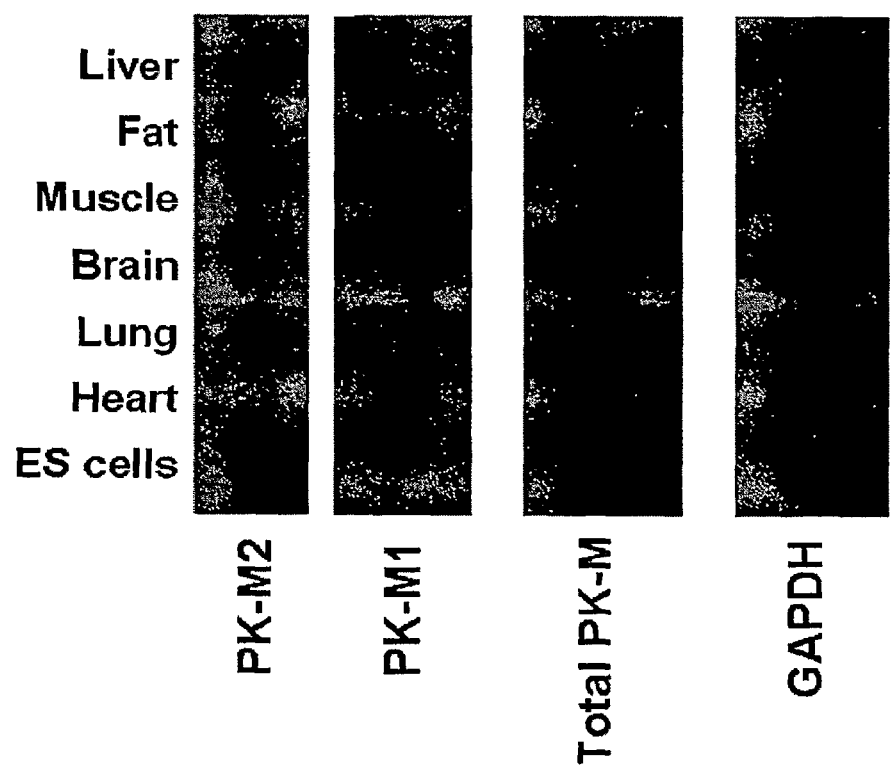
FIG. 11 shows a Western blot illustrating the selective expression of PKM2 in embryonic cells and adipose cells.

FIG. 11 depicts a Western blot showing the selective expression of pyruvate kinase M2 in embryonic cells and adipose cells. These data suggest that inhibitors of PKM2 may be used to treat diseases such as, e.g., diabetes, obesity, and proliferation dependent diseases (e.g., BPH).

Other Embodiments

All publications, patents, and patent applications mentioned in this specification are herein incorporated by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims.

Other embodiments are within the claims.

What is claimed is:

1. A pharmaceutical composition comprising a compound selected from:

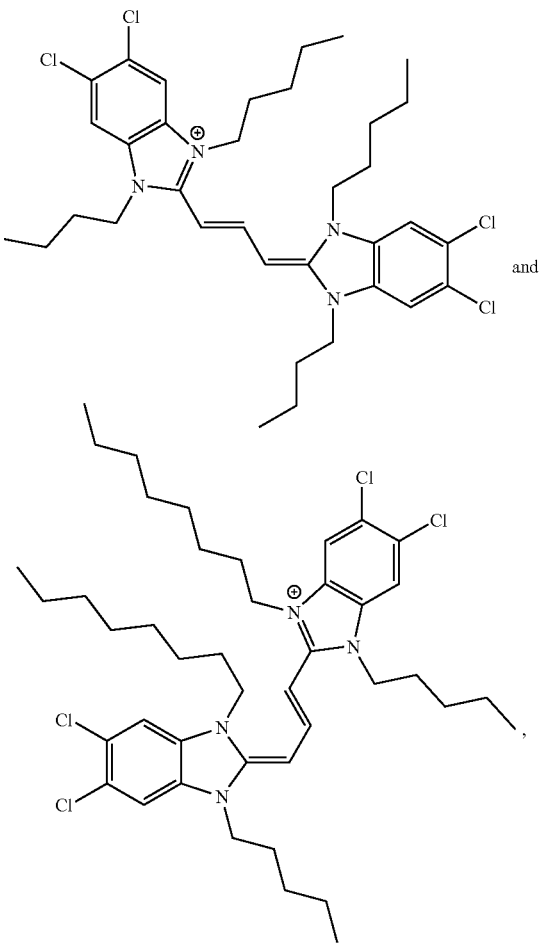

and a pharmaceutically acceptable excipient, wherein said pharmaceutical composition is formulated for oral administration in unit dosage form, for topical administration, or for intravenous administration.

* * * * *